US008106251B2

(12) United States Patent
Ayares et al.

(10) Patent No.: US 8,106,251 B2
(45) Date of Patent: Jan. 31, 2012

(54) TISSUE PRODUCTS DERIVED FROM PORCINE ANIMALS LACKING ANY EXPRESSION OF FUNCTIONAL ALPHA 1,3 GALACTOSYLTRANSFERASE

(75) Inventors: David Ayares, Blacksburg, VA (US); Paul Rohricht, Mertztown, PA (US)

(73) Assignee: Revivicor, Inc., Blacksburg, VA (US)

( * ) Notice: Subject to any disclaimer, the term of this patent is extended or adjusted under 35 U.S.C. 154(b) by 0 days.

(21) Appl. No.: 11/083,393

(22) Filed: Mar. 17, 2005

(65) Prior Publication Data
US 2005/0260176 A1 Nov. 24, 2005

Related U.S. Application Data

(63) Continuation-in-part of application No. 10/646,970, filed on Aug. 21, 2003, now Pat. No. 7,795,493.

(60) Provisional application No. 60/404,775, filed on Aug. 21, 2002, provisional application No. 60/559,816, filed on Apr. 6, 2004, provisional application No. 60/553,895, filed on Mar. 17, 2004.

(51) Int. Cl.
*A01K 67/027* (2006.01)
*A61F 2/08* (2006.01)

(52) U.S. Cl. ... 800/17; 623/2.11; 623/11.11; 623/13.11; 623/15.11; 623/16.11

(58) Field of Classification Search .................... 800/17, 800/24
See application file for complete search history.

(56) References Cited

U.S. PATENT DOCUMENTS

| | | | |
|---|---|---|---|
| 4,797,368 A | 1/1989 | Carter et al. |
| 4,863,852 A | 9/1989 | Wilkins et al. |
| 5,175,383 A | 12/1992 | Leder et al. |
| 5,354,768 A | 10/1994 | Terada et al. |
| 5,474,935 A | 12/1995 | Chatterjee et al. |
| 5,523,226 A | 6/1996 | Wheeler |
| 5,681,731 A | 10/1997 | Lebkowski et al. |
| 5,714,353 A | 2/1998 | Pathak et al. |
| 5,821,117 A | 10/1998 | Sandrin et al. |
| 5,849,991 A | 12/1998 | d'Apice et al. |
| 5,850,004 A | 12/1998 | MacMicking et al. |
| 5,922,601 A | 7/1999 | Baetscher et al. |
| 5,942,435 A | 8/1999 | Wheeler |
| 6,153,428 A | 11/2000 | Gustafsson et al. |
| 6,235,969 B1 | 5/2001 | Stice et al. |
| 6,258,998 B1 | 7/2001 | Damiani et al. |
| 6,331,658 B1 | 12/2001 | Cooper et al. |
| 6,413,769 B1 | 7/2002 | Gustafsson et al. |
| 6,455,037 B1 | 9/2002 | Ioannou et al. |
| 6,849,448 B1 | 2/2005 | D'Apice et al. |
| 2001/0055584 A1 | 12/2001 | McKenzie et al. |
| 2002/0031494 A1 | 3/2002 | Sandrin et al. |
| 2002/0152488 A1 | 10/2002 | Cooper et al. |
| 2003/0014770 A1 | 1/2003 | Gustafsson et al. |
| 2003/0203427 A1 | 10/2003 | Koike |
| 2004/0268424 A1 | 12/2004 | Phelps |
| 2005/0028228 A1 | 2/2005 | McQuillan et al. |
| 2005/0120400 A1 | 6/2005 | Day et al. |

FOREIGN PATENT DOCUMENTS

| | | |
|---|---|---|
| EP | 0669829 B1 | 8/2001 |
| JP | 06-253856 A1 | 9/1994 |
| WO | WO 94/02616 A1 | 2/1994 |
| WO | WO 94/09803 A1 | 5/1994 |
| WO | WO 94/21799 A1 | 9/1994 |
| WO | WO 94/24870 A1 | 11/1994 |
| WO | WO 95/20661 A1 | 8/1995 |
| WO | WO 95/28412 A1 | 10/1995 |
| WO | WO 95/34202 A1 | 12/1995 |
| WO | WO 96/06165 A1 | 2/1996 |
| WO | WO 96/28967 A1 | 9/1996 |
| WO | WO 96/37602 A1 | 11/1996 |
| WO | WO 96/40244 A1 | 12/1996 |
| WO | WO 97/16064 A1 | 5/1997 |
| WO | WO 97/16727 A1 | 5/1997 |
| WO | WO 98/05768 A1 | 2/1998 |
| WO | WO 98/07444 A1 | 2/1998 |
| WO | WO 98/07837 A1 | 2/1998 |
| WO | WO 98/33528 A2 | 8/1998 |
| WO | WO 99/09141 A1 | 2/1999 |
| WO | WO 99/09163 A1 | 2/1999 |
| WO | WO 99/19469 A1 | 4/1999 |
| WO | WO 99/21415 A1 | 5/1999 |
| WO | WO 99/49029 A1 | 9/1999 |
| WO | WO 00/06194 A2 | 2/2000 |
| WO | WO 00/11147 A1 | 3/2000 |
| WO | WO 00/51424 A2 | 9/2000 |
| WO | WO 00/51424 A3 | 9/2000 |
| WO | WO 01/23541 A2 | 4/2001 |
| WO | WO 01/30992 A2 | 5/2001 |

(Continued)

OTHER PUBLICATIONS

Teebken et al. Tissue Engineering of Vascular Grafts: Human Cell Seeding of Decellularised Porcine Matrix. European Journal of Vascular Endovascular Surgery. 2000, vol. 19,.pp. 381-386.*

Dejardin et al. Tissue-Engineered Rotator Cuff Tendon Using Porcine Small Intestin Submucosa. The American Journal of Sports Medicine. 2001, vol. 29, pp. 175-184.*

Friedman et al Human CD4+ T Cells Mediate Rejection of Porcine Xenografts. Journal of Immunology. 1999, vol. 162, pp. 5256-5262.*

Chen et al. Transgenic Porcine Valves Show No Signs of Delayed Cardiac Xenograft Rejection. Annals Society Thoracic Surg., 2001, vol. 71, pp. S389-S392.*

Badylack. The Extracellular Martrix as a Scaffold for Tissue Reconstruction. Seminars in Cell & Developmental Biology. 2002, vol. 13, pp. 377-383.*

(Continued)

*Primary Examiner* — Deborah Crouch
(74) *Attorney, Agent, or Firm* — King & Spalding

(57) ABSTRACT

The present invention provides tissues derived from animals, which lack any expression of functional alpha 1,3 galactosyltransferase (alpha-1,3-GT). Such tissues can be used in the field of xenotransplantation, such as orthopedic reconstruction and repair, skin repair and internal tissue repair or as medical devices.

7 Claims, 7 Drawing Sheets

FOREIGN PATENT DOCUMENTS

| WO | WO 02/10337 A2 | 2/2002 |
|---|---|---|
| WO | WO 03/013342 A2 * | 2/2003 |
| WO | WO 03/055302 A1 | 7/2003 |
| WO | WO 2004/016742 A2 | 2/2004 |
| WO | WO 2004/028243 A2 | 4/2004 |
| WO | WO 05/009134 A1 | 2/2005 |

OTHER PUBLICATIONS

Metzger. Immune Responses to Tissue-Engineered Extracellular Matrix Used as a Bioscaffold. Annals of the New York Acadmeis of Science. 2002. vol. 961, pp. 335-336.*

Ayares, D., et al., (PPL Therapeutics, Inc.), "Gene targeting in livestock," Transgenic Animal Research Conference (hosted by Univ. of Calif. at Davis biotechnology program, at the Granlibakken Conf. Ctr. in Tahoe City, CA, Jul. 1999 [http:www.biotech.ucdavis.edu]), abstract at p. 20.

Ayares, D., et al., PPL Therapeutics, Inc.), "Gene targeting in livestock for production of novel biopharmaceuticals," ISB News Report (published by Information Systems for Biotechnology), Nov. 1999:5-6, at http://www.isb.vt.edu/news/1999/Nov44.pdf.

Ayares, D., et al., "Cloning pigs deficient an α1,3 galactosyltransferase," Graft, 4(1):80-83 (2001).

Bach, F.H., et al., "Delayed xenograft rejection," Immunol. Today, 17(8):379-384 (Aug. 1996).

Betthauser, J., et al., "Production of cloned pigs from in vitro systems," Nature Biotechnology,. 18(10):1055-1059 (Oct. 2000).

Bondioli, K., et al., Cloned pigs generated from cultured skin fibroblasts derived from a H-transferase transgenic boar, Molecular Reproduction and Development, 60(2):189-195 (Oct. 2001).

Brandon, E.P., et al., "targeting the mouse genome: A compendium of knockouts (part I)," Current Biology, 5[6]:625-634 (1995).

Brandon, E.P., et al., "targeting the mouse genome: A compendium of knockouts (part II)," Current Biology, 5[7]:758-765 (1995).

Brandon, E.P., et al., "targeting the mouse genome: A compendium of knockouts (part III)," Current Biology, 5[8]:873-881 (1995).

Butler, D., "Xenotransplant experts express caution over knockout piglets," Nature, 415(6868):103-104 (Jan. 10, 2002).

Capecchi, M.R., et al., "Altering the genome by homologous recombination," Science, 244(4910):1288-1292 (Jun. 16, 1989).

Clark, A.J., et al., "Gene targeting in livestock: a preview," Transgenic Res., 9(4-5):263-275 (2000).

Clark, G.F., et al., "Toxin A from Clostridium dificile binds to rabbit erythrocyte glycolipids with terminal Gal alpha 1-3Gal beta 1-4GlcNAc sequences," Arch.Biochem.Biophys., 257(1):217-229, (Aug. 15, 1987).

Cooper, D.K., et al., "Oligosaccharides and discordant xenotransplantation," Immunol. Rev., 141:31-58 (Oct. 1994).

Cooper, D.K.C., et al., "Genetically engineered pigs," Lancet, 342:682-683 (Sep. 11, 1993).

Costa, C., et al., "Expression of the human α1,2-fucosyltransferase in transgenic pigs modifies the cell surface carbohydrate phenotype and confers resistance to human serum-mediated cytolysis," FASEB J., 13:1762-1773 (Oct. 1999).

Dabkowski, P.L., et al., "Characterisation of a cDNA clone encoding the pig alpha 1,3 galactosyltransferase: implications for xenotransplantation," Transplant Proc., 25(5):2921 (Oct. 1993).

Dabkowski, P.L., et al., "Isolation of a cDNA clone encoding the pig alpha 1,3 galactosyltransferase," Transplant Proc., 26(3):1335 (Jun. 1994).

Dai, Y., et al., "Targeted disruption of the α1,3-galactosyltransferase gene in cloned pigs," Nature Biotechnology, 20:251-255 (Mar. 2002).

Dalmasso, A.P., et al., "Inhibition of complement-mediated endothelial cell cytotoxicity by decay-accelerating factor: Potential for prevention of xenograft hyperacute rejection," Transplantation, 52(3):530-533 (Sep. 1991).

Dalmasso, A.P., et al., "Reaction of complement with endothelial cells in a model of xenotransplantation," Clin. Exp .Immunol., 86:31-35 (1991).

D'Apice, A.J., et al., "Two genetic approaches to the galactose alpha 1,3 galactose xenoantigen," Transplant Proc., 28(2):540 (Apr. 1996).

Denning, C., et al., "Gene targeting in primary fetal fibroblasts from sheep and pig," Cloning Stem Cells, 3(4):221-231 (2001).

Denning, C., et al., "Deletion of the α(1,3)galactosyl transferase (GGTA1) gene and the prion protein (PrP) gene in sheep," Nature Biotechnology, 19:559-562 (Jun. 2001).

Fabre, J.W., "Nudging xenotransplantation towards humans," Nature Med., 1(5):403-404 (May 1995).

Galili, U., "The α-gal epitope (Galα-3Galβ-4GlcNAc-R) in xenotransplantation," Biochimie, 83:557-563 (2001).

Galili, U., et al., "Evolution and pathophysiology of the human natural anti-alpha-galactosyl IgG (anti-Gal) antibody," Springer Semin. Immunopathol., 15(2-3):155-171 (1993).

Galili, U., et al., "Evolutionary relationship between the natural anti-Gal antibody and the Gal alpha 1—3Gal epitope in primates," Proc. Natl. Acad. Sci., U S A., 84(5):1369-1373 (Mar. 1987).

Galili, U., et al., "Human natural anti-alpha-galactosyl IgG. II. The specific recognition of alpha (1—3)-linked galactose residues," J. Exp. Med., 162(2):573-582 (Aug. 1, 1985).

Galili, U., et al., "Man, apes, and old world monkeys differ from other mammals in the expression of α-galactosyl epitopes on nucleated cells," J.Biol.Chem., 263(33):17755-17762 (Nov. 25, 1988).

Gassmann, M., et al., "Maintenance of an extrachromosomal plasmid vector in mouse embryonic stem cells," Proc. Natl. Acad. Sci. USA, 92(5):1292-1296 (Feb. 28, 1995).

Gastinel, L.N., et al., "Bovine α1,3-galactosyltransferase catalytic domain structure and its relation-ship with ABO histo-blood group and glycosphingolipid glycosyltransferases," EMBO Journal, 20(4):638-649 (2001).

Hammer, R.E., et al., " Production of transgenic rabbits, sheep and pigs by microinjection," Nature, 315(6021):680-683 (Jun. 20-26, 1985).

Hancock, W., "Hyde Park Speakers Corner: Xeno-stagnation," AST Newsletter, 6(3):31-33 (Summer 1999) (American Society of Transplantation, Moorestown, NJ) (also published at http://www.a-s-t.org/library/newsArchive/vol6-3/hydepark.htm).

Harduin-Lepers, A., et al., "Characterization of two cis-regulatory regions in the murine beta 1,4-galactosyltransferase gene. Evidence for a negative regulatory element that controls initiation at the proximal site," J. Biol. Chem., 268(19):14348-14359 (Jul. 5, 1993).

Harrison, S.J., et al., "Efficient generation of α(1,3) galactosyltransferase knockout porcine fetal. fibroblasts for nuclear transfer," Transgenics Research, 11:143-150 (2002).

Hasty, P., et al., "The length of homology required for gene targeting in embryonic stem cells," Mol. Cell Biol.,11(11):5586-5591 (Nov. 1991).

Hayashi, S., et al., "Adenovirus-mediated gene transfer of antisense ribozyme for alpha (1,3)galactosyltransferase gene and alpha (1,2)fucosyltransferase gene in xenotransplantation," Transplant Proc., 29(4):2213 (Jun. 1997).

Hennet, T., "The galatoxyltransferase family," Cell. Mol. Life Sci., 59:1081-1095 (2002).

Joyner, A.L., "Production of a mutation in mouse En-2 gene by homologous recombination in embryonic stem cells," Nature, 338(6211)::153-156 (Mar. 9, 1989).

Joziasse, D.H., et al., "Bovine α1→3-galactosyltransferase: Isolation and characterization of a cDNA clone: Identification of homologous sequences in human genomic DNA,"J. Biol. Chem.,264(24):14290-14297 (Aug. 25, 1989).

Joziasse, D.H., et al., "Characterization of an α1→3-galactosyltransferase homologue on human chromosome 12 that is organized as a processed pseudogene," The Journal of Biological Chemistry, 266(11):6991-6998 (Apr. 15, 1991).

Joziasse, D.H., et al., "Murine α1→3-galactosyltransferase: A single gene locus specifies four isoforms of the enzyme by alternative splicing," J. Biol. Chem., 267(8) 5534-5541 (Mar. 15, 1992).

Joziasse, D.H., et al., "Xenotransplantation: the importance of the Galalpha1,3Gal epitope in hyperacute vascular rejection," Biochim. Biophys. Acta, 1455(2-3):403-418 (Oct. 8, 1999).

Just, I., et al., "The low molecular mass GTP-binding protein rho is affected by toxin A from Clostridium difficile," J. Clin. Invest., 95:1026-1031 (1995).

Katayama, A., et al., "Porcine α-1,3-galactosyltransferase: full length cDNA cloning, genomic organization, and analysis of splicing variants," Glycoconjugate Journal, 15:583-589 (1998).

Kelly, R.J., et al., "Sequence and expression of a candidate for the human Secretor blood group alpha (1,2)fucosyltransferase gene (FUT2). Homozygosity for an enzyme-inactivating nonsense mutation commonly correlates with the non-secretor phenotype,"*J. Biol. Chem.*, 270(9):4640-4649 (Mar. 3, 1995).

Kilby, N.J., et al., "Site-specific recombinases: tools for genome engineering," *Trends in Genetics*, 9(12):413-421 (Dec. 1993).

Koike, C., et al., "Comparison of the regulatory regions of the of α1,3galactosyltransferase gene between murine and porcine species," *Transplantation Proceedings*, 33:710-711 (2001).

Koike, C., et al., "Direct gene replacement of the mouse α(1,3)-galactosyltransferase gene with human α(1,2)-fucosyltransferase gene: Converting α-galactosyl epitopes into H antigens," *Xenotransplantation*, 4:147-153 (1997).

Koike, C., et al., "Introduction of α(1,2)-fucosyltransferase and its effect on α-Gal epitopes in transgenic pig," *Xenotransplantation*, 3:81-86 (1996).

Koike, C., et al., "Isolation of the regulatory regions and genomic organization of the porcine α1,3-galactosyltransferase gene," *Transplantation*, 70(9):1275-1283 (Nov. 15, 2000).

Koike, C., et al., "Molecular basis of evolutionary loss of the α1,3-galactosyltransferase gene in higher primates," *J. Biol. Chem.*, 277(12):10114-101120 (Mar. 22, 2002).

Lai, L., et al., "Production of α -1,3-galactosyltransferase knockout pigs by nuclear transfer cloning," *Science* 295:1089-1092 (Feb. 8, 2002) and supplementary data, *Science Express*, Jan. 3, 2002.

Larsen, R.D., et al., "Frameshift and nonsense mutations in a human genomic sequence homologous to a murine UDP-Gal:beta-D-Gal(1,4)-D-GlcNAc alpha(1,3)-galactosyltransferase cDNA," *J. Biol. Chem.*,265(12):7055-7061 (Apr. 25, 1990).

Larsen, R.D., et al., "Isolation of a cDNA encoding a murine UDPgalactose:beta-D-galactosyl- 1,4-N-acetyl-D-glucosaminide alpha-1,3-galactosyltransferase: expression cloning by gene transfer," *Proc. Natl. Acad. Sci., U S A.*, 86(21):8227-8231 (Nov. 1989).

Larsen, R.D., et al., "Molecular cloning, sequence, and expression of a human GDP-L-fucose:beta-D-galactoside 2-alpha-L-fucosyltransferase cDNA that can form the H blood group antigen," *Proc. Natl. Acad. Sci., U S A.*, 87(17):6674-6678 (Sep. 1990).

Lo, N.W., et al., "Transcription of the beta-galactoside alpha 2,6-sialyltransferase gene in B lymphocytes is directed by a separate and distinct promoter," *Glycobiology*, 6(3):271-279 (Apr. 1996).

Luckow, V.A., et al., "Trends in the development of baculovirus expression vector," *Bio/Technology*, 6:47-55 (Jan. 1988).

Mansour, S.L., et al., "Disruption of the proto-oncogene int-2 in mouse embryo-derived stem cells: a general strategy for targeting mutations to non-selectable genes,"*Nature*, 336(6197:348-352 (Nov. 24, 1988).

McCarrick, J.W. 3rd, et al., "Positive-negative selection gene targeting with the diphtheria toxin A-chain gene in mouse embryonic stem cells," *Transgenic Res.*, 2(4):183-190 (Jul. 2, 1993).

McCreath, K.J., et al., "Production of gene-targeted sheep by nuclear transfer from somatic cells," *Nature*, 405:1066-1069 (Jul. 29, 2000).

McCurry, K.R., et al.,"Human complement regulatory proteins protect swine-to-primate cardiac xenografts from humoral injury," *Nature Med.* 1(5):423-427 (May 1995).

McKenzie, I.F., et al., "Strategies to overcome the anti-Gal alpha (1-3)Gal reaction in xenotransplantation," *Transplant Proc.*, 28(2):537 (Apr. 1996).

Miyagawa, S., et al., "Remodeling of the major pig xenoantigen by N-acetylglucosaminyltransfer-ase III in transgenic pig," *J. Biol. Chem.*, 276(42):39310-39319 (Oct. 19, 2001).

Moreadith, R.W., et al., "Gene targeting in embryonic stem cells: the new physiology and metabolism,"*J. Mol. Med.*, 75(3):208-216 (Mar. 1997).

Mueller, S., et al., "Chimeric pigs following blastocyst injection of transgenic porcine primordial germ cells," *Mol. Reprod. Dev.*, 54(3):244-254 (Nov. 1999).

Mullins, L.J., et al., "Transgenesis in the rat and larger mammals," *J. Clin. Invest.*, 97(7):1557-1560 (Apr. 1, 1996).

Nagasaka, T., et al., "Inhibitory effect of α(1,2) fucosyltransferase recombinant adenoviral vector on αGal expression," *Transplantation Proceedings*, 30:3837-3838 (1998).

Onishi, A., et al., "Pig cloning by microinjection of fetal fibroblast nuclei," *Science*, 289:1188-1190 (Aug. 18, 2000).

Osman, N., et al., "Combined transgenic expression of alpha-galactosidase and alpha1,2-fucosyltransferase leads to optimal reduction in the major xenoepitope Galalpha(1,3)Gal," *Proc. Natl. Acad. Sci. U S A.*, 94(26):14677-14682 (Dec. 23, 1997).

Pera, M.F., et al., "Human embryonic stem cells," *J. Cell. Sci.*, 113 (Pt 1):5-10 (Jan. 2000).

Phelps, C.J., et al., "Production of α1,3-galactosyltransferase-deficient pigs," *Science*, 299:411-414 (Jan. 17, 2003).

Polejaeva, I.A., "Cloning pigs: advances and applications," *Reprod.*, 58 (Suppl.):293-300 (2001).

Polejaeva, I.A., et al., "Cloned pigs produced by nuclear transfer from adult somatic cells," *Nature*, 407:86-90 (Sep. 7, 2000).

Porter, A.C.G., et al., "Gene Targeting: Techniques and applications to transplantation," *Transplantation*, 64:1227-1235 (Nov. 15, 1997).

Pray, L., "Refining transgenic mice," *The Scientist* 16(13):34 (Jun. 24, 2002) [http://www.the-scientist.com/yr2002/jun/profile2_020624.html].

Pursel V.G., et al., "Progress on gene transfer in farm animals," *Vet. Immunol. Immunopathol.*, 17(1-4):303-312 (Dec. 1987).

Ramsoondar, J.J., et al., "Production of α1,3-galactosyltransferase-knockout cloned pigs expressing human α1,2-fucosyltransferase," *Biol. of Reproduction*, 69:437-445 (online before print Apr. 2, 2003).

Rexroad, C.E. Jr., et al., "Production of transgenic sheep with growth-regulating genes," *Mol. Reprod. Dev.*, 1(3):164-169 (1989).

Rexroad, C.E. Jr., et al., "Insertion, expression and physiology of growth-regulating genes in ruminants," *J. Reprod. Fert.*, 41(Suppl.):119-124 (1990).

Rubnitz, J., et al., "The minimum amount of homology required for homologous recombination in mammalian cells," *Mol. Cell. Biol.*, 4(11):2253-2258 (Nov. 1984).

Sandrin, M.S., et al., Identification of Gal(α1,3)Gal as the major epitope for pig-to-human vascularized xenografts, *Transplant Rev.*, 8(3):134-139 (Jul. 1994).

Sandrin, M.S., et al., "Characterization of cDNA clones for porcine α(1,3)galactosyl transferase: The enzyme generating the Galα(1,3)Gal epitope," *Xenotransplantation*, 1:81-88 (1994).

Sao, H., et al., "A new marrow T cell depletion method using anti-CD6 mnoclonal antibody-conjugated magnetic beads and its clinical application for prevention of acute graft-vs.-host disease in allogenic bone marrow transplantation: Rrsults of a phase I-II trial," *Intl. J. Hematol.*, 69(1):27-35 (Jan. 1999).

Sasaki, K., et al., "Expression cloning of a novel Gal beta (1-3/1-4) GlcNAc alpha 2,3-sialyl-transferase using lectin resistance selection," *J. Biol. Chem.*, 268(30):22782-22787 (Oct. 25, 1993).

Shaper, N.L., et al., "Characterization of the full length cDNA for murine beta-1,4-galactosyltransferase. Novel features at the 5'-end predict two translational start sites at two in-frame AUGs," *J. Biol. Chem.*, 263(21):10420-10428 (Jul. 25, 1988).

Sharma, A., et al., "Pig cells that lack the gene for α1,3-galactosyltransferase express low levels of the gal antigen," *Transplantation*, 75(4):430-436 (Feb. 7, 2003).

Simons, J.P., et al., "Gene transfer into sheep," *Bio/Technology*, 6(1):179-183 (Jan. 1988).

Smith, C.M., "Technical knockout: Gene-targeting strategies provide an avenue for studying gene function,"*The Scientist*,14(15):32 (Jul. 24, 2000) www.the-scientist.com/yr2000/jul/profile_000724.html.

Starzl, T.E., et al., "Antigen localization and migration in immunity and tolerance," *N. Engl. J. Med.*, 339(26):1905-1913 (Dec. 24, 1998).

Starzl, T.E., et al., "The biological basis of and strategies for clinical xenotransplantation," *Immunol. Rev.*, 141:213-244 (Oct. 1994).

Starzl, T.E., et al., "Will xenotransplantation ever be feasible?"*J. Am. Coll. Surg.*, 186(4):383-387 (Apr. 1998).

Stolberg, S.G., "Could this pig save your life?" *N. Y. Times Magazine.*, Oct. 3, 1999, pp. 46-51.

Stone, K.R., et al., "Porcine and bovine cartilage transplants in cynomolgus monkey," *Transplantation*, 63(5):640-645 (Mar. 15, 1997).

Strahan, K., et al., "Pig alpha1,3-galactosyltransferase: A major target for genetic manipulation in xenotransplantation," *Frontiers in Bioscience*, 1:e34-41 (Jul. 1, 1996) [www.bioscience.org/1996/v1/e/strahan1/htmls/34-41.htm].

Strahan, K.M., et al., "cDNA sequence and chromosome localization of pig alpha 1,3 galactosyltransferase," *Immunogenetics*, 41(2-3):101-105 (1995).

Strahan, K.M., et al., "Pig alpha 1, 3galactosyltransferase: sequence of a full-length cDNA clone, chromosomal localisation of the corresponding gene, and inhibition of expression in cultured pig endothelial cells," *Transplant Proc.*, 27(1):245-246 (Feb. 1995).

Svensson, E.C., et al., "Organization of the beta-galactoside alpha 2,6-sialyltransferase gene. Evidence for the transcriptional regulation of terminal glycosylation," *J. Biol. Chem..* 265(34):20863-20868 (Dec. 5, 1990).

Svensson, E.C., et al., "Regulated expression of alpha 2,6-sialyltransferase by the liver-enriched transcription factors HNF-1, DBP, and LAP," *J. Biol. Chem..*267(5):3466-3472 (Feb. 15, 1992).

Tanemura, M., et al., "Differential expression of the α-gal epitopes (Galα1-3Galβ1-4GlcNAc-R) on pig and mouse organs," *Transplantation*, 69(1):187-190 (Jan. 15, 2000).

Tanemura, M., et al., "Reduction of the major swine xenoantigen, the α-galactosyl epitope by transfection of the α2,3-sialyltransferase gene," *J..Biol.Chem.*, 273(26):16421-16425 (Jun. 26, 1998).

Tearle, R.G., et al., "The α-1,3-galactosyltransferase knockout mouse," *Transplantation*, 61(1):13-19 (Jan. 15, 1996).

Thall, A.D., et al., "Oocyte galα1,3gal epitopes implicated in sperm adhesion to the zona pellucida glycoprotein ZP3 are not required for fertilization in the mouse," *J. Biol. Chem.*, 270(27):21437-21440 (Sep. 15, 1995).

Thomas, K.R., et al., "Site-directed mutagenesis by gene targeting in mouse embryo-derived stem cells," *Cell*, 51(3):503-512 (Nov. 6, 1987).

Vanhove, B., et al., "Porcine α1,3-galactosyltransferase: Tissue-specific and regulated expression of splicing isoforms," *Biochim. Biophys. Acta*, 1356(1):1-11 (Mar. 27, 1997).

Vanhove, B., et al., "Transcriptional and posttranscriptional regulation of α1,3-galactosyltransfer-ase in activated endothelial cells results in decreased expression of Galα1,3Gal," *Glycobiology*, 8(5):481-487 (May 1998).

Vanhove, B., et al., "Variability of alpha 1,3-galactosyltransferase splicing isoforms in pig tissues," *Transplant Proc.* 28(2):622-623 (Apr. 1996).

Vaughan, H.A., et al., "Gal alpha(1,3)Gal is the major xenoepitope expressed on pig endothelial cells recognized by naturally occurring cytotoxic human antibodies," *Transplantation*, 58(8):879-882 (Oct. 27, 1994).

Vize, P.D., et al., "Introduction of a porcine growth hormone fusion gene into transgenic pigs promotes growth," *J. Cell Sci.*,;90 ( Pt 2):295-300 (Jun. 1988).

Wagner, "Development of transgenic pigs," *J. Cellular Biochem.*, 13B (Suppl.):164 (1989) (Abstract).

Weinstein, J., et al., "Primary structure of beta-galactoside alpha 2,6-sialyltransferase. Conversion of membrane-bound enzyme to soluble forms by cleavage of the NH2-terminal signal anchor," *J. Biol. Chem.*, 262(36):17735-17743 (Dec. 25, 1987).

White, D.J.G., et al., "Expression of human decay accelerating factor or membrane cofactor protein genes on mouse cells inhibits lysis by human complement," *Transplant International*, 5(Suppl. 1):S648-S650 (1992).

Yamamoto, F.-I., et al., "Genomic organization of human histo-blood group ABO genes," *Glycobiology*, 5(1):51-58 (1995).

Ye, Y., et al., "Evidence that intravenously administered a-galactosyl carbohydrates reduce baboon serum cytotoxicity to pig kidney cells (PK15) and transplanted pig hearts," *Transplantation*, 58(3):330-337 (Aug. 15, 1994).

Yarema, K.J., and Bertozzi, C.R., "Characterizing glycosylation pathways," *Genome Biology*, 2(5):1-10 (2001) REVIEWS0004 (Epublication May 1, 2001).

Castagliuolo, I., et al., "Clostridium difficile toxin A carboxyl-terminus peptide lacking ADP-ribosyltransferase activity acts as a mucosal adjuvant," *Infect. Immun.*, 72(5):2827-2836 (May 2004).

Weiss, "Clinical Review: Science, Medicine, and the Future: Xenotransplantation," BMJ, Oct. 3, 1998, vol. 317, pp. 931-934.

Konakci et al., "Alpha-Gal on Bioprostheses: Xenograft Immune Response in Cardiac Surgery," European Journal of Clinical Investigation, 2005, vol. 35, Blackwell Publishing Ltd., pp. 17-23.

Badylak, "Xenogenic Extracellular Matrix as a Scaffold for Tissue Reconstruction," Transplant Immunology, 2004, vol. 12, Elsevier B.V., pp. 367-377.

Chen et al., "Transgenic Porcine Valves Show No Signs of Delayed Cardiac Xenograft Rejection," The Annals of Thoracic Surgery, 2001, vol. 71, Elsevier Science Inc., pp. S389-S392.

\* cited by examiner

Figure 2

|  | Exon 8 | | Exon 9 → | | | | |
|---|---|---|---|---|---|---|---|
| | | | Tyr | Ile | Glu | His | Tyr (SEQ ID NO: 3) |
| Wild type | gct gtc gga ag A | | TAC | ATT | GAG | CAT | TAC |
| | (SEQ ID NO: 1) | | (SEQ ID NO: 2) | | | | |

|  | Exon 8 | | Exon 9 → | | | | |
|---|---|---|---|---|---|---|---|
| | | | Asp | Ile | Glu | His | Tyr (SEQ ID NO: 5) |
| Mutation | gct gtc gga ag A | | GAC | ATT | GAG | CAT | TAC |
| | (SEQ ID NO: 1) | | (SEQ ID NO: 4) | | | | |

TISSUE PRODUCTS DERIVED FROM PORCINE ANIMALS LACKING ANY EXPRESSION OF FUNCTIONAL ALPHA 1,3 GALACTOSYLTRANSFERASE

This application is a continuation-in-part of U.S. patent application Ser. No. 10/646,970, filed on Aug. 21, 2003, now U.S. Pat. No. 7,795,493, which claims priority to U.S. Provisional Patent Application No. 60/404,775, filed Aug. 21, 2002. This application also claims priority to U.S. Provisional Patent Application No. 60/553,895, filed on Mar. 17, 2004 and U.S. Provisional Patent Application No. 60/559,816, filed on Apr. 6, 2004.

FIELD OF THE INVENTION

The present invention provides tissues derived from animals which lack any expression of functional alpha 1,3 galactosyltransferase (alpha1,3GT). Such tissues can be used in the field of xenotransplantations, such as orthopedic reconstruction and repair, skin repair and internal tissue repair, or as medical devices.

BACKGROUND OF THE INVENTION

Ruminant animals, such as porcine, ovine and bovine, are considered likely sources of xenograft organs and tissues. Porcine xenografts have been given the most attention since the supply of pigs is plentiful, breeding programs are well established, and their size and physiology are compatible with humans. Other ruminant sources, such as bovine or ovine have also been suggested as a source for hard and soft tissue xenografts. However, there are several obstacles that must be overcome before the transfer of these organs or tissues into humans can be successful. The most significant is immune rejection. The first immunological hurdle is "hyperacute rejection" (HAR). HAR is defined by the ubiquitous presence of high titers of pre-formed natural antibodies binding to the foreign tissue. The binding of these natural antibodies to target epitopes on the donor tissue endothelium is believed to be the initiating event in HAR. This binding, within minutes of perfusion of the donor tissue with the recipient blood, is followed by complement activation, platelet and fibrin deposition, and ultimately by interstitial edema and hemorrhage in the donor organ, all of which cause rejection of the tissue in the recipient (Strahan et al. (1996) Frontiers in Bioscience 1, e34-41).

The most frequently transplanted tissue in humans is bone (J. M. Lane et al. Current Approaches to Experimental Bone Grafting, 18 Orthopedic Clinics of North America (2) 213 (1987)). In the United States alone more than 100,000 bone graft or implant procedures are performed every year to repair or replace osseous defects resulting from trauma, infection, congenital malformation, or malignancy. Human bone is a hard connective tissue consisting of cells embedded in an extracellular matrix of mineralized ground substance and collagen fibers (Stedman's Medical Dictionary, Williams & Wilkins, Baltimore, Md. (1995)).

Bone grafts and implants are often formed of autologous bone. However, transplantable autologous bone tissue for large defects, particularly in children, is often unavailable. In addition, autologous bone transplantation may result in post-operative morbidity such as pain, hemorrhage, wound problems, cosmetic disability, infection or nerve damage at the donor site. Further, difficulties in fabricating the desired functional shape from the transplanted autologous bone tissue can result in less than optimal filling of the bone defect.

Soft tissues, such as tendons, ligaments, cartilage, skin, heart tissue and valves, and submucosal tissues, are also commonly transplanted into humans. Much of the structure and many of the properties of the original tissue can be retained in transplants through use of xenograft materials. Xenograft tissue represents an unlimited supply of available material if it can be processed to be safe for transplantation in a human.

Once implanted in an individual, a xenograft provokes immunogenic reactions such as chronic and hyperacute rejection of the xenograft. Because of this rejection, bone xenografts exhibit increased rates of fracture, resorption and nonunion. The major immunological obstacle for the use of animal tissues, such as porcine, bovine or ovine, as implants in humans is the natural anti-galactose alpha 1,3-galactose antibody, which comprises approximately 1% of antibodies in humans and monkeys.

Except for Old World monkeys, apes and humans, most mammals carry glycoproteins on their cell surfaces that contain the galactose alpha 1,3-galactose epitope (Galili et al., J. Biol. Chem. 263: 17755-17762, 1988). In contrast, glycoproteins that contain galactose alpha 1,3-galactose are found in large amounts on cells of other mammals, such as pigs. Humans, apes and old world monkeys do not have a galactose alpha 1,3-galactose and have a naturally occurring anti-galactose alpha 1,3-galactose antibody that is produced in high quantity (Cooper et al., Lancet 342:682-683, 1993). It binds specifically to glycoproteins and glycolipids bearing galactose alpha-1,3 galactose.

This differential distribution of the "alpha-1,3 GT epitope" and anti-Gal antibodies (i.e., antibodies binding to glycoproteins and glycolipids bearing galactose alpha-1,3 galactose) in mammals is the result of an evolutionary process which selected for species with inactivated (i.e. mutated) alpha-1,3-galactosyltransferase in ancestral Old World primates and humans. Thus, humans are "natural knockouts" of alpha-1,3-GT. A direct outcome of this event is the rejection of xenografts, such as the rejection of pig organs transplanted into humans initially via HAR.

A variety of strategies have been implemented to eliminate or modulate the anti-Gal humoral response caused by porcine xenotransplantation, including enzymatic removal of the epitope with alpha-galactosidases (Stone et al., Transplantation 63: 640-645, 1997), specific anti-gal antibody removal (Ye et al., Transplantation 58: 330-337, 1994), capping of the epitope with other carbohydrate moieties, which failed to eliminate alpha-1,3-GT expression (Tanemura et al., J. Biol. Chem. 27321: 16421-16425, 1998 and Koike et al., Xenotransplantation 4: 147-153, 1997) and the introduction of complement inhibitory proteins (Dalmasso et al., Clin. Exp. Immunol. 86: 31-35, 1991, Dalmasso et al. Transplantation 52:530-533 (1991)). Costa et al. (FASEB J 13, 1762 (1999)) reported that competitive inhibition of alpha-1,3-GT in H-transferase transgenic pigs results in only partial reduction in epitope numbers. Similarly, Miyagawa et al. (J. Biol. Chem 276, 39310 (2001)) reported that attempts to block expression of gal epitopes in N-acetylglucosaminyltransferase III transgenic pigs also resulted in only partial reduction of gal epitopes numbers and failed to significantly extend graft survival in primate recipients.

Badylak et. al. developed a process to isolate submucosa tissue from the small intestine of pigs for use in a variety of tissue grafts including connective tissue grafts to repair knee ligaments (anterior cruciate ligament) and shoulder rotator cuff repair. The small intestine submucosa (SIS) material is treated using chemical and enzymatic steps to strip the tissue of viable cells, leaving an acellular extracellular matrix that encourages in-growth of host cells and tissue regeneration (see, for example, U.S. Pat. Nos. 4,902,508, 4,956,178, and 5,372,821). This process is currently utilized for human tissue grafts. However, despite the chemical treatment steps, galactose alpha 1,3 galactose sugar residues remain embedded in the graft and cause immune activation and inflammation in human patients (Allman et al., 2001, Transplantation 71, 1631-1640; Mcpherson et al., 2000, Tissue Engineering 6(3), 233-239).

Stone et al. developed a process to treat porcine soft tissue and bone tissue to remove cellular material followed by treatment with alpha-galactosylsidase to remove the galactose alpha 1,3-galactose from the tissue prior to transplantation (Stone et al. Transplantation 1997: 63: 646-651; Stone et al. Transplantation 1998: 65:1577-83). This process has been the subject of numerous patent applications, which discuss the use of such tissue for a variety of applications, such as anterior cruciate ligament repair, meniscal repair, articular cartilage xenografts, submucosal xenografts, bone and bone matrix xenografts, heart valve replacement and soft tissue xenografts, see for example, U.S. Pat. Nos. 5,865,849, 5,913, 900, 5,984,858, 6,093,204, 6,267,786, 6,455,309, 6,683,732, 5,944,755, 6,110,206, 6,402,783, and 5,902,338; U.S. Patent Application Nos. 2002/0087211, 2001/0051828, 2001/0039459, 2003/0039678, 2003/0023304, and 2003/0097179; and PCT Publication Nos. WO 00/47131, WO 00/47132, WO 99/44533, WO 02/076337, WO 99/51170, WO 99/47080, WO 03/097809, WO 02/089711, WO 01/91671, and WO 03/105737.

Thus, there is a need in the art to provide tissue grafts that do not cause deleterious effects in humans.

Costa et al. (FASEB (2003) 17: 109-111) reported that the delayed rejection of porcine cartilage transplanted into wild-type and α-1,3-galactosyltransferase knockout mice is reduced by transgenic expression of α1,2-fucosyltransferase (HT transgenic) in the cartilage.

Single allele knockouts of the alpha-1,3-GT locus in porcine cells and live animals have been reported. Denning et al. (Nature Biotechnology 19: 559-562, 2001) reported the targeted gene deletion of one allele of the alpha-1,3-GT gene in sheep. Harrison et al. (Transgenics Research 11: 143-150, 2002) reported the production of heterozygous alpha-1,3-GT knock out somatic porcine fetal fibroblasts cells. In 2002, Lai et al. (Science 295: 1089-1092, 2002) and Dai et al. (Nature Biotechnology 20: 251-255, 2002) reported the production of pigs, in which one allele of the alpha-1,3-GT gene was successfully rendered inactive. Ramsoondar et al. (Biol of Reproduc 69, 437-445 (2003)) reported the generation of heterozygous alpha-1,3-GT knockout pigs that also express human alpha-1,2-fucosyltransferase (HT), which expressed both the HT and alpha-1,3-GT epitopes.

PCT publication No. WO 94/21799 and U.S. Pat. No. 5,821,117 to the Austin Research Institute; PCT publication No. WO 95/20661 to Bresatec; and PCT publication No. WO 95/28412, U.S. Pat. No. 6,153,428, U.S. Pat. No. 6,413,769 and US publication No. 2003/0014770 to BioTransplant, Inc. and The General Hospital Corporation provide a discussion of the production of alpha-1,3-GT negative porcine cells based on knowledge of the cDNA of the alpha-1,3-GT gene (and without knowledge of the genomic organization or sequence). However, there was no evidence that such cells were actually produced prior to the filing date of these applications and the examples were all prophetic.

The first public disclosure of the successful production of a heterozygous alpha-1,3-GT negative porcine cell occurred in July 1999 at the Lake Tahoe Transgenic Animal Conference (David Ayares, PPL Therapeutics, Inc., "Gene Targeting in Livestock", Transgenic Animal Research Cinference, July 1999, Abstract, pg. 20; Ayares, IBS News Report, November 1999: 5-6). Until recently, no one had published or publicly disclosed the production of a homozygous alpha 1,3GT negative porcine cell. Further, since porcine embryonic stem cells have not been available to date, there was and still is no way to use an alpha-1,3-GT homogygous embryonic stem cell to attempt to prepare a live homogygous alpha1,3GT knock out pig.

On Feb. 27, 2003, Sharma et al. (Transplantation 75:430-436 (2003) published a report demonstrating a successful production of fetal pig fibroblast cells homozygous for the knockout of the alpha-1,3-GT gene.

PCT publication No. WO 00/51424 to PPL Therapeutics describes the genetic modification of somatic cells for nuclear transfer. This patent application discloses the genetic disruption of the alpha-1,3-GT gene in porcine somatic cells, and the subsequent use of the nucleus of these cells lacking at least one copy of the alpha-1,3-GT gene for nuclear transfer.

U.S. Pat. No. 6,331,658 to Cooper & Koren claims but does not confirm any actual production of genetically engineered mammals that express a sialyltransferase or a fucosyltransferase protein. The patent asserts that the genetically engineered mammals would exhibit a reduction of galactosylated protein epitopes on the cell surface of the mammal.

PCT publication No. WO 03/055302 to The Curators of the University of Missouri confirms the production of heterozygous alpha 1,3GT knockout miniature swine for use in xenotransplantation. This application is generally directed to a knockout swine that includes a disrupted alpha-1,3-GT gene, wherein expression of functional alpha-1,3-GT in the knockout swine is decreased as compared to the wildtype. This application does not provide any guidance as to what extent the alpha-1,3-GT must be decreased such that the swine is useful for xenotransplantation. Further, this application does not provide any proof that the heterozygous pigs that were produced exhibited a decreased expression of functional alpha1,3GT. Further, while the application refers to homozygous alpha 1,3GT knockout swine, there is no evidence in the application that any were actually produced or producible, much less whether the resultant offspring would be viable or phenotypically useful for xenotransplantation.

Total depletion of the glycoproteins that contain galactose alpha 1,3-galactose is clearly the best approach for the production of porcine animals for xenotransplantation. It is theoretically possible that double knockouts, or the disruption of both copies of the alpha 1,3GT gene, could be produced by two methods: 1) breeding of two single allele knockout animals to produce progeny, in which case, one would predict based on Mendelian genetics that one in four should be double knockouts or 2) genetic modification of the second allele in a cell with a pre-existing single knockout. In fact, this has been quite difficult as illustrated by the fact that while the first patent application on knock-out porcine cells was filed in 1993, the first homozygous alpha 1,3GT knock out pig was not produced until July 2002 (described herein).

Transgenic mice (not pigs) have historically been the preferred model to study the effects of genetic modifications on mammalian physiology, for a number of reasons, not the least of which is that mouse embryonic stem cells have been available while porcine embryonic stem cells have not been available. Mice are ideal animals for basic research applications because they are relatively easy to handle, they reproduce rapidly, and they can be genetically manipulated at the molecular level. Scientists use the mouse models to study the molecular pathologies of a variety of genetically based diseases, from colon cancer to mental retardation. Thousands of genetically modified mice have been created to date. A "Mouse Knockout and Mutation Database" has been created by BioMedNet to provide a comprehensive database of phenotypic and genotypic information on mouse knockouts and classical mutations (http://research.bmn.com/mkmd; Brandon et al Current Biology 5[7]:758-765 (1995); Brandon et al Current Biology 5[8]:873-881 (1995)), this database provides information on over 3,000 unique genes, which have been targeted in the mouse genome to date.

Based on this extensive experience with mice, it has been learned that transgenic technology has some significant limitations. Because of developmental defects, many genetically modified mice, especially null mice created by gene knock out technology die as embryos before the researcher has a chance to use the model for experimentation. Even if the mice survive, they can develop significantly altered phenotypes, which can render them severely disabled, deformed or debilitated (Pray, Leslie, The Scientist 16 [13]: 34 (2002); Smith, The Scientist 14[15]:32, (2000); Brandon et al Current Biology 5[6]:625-634 (1995); Brandon et al Current Biology 5[7]:758-765 (1995); Brandon et al Current Biology 5[8]: 873-881 (1995); http://research.bmn.com/mkmd). Further, it has been learned that it is not possible to predict whether or not a given gene plays a critical role in the development of the organism, and, thus, whether elimination of the gene will result in a lethal or altered phenotype, until the knockout has been successfully created and viable offspring are produced.

Mice have been genetically modified to eliminate functional alpha-1,3-GT expression. Double-knockout alpha-1,3-GT mice have been produced. They are developmentally viable and have normal organs (Thall et al. J Biol Chem 270:21437-40 (1995); Tearle et al. Transplantation 61:13-19 (1996), see also U.S. Pat. No. 5,849,991). However, two phenotypic abnormalities in these mice were apparent. First, all mice develop dense cortical cataracts. Second, the elimination of both alleles of the alpha-1,3-GT gene significantly affected the development of the mice. The mating of mice heterozygous for the alpha-1,3-GT gene produced genotype ratios that deviated significantly from the predicted Mendelian 1:2:1 ratio (Tearle et al. Transplantation 61:13-19 (1996)).

Pigs have a level of cell surface glycoproteins containing galactose alpha 1,3-galactose that is 100-1000 fold higher than found in mice. (Sharma et al. Transplantation 75:430-436 (2003); Galili et al. Transplantation 69:187-190 (2000)). Thus, alpha 1,3-GT activity is more critical and more abundant in the pig than the mouse.

Despite predictions and prophetic statements, no one knew whether the disruption of both alleles of the alpha-1,3-GT gene would be lethal or would effect porcine development or result in an altered phenotype (Ayares et al. Graft 4(1)80-85 (2001); Sharma et al. Transplantation 75:430-436 (2003); Porter & Dallman Transplantation 64:1227-1235 (1997); Galili, U. Biochimie 83:557-563 (2001)). Indeed, many experts in the field expressed serious doubts as to whether homozygous alpha-1,3-GT knockout pigs would be viable at all, much less develop normally. Thus, until a viable double alpha-1,3-GT knockout pig is produced, according to those of skill in the art at the time, it was not possible to determine (i) whether the offspring would be viable or (ii) whether the offspring would display a phenotype that allows the use of the organs for transplantation into humans.

Such concerns were expressed until a double knockout pig was produced. In 2003, Phelps et al. (Science 299:411-414 (2003)) reported the production of the first live pigs lacking any functional expression of alpha 1,3 galactosyltransferase, which represented a major breakthrough in xenotransplantation.

PCT publication No. WO 04/028243 filed by Revivicor, Inc. describes the successful production of viable pigs, as well as organs, cells and tissues derived therefrom, lacking any functional expression of alpha 1,3 galactosyltransferase. PCT Publication No. WO 04/016742 filed by Immerge Biotherapeutics, Inc. also describes the production of alpha 1,3 galactosyltransferase knock-out pigs.

It is therefore an object of the present invention to provide tissue products that can be transplanted into humans without causing significant rejection.

It is another object of the present invention to provide tissues from animals for use in orthopedic reconstruction and repair, skin repair and internal tissue repair in humans.

SUMMARY OF THE INVENTION

The present invention is tissue products from animals lacking any expression of functional alpha-1,3-galactosyltransferase for use as xenografts. The tissue can be hard tissue, such as bone, or soft tissue, such as dermal. This hard and soft tissue can be used as a prosthesis, for example, for use in orthopedic reconstruction and repair, skin repair and/or internal tissue repair. The animal can be a ruminant or an ungulate, such as a bovine, porcine or ovine. In a specific embodiment, the animal is a pig. The tissues from animals lacking any functional expression of the alpha-1,3-GT gene can be obtained from a prenatal, neonatal, immature, or fully mature animal, such as a porcine, bovine or ovine. The tissues can be prepared according to the methods described herein for use in animal, such as human, tissue repair.

In embodiments of the present invention, tissues are provided in which both alleles of the alpha-1,3-GT gene are rendered inactive, such that the resultant alpha-1,3-GT enzyme can no longer generate galactose alpha1,3-galactose on the cell surface. In one embodiment, the alpha-1,3-GT gene can be transcribed into RNA, but not translated into protein. In another embodiment, the alpha-1,3-GT gene can be transcribed in an inactive truncated form. Such a truncated RNA may either not be translated or can be translated into a nonfunctional protein. In an alternative embodiment, the alpha-1,3-GT gene can be inactivated in such a way that no transcription of the gene occurs.

In one aspect of the present invention, tissues are provided in which at least one allele of the alpha-1,3-GT gene is inactivated via a genetic targeting event. In another aspect of the present invention, tissues from animals are provided in which both alleles of the alpha-1,3-GT gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can also be inserted.

As one aspect of the invention, tissues from animals are provided that carry at least one point mutation in the alpha-1,3-GT gene. Such animals are free of antibiotic-resistance genes and thus have the potential to make a safer product for human use. Thus, another aspect of the invention is tissue from a homozygous alpha-1,3-GT knock out that has no antibiotic resistant or other selectable marker genes, such as neomycin, puromycin, hygromycin, zeocin, hisD, or blasticidin. In one embodiment, this point mutation can occur via a genetic targeting event. In another embodiment, this point mutation can be naturally occurring. In a further embodiment, mutations can be induced in the alpha-1,3-GT gene via a mutagenic agent. In one specific embodiment the point mutation can be a T-to-G mutation at the second base of exon 9 of the alpha-1,3-GT gene (see, FIG. 2; Phelps et al. Science 299:411-414 (2003)). In other embodiments, at least two, at least three, at least four, at least five, at least ten or at least twenty point mutations can exist to render the alpha-1,3-GT gene inactive. In other embodiments, tissues are provided in which both alleles of the alpha-1,3-GT gene contain point mutations that prevent any expression of functional alpha-1, 3-GT. In a specific embodiment, tissues are provided that contain the T-to-G mutation at the second base of exon 9 in both alleles of the alpha-1,3-GT gene. In a further embodiment, one allele is inactivated by a genetic targeting event and the other allele is inactivated due to presence of a T-to-G point mutation at the second base of exon 9 of the alpha-1,3-GT gene. In a specific embodiment, tissues from animals are provided in which one allele is inactivated via a targeting construct directed to Exon 9 and the other allele is inactivated due to presence of a T-to-G point mutation at the second base of exon 9 of the alpha-1,3-GT gene (see, FIG. 2; Phelps et al. Science 299:411-414 (2003)).

In a further embodiment, hard or soft tissue can be obtained from animals lacking any functional expression of the alpha-1,3-GT gene that also can contain additional genetic modifications. Such genetic modifications can include additions and/or deletions of other genes to prevent rejection, promote wound healing, and/or minimize or eliminate unwanted pathogens (such as, for example, prions or retroviruses).

In one embodiment, the tissue can be used in its "native" form (directly removed from the animal). Alternatively, the tissue can be subjected to further treatment or modification. In particular embodiments of the present invention, decellularized tissues are provided that are derived from the animals or tissues described herein. Other embodiments provide methods and processes to prepare and obtain the tissue from an animal that lacks any expression of functional alpha-1,3-galactosyltransferase.

In certain embodiment, processes to prepare tissue can include steps to strip away or kill all viable cells (decellularization) leaving behind only an acellular matrix or scaffold for use in tissue repair and remodeling, as well as, optionally, treatments for crosslinking and sterilization. In a particular embodiment, any decellularized hard or soft tissue is provided that is derived from the animals disclosed herein. In one embodiment, de-cellularized soft dermal tissue is provided. In another embodiment, de-cellularized submucosal tissue is provided. In other embodiment, such de-cellularized material can be less immunogenic. In further embodiments, such de-cellularized tissues can be used as a scaffolding or matrix to repair and/or reconstruct particular human body parts. In one embodiment, the decellularized tissue can be used for the repair of the following, incluing, but not limited to, hernia, abdominal wall, rotator ciff, cosmetic surgery or any other soft tissue defects known to one skilled in the art or disclosed herein. In particular embodiments, submucosal and or dermal decellularized material is provided.

The tissues and the animal source of the tissues can be further modified or treated to promote wound healing; minimize or eliminate unwanted pathogens, such as infectious disease transmission (such as prions and retroviruses); add growth factors to promote tissue remodeling, sterilize the tissue, and/or improve the biomechanical or physical properties of the tissue. Such treatments can be chemical, such as alcohol or peroxide treatment, mechanical or physical, such as enzymatic and/or exposure to a gas, ultra violet radiation, or gamma irradiation.

In another embodiment, the tissues from animals lacking any functional expression of the alpha-1,3-GT gene can be combined with other inert materials such as plastics, metals (including but not limited to stainless steel and titanium) in order to provide additional mechanical strength or for other benefits to the recipient patient.

In another embodiment, the tissues from animal lacking any functional expression of the alpha-1,3-GT gene can be used as a scaffold, which serves to recruit the recipient's cells to the site of the transplanted material. This scaffold can also contain extracellular matrix (ECM) components, such ECM components can optionally be derived from an animal lacking any functional expression of the alpha-1,3-GT gene. Alternatively, the tissue can be used as a complete tissue replacement, such that, for example, the transplanted tissue performs the same biomechanical functionality of the tissue it is replacing or repairing. In a further embodiment, the tissue can be pre-conditioned (chemically and/or mechanically) prior to transplantation to allow optimal range of motion of the tissue following transplantation, or to allow for a "custom fit" for the recipient, or to otherwise provide optimal biological or biomechanical properties.

In one embodiment of the present invention, the hard and soft tissue from animals lacking any expression of functional alpha-1,3-galactosyltransferase can be used in orthopedic reconstruction and repair. Such tissues include connective tissue, tendons, ligaments, muscle, cartilage, bone and bone derivatives. In one embodiment, the tissue can be used for knee repair, such as anterior cruciate ligament (ACL) or posterior cruciate ligament (PCL) replacement. In another embodiment, the tissue can be used for bone-tendon-bone grafts, rotator cuff repair or as suture plugs. Bone tissue can be used as whole or partial bone replacement, bone plugs, bone screws or bone chips (including preparations in which bone chips can be prepared as a paste). Bone tissue can also be used for periodontal applications or as spinal spacers.

In a further embodiment, the hard and soft tissue from animals lacking any expression of functional alpha-1,3-galactosyltransferase can be used in skin repair, for example, to repair deep tissue burns of the skin. Skin tissues include, but are not limited to, dermal or epidermal tissue or derivatives thereof.

In another aspect of the present invention, the hard and soft tissue from animals lacking any expression of functional alpha-1,3-galactosyltransferase can be used in internal tissue repair, such as abdominal wall repair, hernia repair, heart valve repair or replacement, cosmetic surgery/repair, maxilofacial repair, for repair of gynecological or urological tissues, and dura repair. Internal tissues include pericardial tissue, heart valves and submucosal tissue. In one embodiment, the submucosal tissue can be used to repair or replace connective tissue.

BRIEF DESCRIPTION OF THE DRAWINGS

FIG. 2 depicts a short segment of the coding region of the alpha-1,3-GT gene (see GenBank Acc. No. L36152) in which the point mutation selected by Toxin A occurs. Upper sequence occurs in wild type; lower sequence shows the change due to the point mutation in the second allele.

DETAILED DESCRIPTION

Figure 1:
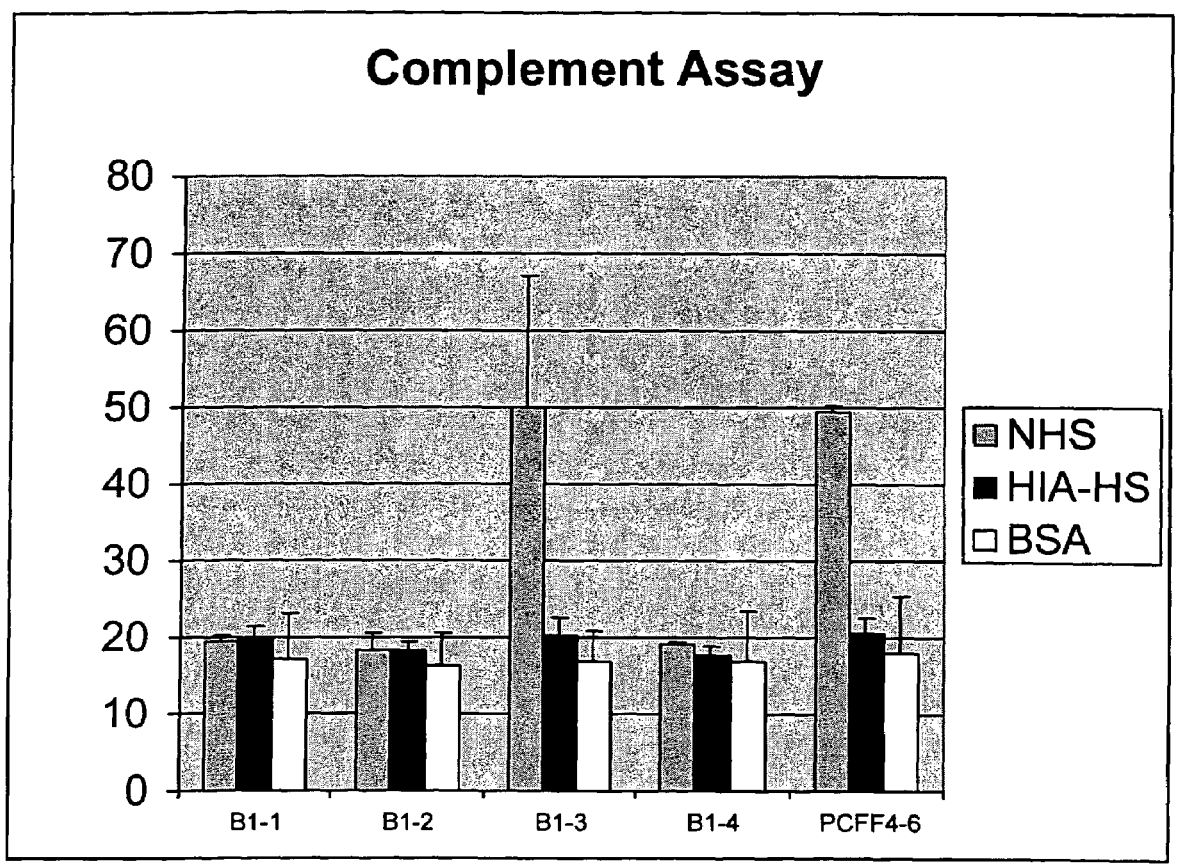
FIG. 1 is a graph depicting the relative lytic effects of complement on cells from fetuses 680B1-4.

The present invention is tissue products from animals lacking any expression of functional alpha-1,3-galactosyltransferase for use as xenografts. The tissue can be hard tissue, such as bone, or soft tissue, such as dermal. This hard and soft tissue can be used for xenotransplantation, such as orthopedic reconstruction and repair, skin repair and internal tissue repair. The animal can be a ruminant or an ungulate, such as a bovine, porcine or ovine. In specific embodiment, the animal is a pig. The tissues from animals lacking any functional expression of the alpha-1,3-GT gene can be obtained from a prenatal, neonatal, immature, or fully mature animal, such as a porcine, bovine or ovine.

In embodiments of the present invention, the alleles of the alpha-1,3-GT gene are rendered inactive, such that the resultant alpha-1,3-GT enzyme can no longer generate galactose alpha1,3-galactose on the cell surface.

The tissues from animals lacking any functional expression of the alpha-1,3-GT gene can be obtained from a prenatal, neonatal, immature, or fully mature animal, such as a porcine, bovine or ovine. In one embodiment, the tissue can be used in its "native" form (directly removed from the animal). Alternatively, the tissue can be subjected to further treatment or modification.

In one embodiment of the present invention, the hard and soft tissue from animals lacking any expression of functional alpha-1,3-galactosyltransferase can be used in orthopedic reconstruction and repair. In a further embodiment, the hard and soft tissue from animals lacking any expression of functional alpha-1,3-galactosyltransferase can be used in skin repair. In another aspect of the present invention, the hard and soft tissue from animals lacking any expression of functional alpha-1,3-galactosyltransferase can be used in internal tissue repair.

Definitions

As used herein, the term "animal" (as in "genetically modified (or altered) animal") is meant to include any non-human animal, particularly any non-human mammal, including but not limited to pigs, sheep, goats, cattle (bovine), deer, mules, horses, monkeys, dogs, cats, rats, mice, birds, chickens, reptiles, fish, and insects. In one embodiment of the invention, genetically altered pigs and methods of production thereof are provided.

As used herein, an "organ" is an organized structure, which can be made up of one or more tissues. An "organ" performs one or more specific biological functions. Organs include, without limitation, heart, liver, kidney, pancreas, lung, thyroid, and skin.

As used herein, a "tissue" is an organized structure comprising cells and the intracellular substances surrounding them. The "tissue" alone or in conjunction with other cells or tissues can perform one or more biological functions. The tissue can be hard or soft tissue. A "tissue product" includes a tissue and/or a tissue fragment or tissue derivative thereof as described herein. This "tissue product" can be used to replace or repair a human tissue. Such "tissue products" can be modified, such as, but not limited to de-cellularized, according to the methods described herein.

As used herein, the terms "porcine", "porcine animal", "pig" and "swine" are generic terms referring to the same type of animal without regard to gender, size, or breed.

As used herein the term prostheses or prosthetic device refers to a hard or soft tissue that has been crafted into an appropriate form for body repair. In one embodiment, the body being repaired can be a human body. In other embodiments, the mammal body parts can be repaired, for example, horses, dogs, cats or other domestic animals.

I. Types and Preparation of Tissue

The tissues from animal lacking any functional expression of the alpha-1,3-GT gene can be obtained from a prenatal, neonatal, immature, or fully mature animal, such as a porcine, bovine or ovine.

In one embodiment, the tissue can be used in its "native" form (directly removed from the animal). In an alternate embodiment, the tissue can be subjected to further treatment or modification. Tissues and the animal source of the tissues can be further modified or treated to promote wound healing; minimize or eliminate unwanted pathogens, such as infectious disease transmission (such as prions and retroviruses); add growth factors to promote tissue remodeling, sterilize the tissue, and/or improve the biomechanical or physical properties of the tissue.

In one embodiment, the type of treatment can be chemical, mechanical or physical, such as enzymatic and/or exposure to a gas, ethylene oxide treatment, propylene oxide treatment, gas plasma sterilization, peracetic acid sterilization, ultra violet radiation, or gamma irradiation. The methods of the invention, include, alone or in combination, treatment with radiation, one or more cycles of freezing and thawing, treatment with a chemical cross-linking agent, treatment with alcohol or ozonation. When more than one of these treatments is applied to the xenograft, the treatments may occur in any order.

In one embodiment, the xenograft tissue can be treated by exposure to ultraviolet radiation, for example, exposure to ultraviolet radiation for about fifteen minutes. In another embodiment, the tissue can be exposed to gamma radiation. The tissue can be exposed to gamma radiation in an amount of 0.5, 1.0, 1.5, 2.0, 2.5, 3.0, 3.5, 4.0, 4.5, 5.0, 7.0, 10, 15 or 20 MegaRad, or between about 0.5 to 3 or 1.5 to 2.0 MegaRad. In a further embodiment, the xenograft can be subjected to ozonation. In other embodiments, the tissue can be treated according to accepted standards for sterilization, see for example, American National Standard, ANSI/AAMI/ISO 11137-1994, Sterilization of health care products—Requirements for validation and routine control—Radiation sterilization, 1994, American National Standard, ANSI/AAMI ST32-1991, Guidelines for Gamma Radiation Sterilization, 1991, Scholla, M. H. and Wells, M. E. "Tracking Trends in Industrial Sterilization." Medical Device and Diagnostic Industry, September 1997, pp. 92-95, AAMI Recommended Practice—"Process Control Guidelines for Gamma Radiation Sterilization of Medical Devices," ISBN No. 0-910275-38-6, pp. 7-21, 1984, American National Standard, ANSI/AAMI/ISO 11137-1994, Sterilization of health care products—Requirements for validation and routine control—Radiation sterilization, 1994, American National Standard, ANSI/AAMI ST32-1991, Guideline for Gamma Radiation Sterilization, 1991, American National Standard, ANSI/AAMI ST31-1990, Guideline for Electron Beam Radiation Sterilization of Medical Devices, 1990, Genova, Hollis, Crowell and Schady, "A Procedure for Validating the Sterility of an Individual Gamma Radiation Sterilized Production Batch," Journal of Parenteral Science and Technology, Volume. 41, No. 1, pp. 33-36, January 1987, and Gaughran and Morrissey, "Sterilization of Medical Products," Volume 2, ISBN-0-919868-14-2, pp. 35-39, 1980.

In another embodiment, the xenograft tissue can be treated immersion in an alcohol solution. Any alcohol solution can be used to perform this treatment, including, but not limited to, primary alcohols, secondary alcohols, tertiary alcohols, polyols, higher order alcohols, aromatic alcohols, such as phenol, heteroaromatic alcohols, ethanol, methanol, propanol, methyl-propanol, isopropyl alcohol, 2-propanol, cyclobutanol, 1,2-ethanediol 4,4-dimethyl-2-pentanol, 4-penten-2-ol, 4-amino-3-isopropylhexanol 5-mercapto-2,4-cyclohexadienol. The alcohol solutions can be 10, 20, 30, 40, 45, 50, 55, 60, 65, 70, 75, 80, 85, 90, 95, 96, 97, 98, or 99% alcohol. For example, a 70% solution of isopropanol. The alcohol solution can be used at room temperature (such as approximately 20-30° C., or 25° C.) or at low temperatures (such as approximately 0-20° C.).

In a further embodiment, the xenograft tissue can be treated by freeze/thaw cycling. For example, the xenograft tissue can be frozen using any method of freezing. In one embodiment, the tissue is completely frozen, such that no interior warm spots remain which contain unfrozen tissue. In one embodiment, the xenograft tissue can be immersed into liquid nitrogen for a period of time. The tissue can be immersed for about at least 1, 2, 3, 4, 5, 6, 7, 8, 9, 10, or 15 minutes. In another embodiment, the xenograft can be frozen. For example, the tissue can be placed in a freezer or by exposing the tissue to temperatures at or below 0° C. Then, in the next step of the freeze/thaw cycling treatment, the xenograft tissue can be thawed by immersion in an suitable solution, for example, an isotonic saline bath. The temperature of the bath can be approximately at room temperature, such as about 25° C. The tissue can be immersed in the saline bath for a period of time that allows thawing, for example, at least 5, at least 10 or at least 15 minutes. In other embodiments, the tissue can be treated with cryoprotectants prior to or during the freeze-thawing treatment.

In yet a further embodiment, the xenograft can be exposed to a chemical agent to tan or crosslink the proteins within the extracellular matrix. Any tanning or crosslinking agent can be used for this treatment, and more than one crosslinking step can be performed or more than one crosslinking agent can be used to achieve a high degree of crosslinking. Cross linking agents can act, for example, in the following ways: by coupling an amine group on one biomolecule to a thiol group on a second biomolecule, forming crosslinks between amines of biopolymers, by crosslinking amines and thiols, forming crosslinks between amines and carboxylic acids or thiols and carboxylic acids.

In one embodiment, aldehydes, such as glutaraldehyde, formaldehyde, paraformaldehyde, formalin, aldehydes, adipic dialdehyde, tanning at acidic pH and the like, can be used to crosslink the collagen within the extracellular matrix of the tissue. In another embodiment, aliphatic and aromatic diamines, carbodiimides, diisocyanates, and other materials known by one skilled in the art can be used as crosslinking agents. In one embodiment, the xenograft tissue can be treated with glutaraldehyde. For example, the tissue can placed in a buffered solution that can contain at least 0.25, 0.5, 1, 2, 2.5, 3, 3.5, 4, 4.5, 5, 5.5, 6, 7, 8, 9, 10, 15 or 20% or about 0.05 to about 5.0%; about 1-3% or about 2-7% glutaraldehyde. This solution can have a pH of about 7.4, 7.5 or 7.6. Any suitable buffer can be used, such as phosphate buffered saline or trishydroxymethylaminomethane. In an alternative embodiment, the xenograft tissue can be treated with a crosslinking agent in a vapor form. In one embodiment, the crosslinking agent can be a vaporized aldehyde crosslinking agent, such as, for example, vaporized formaldehyde. In one embodiment, the tissue can be exposed to a vaporized crosslinking agent at a concentration of at least 0.25, 0.5, 1, 2, 2.5, 3, 3.5, 4, 4.5, 5, 5.5, 6, 7, 8, 9, 10, 15 or 20% or about 0.05 to about 5.0%; about 1-3% or about 2-7%. In another embodiment, the pH of the vaporized crosslinking agent can be about 7.4, 7.5 or 7.6. In another embodiment, the tissue can be treated with a crosslinking agent for at least 1, at least 2, at least 3, at least 4, at least 5, at least 6, at least 7, at least 8, at least 9, at least 10, at least 11, at least 12, at least 13, at least 14, at least 15 or at least 16 days. In specific embodiments, the tissue can be treated with a crosslinking agent for 3, 4 or 5 days.

Cross linking agents can also be selected from the group including, but not limited to: dithiothreitol (DTT, D-1532), tris-(2-carboxyethyl)phosphine (TCEP, T-2556) tris-(2-cyanoethyl)phosphine (T-6052). succinimidyl 3-(2-pyridyldithio)propionate (SPDP, S-1531), succinimidyl acetylthioacetate (SATA, S-1553), mercaptotryptophan, SPDP/DTT in combination, SPDP/TCEP in combination, dibromobimane (D-1379), BODIPY FL bis-(methyleneiodoacetamide) (D-10620), bis-((N-iodoacetyl)piperazinyl)sulfonerhodamine (B-10621), bis(imido esters), bis(succinimidyl esters), diisocyanates, diacid chlorides. bis-(4-carboxypiperidinyl)sulfonerhodamine, di(succinimidyl ester) (B-10622), 1-Ethyl-3-(3-dimethylaminopropyl)carbodiimide (EDAC, E-2247), succinimidyl ester of 6-((acryloyl)amino)hexanoic acid (acryloyl-X, SE; A-20770), and streptavidin acrylamide (S-21379, Section 7.5).

In another embodiment, the tissues from animals lacking any functional expression of the alpha-1,3-GT gene can be combined with other inert materials such as plastics, biopolymers, and metals (including but not limited to stainless steel and titanium) in order to provide additional mechanical strength or for other application benefits to the recipient patient. Biopolymers include, but are not limited to cellulose, alginic acid, chitosan, collagen, elastiri, and reticulin and analogs thereof, and mixtures thereof.

In other embodiments, the prostheses can further include synthetic materials, such as polymers and ceramics. Appropriate ceramics include, for example, hydroxyapatite, alumina, graphite and pyrolytic carbon. Appropriate synthetic materials include hydrogels and other synthetic materials that cannot withstand severe dehydration. The xenografts can also contain synthetic polymers as well as purified biological polymers. These synthetic polymers can be woven or knitted into a mesh to form a matrix or similar structure. Alternatively, the synthetic polymer materials can be molded or cast into appropriate forms.

Appropriate synthetic polymers include without limitation polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Bioresorbable polymers can also be used such as dextran, hydroxyethyl starch, gelatin, derivatives of gelatin, polyvinylpyrolidone, polyvinyl alcohol, poly[N-(2-hydroxypropyl) methacrylamide], poly (hydroxy acids), poly(epsilon-caprolactone), polylactic acid, polyglycolic acid, poly (dimethyl glycolic acid), poly(hydroxy buterate), and similar copolymers. These synthetic polymeric materials can be woven or knitted into a mesh to form a matrix or substrate. Alternatively, the synthetic polymer materials can be molded or cast into appropriate forms.

Biological polymers can be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

In one embodiment, the tissue can be used as a complete tissue replacement, such that, for example, the transplanted tissue performs the same biomechanical functionality of the tissue it is replacing or repairing. In a further embodiment, the tissue can be preconditioned (chemically and/or mechanically) prior to transplantation to allow optimal range of motion of the tissue following transplantation, or to allow for a "custom fit" for the recipient. In further embodiments, the tissue can be further treated and/or processed as described below to form de-cellularized products, which can be used, for example, as scaffold, once implanted.

A. Tissue Reconstruction, Repair and/or Replacement

In one embodiment of the present invention, the hard and soft tissue from animals lacking any expression of functional alpha-1,3-galactosyltransferase can be used for surgical applications. In one embodiment, the tissue can be used in orthopedic reconstruction and repair. Such tissues include soft tissue, such as connective tissue, tendons, ligaments, muscle and cartilage as well as hard tissue, such as bone and bone derivatives. In one embodiment, the tissue can be used for knee repair, such as anterior cruciate ligament (ACL) or posterior cruciate ligament (PCL) replacement. In another embodiment, the tissue can be used for bone-tendon-bone grafts, rotator cuff repair or as suture plugs. Bone tissue can be used as whole or partial bone replacement, bone plugs, bone screws or bone chips (including preparations in which bone chips can be prepared as a paste). Bone tissue can also be used for periodontal applications, cosmetic, and/or maxilofacial reconstruction. Tissue can also be used as spinal spacers for vertebrae repair. Tissue can also be used to replace tissue of the ear, such as ossicles, tympanic membranes, tympanic membranes with mallei attached, ear bone plugs, temporal bones, costal cartilage and dura mater), which can optionally be used for inner ear reconstruction.

1. Bone Tissue

In one embodiment, the invention provides a method of preparing a bone xenograft for implantation or engraftment into a human, which includes removing at least a portion of a bone or a whole piece of bone from an animal to provide a xenograft.

The bone can be harvested from any non-human animal to prepare the xenografts of the invention. In one embodiment, the bone can be obtained from bovine, ovine, or porcine animals. In another embodiment, the bone is obtained from immature pigs, calves or lambs. The bone of younger animals consists of more cancellous bone and is generally less brittle than that of older animals. In another embodiment, the bone is obtained from an animal between six and eighteen months of age.

An intact bone portion can be removed from a bone of the animal. The bone can be collected from freshly killed animals. Alternatively, the bone can be surgically removed from viable animals. Bones that are removed can include, but are not limited to, skull bone, such as anterior, lateral or posterior; vertebrae, such as cervical (atlas, axis, typical), thoracic (superior, inferior) lumbar (superior inferior lateral), sacrum, pelvis, thorax, sternum, rib, upper extremity bone, scapula, ventral, dorsal, clavicle, humerus (anterior or) posterior, radius-ulna (anterior or posterior), hand (dorsal or palmar), femur (anterior or posterior), tibia-fibula (anterior or posterior) and/or foot (dorsal or lateral). In one embodiment, after removal, the bone can be placed in a suitable sterile isotonic or other tissue preserving solution. Harvesting of the bone portions after slaughter of the animal can be done as soon as possible after slaughter and can be performed at cold temperature. For example, between about 5° C. and about 20° C., about 0° C. and about 20° C., about 0° C. and about 10° C., or about 0° C. and about 25° C.

The xenograft tissue, can then be washed in sterile, optionally cold, water to remove residual blood proteins and water soluble materials. In one embodiment, the xenograft tissue can then be immersed in alcohol under conditions such as those described above. The xenograft can be subjected to chemical, mechanical or biological treatments, such as those described above.

In one embodiment, the harvested bone portion can be cut up into strips or blocks. In another embodiment, the harvested bone can be made into any useful configuration of a bone graft, including, but not limited to, bone dowels, spinal spacers, bone plugs, bone chips, bone screws, bone cement, D-shaped spacers and cortical rings. The strips, blocks or other bone grafts can be created such that cancellous bone is attached to cortical bone. Alternatively, strips, blocks or other bone grafts can be created such that cancellous bone is not attached to cortical bone.

Bone Cement and Bone Plugs

In other embodiments of the present invention, bone cement and bone plugs from animals lacking any expression of functional alpha-1,3-GT are provided.

Bone cement compositions are useful in the bonding or fixing of an implant material, as well as in the strengthening of damaged natural bone. Such applications are useful in the areas of, for example, orthopedics, dentistry and related medical disciplines. The field of orthopedics deals with bone defects due to fracture, bone tumors, and other diseases of the bone. Treatment may require surgical resection of all, or part, of a bone. In dentistry applications, a defected jawbone may result from extraction of a tooth, cancer or other diseases. An implant material is useful in repairing or reconstructing the bone remaining after the resection of such bone defects. Implant materials used during such procedures can be metal, ceramics and polymers. Bone cement can be used in addition to other implant material to bond and affix the implant to the remaining, living bone. For example, polymethyl methacrylate (PMMA) has been widely used with hardware instrumentation in orthopedics.

Although conventional PMMA bone cement has been used in orthopedic surgery for over 40 years, it is far from ideal because 1) it does not encourage bone in-growth, 2) it is a weaker implement than bone cortex, and 3) it has a high exotherm and monomer toxicity. Thus, the present invention provides matrix materials, such as those described herein, that can be formulated into bone cement. Such bone cement can exhibit quick hardening time and/or chemically bonds, to affix an artificial biomaterial (e.g., implant material). This cement can display in vivo bioactivity, maintain mechanical strength, be characterized by adequate stiffness and modulus and/or improves bone mass through its physical and chemical effects. The bone cement can include a powder and liquid component. In one embodiment, the bioactive bone cement is provided in a powder-liquid phase, comprising a powder phase material and a liquid phase material. In another embodiment, the bioactive bone cement is provided in a paste-paste phase, comprising two separate paste materials. Additionally, the bone cement materials provided herein can be combined with other types of bone cement components, such as, PMMA bone cement. The bone cement can be used in any conventional manner, such as through injection via a syringe. The bone cement of the present invention can be used, for example, in spinal surgery via injection with a syringe. Syringe injection provides a minimally invasive delivery technique via the use of a syringe and a large bore needle. It also allows the cement to conform precisely to its area of placement. Additionally, the bone cement or paste can be combined with growth factors or cytokines, including but not limited to, bone morphogenic proteins (BMPs).

Bone plugs can be used for permanent or temporarily blocking of a canal in a long bone. For fixating of an endoprosthesis or artificial joint, for example an artificial hip prosthesis, in a bone, a stem of the prosthesis is inserted in the intramedullary canal of a long bone which is filled with bone cement. In order to prevent the bone cement to protrude in the canal any further than necessary for fixating of the stem and to assure that the bone cement is only present between the stem and the endosteal wall of the bone and to prevent leaking of the bone cement any further into the intramedullary canal, the canal beneath the stem is blocked with a bone plug. (see, for example, U.S. Pat. Nos. 6,669,733, 6,494,883).

Bone plugs can be molded in a wide range of sizes and having various height-to-diameter ratios in order to accommodate a wide range of cartilage replacement situations. The bone plug can be a polygonal or circular cross-section. For example, the plug can be a round devices having a shape ranging from flat disks to cylinders. A variety of factors can be taken into consideration for each particular application, such as the location where the bone replacement plug or plugs are to be implanted, the size of the bone defect that is to be repaired, and the size and shape of the void cavity, either as initially formed by resection of the defect, or by any subsequent surgical contouring of the cavity, into which the cartilage replacement plug is to be implanted.

Bone cement plugs can also be used, such devices are well known in the art. Bone cement plugs can be used in conjunction with bone cement dispensers to compact bone cement into a bone canal before fixing a prosthetic device in that bone canal. By way of example, bone cement plugs can be used in conjunction with bone cement despensers to compact bone cement into the intramedullary canal of the femur before fixing the femoral stem of an artificial hip in that canal. More particularly, in total joint replacement surgeries, such as hip and shoulder replacements, bone cement can be used to fix the stems of the prosthetic devices into the medullary canals of the joint's bones. In thcan be respect, it has generally been found that a prosthetic device will be more securely fixed in a bone canal if the bone cement can be well packed into the bone canal before the stem of the prosthetic device is positioned in the bone canal. In one example, after initial preparation and cleaning of the bone canal, the distal portion of the canal can be generally occluded with a plug. The bone cement plug can serve to limit uncontrolled flow of bone cement into the distal portion of the bone canal. In one specific embodiment, the bone cement plug can limit the column of bone cement to about 1 to 2 cm beyond the distal tip of the stem of the prosthesis. After the plug has been set at the distal portion of the bone canal, the bone cement can be injected into the distal-most part of the occluded bone canal, adjacent to the plug, using a bone cement dispenser having a long nozzle. The bone canal can be then filled with bone cement in a retrograde fashion, by withdrawing the nozzle of the bone cement dispenser from the distal end of the bone canal to the proximal end of the bone canal, as the cement issues from the nozzle. Such retrograde filling can help to avoid trapping air in the distal-most part of the bone canal. After the bone canal has been filled with bone cement, a bone canal pressurizer can then be connected to the bone cement dispenser. The pressurizer can be pressed against the open end of the bone so as to occlude the proximal end of the bone canal. More cement can be then injected into the bone canal through the pressurizer and under pressure. Under such pressurization, the cement in the bone canal intrudes into the interstices of the inner surface of the bone wall defining the bone canal. When the bone cement thereafter sets, a micro-interlock can be established between the cement and the irregularities of the inner surface of the bone wall. This can significantly enhance fixation of the prosthetic device in the bone canal.

In one embodiment, the bone cement plug can be easy to deploy at the desired depth in the bone canal, effective in closing off that bone canal and, in the event that the bone cement plug subsequently needs to be removed, easy to retrieve from the distal end of the bone canal.

A variety of bone cement plugs are known in the art. See, for example, U.S. Pat. Nos. 4,245,359; 4,276,659; 4,293,962; 4,302,855; 4,344,190; 4,447,915; 4,627,434; 4,686,973; 4,697,584; 4,745,914; 4,936,859; 4,950,295; 4,994,085; 5,061,287; 5,078,746; 5,092,891; 5,376,120; 4,011,602; 4,523,587; 4,904,267, 6,299,642, 6,306,142 and 5,383,932, and WO 94/15544.

Surgical techniques for transplanting bone plugs can involve removing the damaged bone tissue by drilling or cutting a hole at the site of the damage, and plugging this hole with a bone plug. Surgical instruments can be used to harvest or extract a bone plug from a donor site from an animal lacking any expression of functional alpha-1,3-GT. The bone plug can then be implanted it into a pre-formed hole at a recipient site. A conventional harvesting instrument can include a tube having a cutting edge at the distal end. To extract the plug, the instrument can be driven into the bone at the donor site and then removed, taking with it a plug of bone tissue.

Bone Screws

In another embodiment, bone screws derived from animals lacking any expression of functional alpha-1,3-GT are provided.

One method of reducing bone fractures can be to use external fixation devices which allows fractures to be consolidated to highly critical areas, as may be especially those proximate to joints, or fractures involving serious damage to the cutaneous tissue to be treated, that is, anywhere traditional plastering may prove inappropriate or impracticable. Such devices, usually of complex construction and supplied in varying configurations for adaptation to the most unpredictable of contingent situations, have opposite ends which are fastened to respective undamaged portions of the broken bone, using screws firmly set in the bone material of these portions. Thus, for example in the case of a tibial fracture, the opposite ends of a corresponding (tibial) fixation device are secured across the fractured region. In other cases, where the fracture involves a joint such as an ankle, the bone screws of a corresponding external fixation device are set in the shinbone and the talus.

Bone screws for fastening the external fixation device, and thus ensuring the device effectiveness, can include a screw head designed for engagement by a suitable driver, and a screw shank having a threaded portion which usually tapers toward a screw tip at the opposite end from said head. The screw head can be formed with a flat which extends parallel to the screw axis, milled on one side of the screw shank. Bone screws can be on varying lengths such that the screw is suitable for the particular size and shape of bone into which it can be inserted.

Spinal Spacers

In other embodiments of the present invention, any component of the spine from animals lacking any expression of functional alpha-1,3-GT are provided. Such componnents include, but are not limited to, spinal spacers, intervertebral discs, the nucleus pulposus and/or the annulus fibrosis.

Spinal fusion is indicated to provide stabilization of the spinal column for painful spinal motion and disorders such as structural deformity, traumatic instability, degenerative instability, and post-resection iatrogenic instability. Fusion, or arthrodesis, is achieved by the formation of an osseous bridge between adjacent motion segments. This can be accomplished within the disc space, anteriorly between contiguous vertebral bodies or posteriorly between consecutive transverse processes, laminae or other posterior aspects of the vertebrae. A successful fusion requires the presence of osteogenic or osteopotential cells, adequate blood supply, sufficient inflammatory response, and appropriate preparation of local bone.

A fusion or arthrodesis procedure can be performed to treat an anomoly involving an intervertebral disc. Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosis. In a healthy, undamaged spine, the annulus fibrosis prevents the nucleus pulposus from protruding outside the disc space.

Spinal discs can be displaced or damaged due to trauma, disease or aging. Disruption of the annulus fibrosis allows the nucleus pulposus to protrude into the vertebral canal, a condition commonly referred to as a herniated or ruptured disc. The extruded nucleus pulposus may press on the spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain. One treatment for these conditions is a discectomy, or surgical removal of a portion or all of an intervertebral disc followed by fusion of the adjacent vertebrae. The removal of the damaged or unhealthy disc can allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts or spinal spacers can be used to fill the intervertebral space to prevent disc space collapse and promote fusion of the adjacent vertebrae across the disc space. Many attempts to restore the intervertebral disc space after removal of the disc have relied on metal devices (see, for example, U.S. Pat. Nos. 4,878,915, 5,044,104; 5,026,373, 4,961,740; 5,015,247, 5,147,402 and 5,192,327)

Spinal components from animals lacking expression of functional alpha-1,3-GT can be prepared according to conventional methods. The bone can be obtained from the animal and then cleaned to remove tissue and blood. The bone can be treated with agents, such as alcohol and peroxides or other agents as described above, to remove cellular material, fats and noncollagenous proteins. The bone material can be treated to remove free collagen, leaving bound or structural collagen. One agent for removing free collagen and any remaining fat is sodium dodecyl sulfate (SDS).

2. Soft Tissue

Soft tissue connects, supports or surrounds other structures and organs of the body. Soft tissue includes, for example, muscles, tendons, fat, blood vessels, lymph vessels, nerves, tissue around the joints skin or any other tissue other than bone.

Soft tissues, such as such as connective tissue, tendons, meniscus, ligaments, muscle and cartilage can be extracted from a joint of an animal. The source of the tissue can be collected from freshly killed animals. Alternatively, the tissue can be surgically removed from viable animals. Any joint can serve as the source of the soft tissue. In embodiments of the invention, tissue from a corresponding donor joint can be used to make the xenograft tissue. For example, cartilage from a femuro-tibial (stifle) joint can be used to make a cartilage xenograft for implantation into a knee. In another example, cartilage from a donor animal's hip joint can be used to make a cartilage xenograft for a human hip joint.

Figure 7:
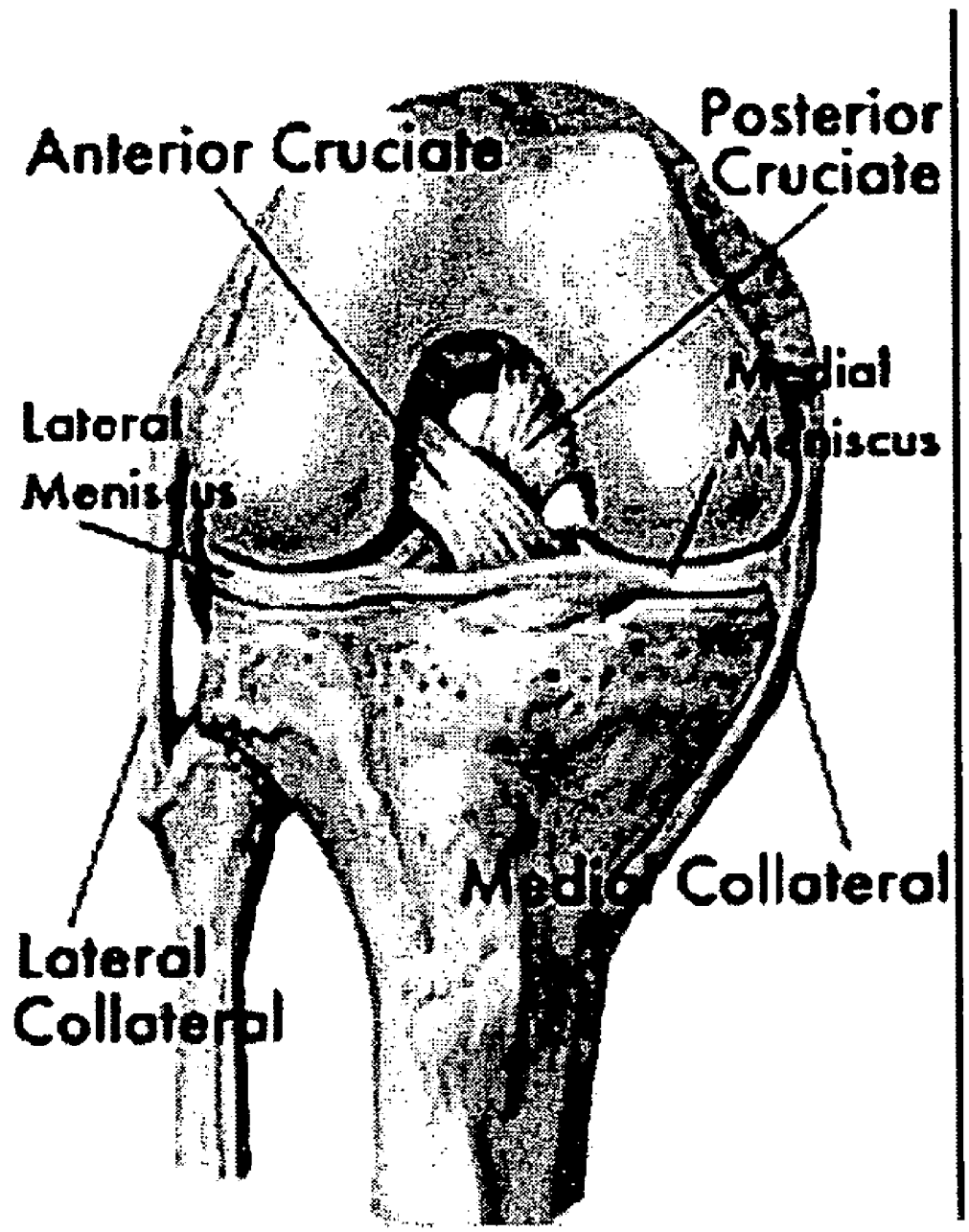
FIG. 7 provides an overview of the anatomy of the knee. It shows a front view of the right knee in a flexion position.

In one embodiment, the soft tissue can be extracted from the knee joint. The knee is a complex joint containing spatially interrelated bones, ligaments, and cartilaginous structures which interact to create a variety of motions. Specifically, the femoral condyles articulate with the surface plateaus of the tibia, through the cartilaginous medial and lateral menisci, and all of these structures are held in place by various ligaments. There are essentially four separate ligaments that stabilize the knee joint (see, for example, FIG. 7). On the sides of the joint lie the medial collateral ligament (MCL) and the lateral collateral ligament (LCL) which serve as stabilizers for the side-to-side stability of the joint. The MCL is a broader ligament that is actually made up of two ligament structures, the deep and superficial components, whereas the LCL is a distinct cord-like structure. In the front part of the center of the joint is the anterior cruciate ligament (ACL). This ligament is a very important stabilizer of the femur on the tibia and serves to prevent the tibia from rotating and sliding forward during agility, jumping, and deceleration activities. Directly behind the ACL is its opposite, the posterior cruciate ligament (PCL). The PCL prevents the tibia from sliding to the rear.

The medial and lateral menisci are structures comprised of cells called fibrochondrocytes, an interstitial matrix of fibers of the protein collagen, and within a ground substance formed from proteoglycans. Undamaged menisci provide shock absorption for the knee by ensuring proper force distribution, stabilization, and lubrication for the interacting bone surfaces within the knee joint, which are routinely exposed to repeated compression loading during normal activity. Much of the shock absorbing function of the medial and lateral menisci is derived from the elastic properties inherent to cartilage. When menisci are damaged through injury, disease, or inflammation, arthritic changes occur in the knee joint, with consequent loss of function.

The anterior cruciate ligament of the knee (the ACL) functions to resist anterior displacement of the tibia from the femur at all flexion positions. The ACL also resists hyperextension and contributes to rotational stability of the fully extended knee during internal and external tibial rotation. The ACL may play a role in proprioception. The ACL is made up of connective tissue structures composed of cells, water, collagen, proteoglycans, fibronectin, elastin, and other glycoproteins (see, for example, Cyril Frank, M. D. et al., Normal Ligament: Structure, Function, and Composition. Injury and Repair of the Musculoskeletal Soft Tissues, 2:45-101). Structurally, the ACL attaches to a depression in the front of the intercondyloid eminence of the tibia extending postero-superiorly to the medial wall of the lateral femoral condyle. Partial or complete tears of the ACL are very common, comprising about 30,000 outpatient procedures in the U.S. each year.

Articular cartilage covers the ends of all bones that form articulating joints in humans and animals. The cartilage is made of cells called fibrochondrocytes and an extracellular matrix of collagen fibers as well as a variety of proteoglycans. The cartilage acts in the joint as a mechanism for force distribution and as a lubricant in the area of contact between the bones. Without articular cartilage, stress concentration and friction would occur to the degree that the joint would not permit ease of motion. Loss of the articular cartilage usually leads to painful arthritis and decreased joint motion. Since joint cartilage in adults does not naturally regenerate to a significant degree once it is destroyed, damaged adult articular cartilage has historically been treated by a variety of surgical interventions including repair, replacement, or by excision.

In one embodiment, meniscal soft tissue can be extracted from a joint by first transecting the patellar tendon, the horns of the menisci can then be dissected free of adhering tissue. Optionally, a small amount of bone can remain attached to the horns, for example, a substantially cylindrical plug of bone, such as a bone plug. In one specific example, the bone plug can be approximately five millimeters in diameter by five millimeters in depth. In one embodiment, the meniscal synovial junction can then be identified and freed from the meniscus tissue itself, to form a matrix material. In another embodiment, the intact meniscal soft tissue can be used for transplantation.

In another embodiment, articular cartilage soft tissue can be extracted from a joint. In one embodiment a fine peel of articular cartilage with a small layer of subchondral bone can be identified and shaved from the donor joint, this can form matrix material. In another embodiment, the intact articular cartilage soft tissue can be used for transplantation.

In a further embodiment, ligament soft tissue can be extracted from a joint, such as the anterior cruciate ligament, posterior cruciate ligament, lateral collateral ligament or the medial collateral ligament. To remove the ligament, the joint can be opened using standard surgical techniques. In one embodiment, the ligament can be harvested with a block of bone attached to one or both ends. In one example, a block of bone representing a substantially cylindrical plug can be extracted with the ligament, the bone plug can be approximately 9-10 mm in diameter by approximately 20-40 mm in length. In another embodiment, the ligament is harvested without bone. In a further embodiment, the ligament can be harvested without bone and then dissected free of adhering tissue to obtain a matrix material. In another embodiment, the intact ligament soft tissue can be used for transplantation.

After removal, the tissue can be placed in a suitable sterile isotonic or other tissue preserving solution. Harvesting of the tissue after slaughter of the animal can be done as soon as possible after slaughter and can be performed at cold temperature. For example, between about 5° C. and about 20° C., about 0° C. and about 20° C., about 0° C. and about 10° C., or about 0° C. and about 25° C.

Collagen

In another embodiment, collagen tissue of the present invention can be used to treat collagen disorders. Alterations in collagen structure resulting from abnormal genes or abnormal processing of collagen proteins results in numerous diseases, such as Larsen syndrome, scurvy, osteogenesis imperfecta and Ehlers-Danlos syndrome. Ehlers-Danlos syndrome is actually the name associated with at least ten distinct disorders that are biochemically and clinically distinct yet all manifest structural weakness in connective tissue as a result of defects in the structure of collagens. Osteogenesis imperfecta also encompasses more than one disorder. At least four biochemically and clinically distinguishable disorders have been identified all of which are characterized by multiple fractures and resultant bone deformities. Marfan's syndrome manifests itself as a disorder of the connective tissue and was believed to be the result of abnormal collagens. However, recent evidence has shown that Marfan's results from mutations in the extracellular protein, fibrillin, which is an integral constituent of the non-collagenous microfibrils of the extracellular matrix.

TABLE 3

Collagen Disorders

| Disorder | Collagen Defect | Symptomology |
| --- | --- | --- |
| Ehlers-Danlos IV | decrease in type III | arterial, intestinal and uterine rupture, thin easily bruised skin |
| Ehlers-Danlos V | decreased cross-linking | skin and joint hyperextensibility |
| Ehlers-Danlos VI | decreased hydroxylysine | poor wound healing, musculo-skeletal deformities, skin and joint hyperextensibility |
| Ehlers-Danlos VII | N-terminal pro-peptide not removed | easily bruised skin, hip dislocations, hyperextensibility |
| Oseteogenesis imperfecta | decrease in type I | blue sclerae, bone deformities |
| Scurvy | decreased hydroxyproline | poor wound healing, deficient growth, capillary weakness |

Cartilage Plugs

In other embodiments, cartilage plugs are provided that are obtained from animals lacking expression of functional alpha-1,3-GT. Cartilage plugs can be used to fill a void in natural cartilage. Voids in natural cartilage can be due to traumatic injury or chronic disease Alternatively, the plug can be used to anchor a flowable polymer to subchondral bone. The plug can be made into any size, shape, and contour that is appropriate for the desired transplant. The plugs can be utilized either singly or in a plurality to fill any size void for any application. The plug can be formed of or also include a laminated structure to match the physiological requirements of the repair site. Additionally, ridges can be formed about the periphery of each plug to facilitate its anchoring to surrounding cartilage, bone and/or adjacent plugs (see, for example, U.S. Pat. No. 6,632,246).

The cartilage plug can be a polygonal or circular cross-section. The polygonal or circular cross-section can encompass a height-to-diameter ratio of from about less than one to one to about 20:1, about 30:1 or about 40:1. The plugs can be molded in a wide range of sizes and having various height-to-diameter ratios in order to accommodate a wide range of cartilage replacement situations. For example, the plug can be a round devices having a shape ranging from flat disks to cylinders. A variety of factors can be taken into consideration for each particular application, such as the location where the cartilage replacement plug or plugs are to be implanted, the size of the cartilage defect that is to be repaired, and the size and shape of the void cavity, either as initially formed by resection of the defect, or by any subsequent surgical contouring of the cavity, into which the cartilage replacement plug is to be implanted. For example, cartilage replacement plug devices that have a flattened, disk shape are most suitable for more extensive but shallow defects, while devices having a large height-to-diameter ratio are suitable for defects having a smaller surface area, but which extend deeper into the cartilage and/or the subchondral bone layer.

The surfaces of the cartilage plugs of the present invention can be treated so as to expose a porous or roughened surface. By treating the surface of the plug such that it is roughened or textured, cell attachment can be enhanced and allows for cell migration and overgrowth of a tissue layer. With appropriate surface asperity, the resultant cells can adhere via ongrowth and ingrowth into the surface of the plug enhancing fixation. Such cell ingrowth can be ultimately transformed into a bony interface with the plug and is considered a desirable characteristic. Important in this transformation is how load is transferred from the device to the surrounding tissue. A large mismatch in deformation between the plug and surrounding tissue can lead to a fibrous tissue layer around the plug that, although flexible, does not provide the desired fixation. Porosity, like asperity, can be important and beneficial when considering biologic fixation.

Suture Anchors

Soft tissue provided in the present invention can be used to form suture anchors, which can be used to secure sutures within openings formed in bones during joint reconstructive surgery and arthroscopic surgical procedures. The anchor can be placed in a bone and connected to a suture that could otherwise not be secured to dense osseous material. Such suture anchors can be used, for example, to anchor ligaments or tendons to bones in knee, shoulder and elbow reconstruction and repair operations. Important attributes of bone anchors are that they be easy to insert, and provide a firm anchor. Unintended dislodgement of the anchor after surgery can have serious adverse consequences, hence much importance is placed on the ability of an anchor to resist extraction or withdrawal forces exerted by the attached suture. (see, for example, U.S. Pat. Nos. 4,738,255, 4,013,071, 4,409,974, 4,454,875, and 5,236,445)

The present invention also provides methods of anchoring a suture to a bone. First a bore hole can be drilled in the bone. The bone anchor can then be inserted, distal end first, into the bore hole. An expansion instrument, such as a rod with an oblong or oval cross-section, can be inserted into the expansion chamber through the open proximal end of the anchor. The slotted proximal end of the bone anchor is then expanded by rotating the instrument to bring the instrument into contact with the walls as the instrument rotates. The oblong or oval cross-section of the instrument permits it to rotate through at least a portion of a revolution before contacting the walls, such that the bone anchor is less likely to rotate with the instrument. In one embodiment, the distal tip of the instrument seats in a corresponding recess at the distal end of the expansion chamber. The recess provides a fixed pivot point about which the rod rotates to expand the anchor.

3. Scaffolds

In certain embodiment, processes to prepare tissue can include steps to strip away or kill all viable cells (decellularization) leaving behind only an acellular matrix or scaffold for use in tissue repair and remodeling, as well as, optionally, treatments for crosslinking and sterilization. In a particular embodiment, any decellularized hard or soft tissue is provided that is derived from the animals disclosed herein. In one embodiment, de-cellularized soft dermal tissue is provided. In another embodiment, de-cellularized submucosal tissue is provided. In other embodiment, such de-cellularized material can be less immunogenic. In further embodiments, such de-cellularized tissues can be used as a scaffolding or matrix to repair and/or reconstruct particular human body parts. In one embodiment, the decellularized tissue can be used for the repair of the following, incluing, but not limited to, hernia, abdominal wall, rotator ciff, cosmetic surgery or any other soft tissue defects known to one skilled in the art or disclosed herein. In particular embodiments, submucosal and or dermal decellularized material is provided.

In one aspect of the present invention, tissues derived from these alpha 1,3GT animals can be procured (harvested) and then further processed to form de-cellularized tissue, for example, for use as scaffolds. In one embodiment, the tissue can be subject to a multi-step process including, but not limited to, treating the tissue with a stabilizing solution, a decellularization process to remove cells and any remaining antigenic tissue components, enzymatic treatment, cross-linking to improve structural integrity of the tissue or to remove any remaining antigenic tissue components, sterilization to remove and/or inactivate native virus, and/or long term preservation methods. In one embodiment, the stabilizing solution can contain an appropriate buffer, one or more anti-oxidants, one or more oncotic agents, an antibiotic, and may include one or more protease inhibitors.

In other embodiments, the tissue processing to produce de-cellularized tissue can include, for example, removal of cells that can lead to tissue rejection and graft failure, without damaging the matrix. The process of decellularization has the advantage of rendering the tissue as strong as synthetics, yet more pliable, retaining tensile and functional characteristics, helping to prevent adhesions, decreased infection and rejection of the graft, and promoting remodeling of the surrounding host tissue. In other embodiments, decellularization can be accomplished using a number of chemical treatments, including incubation in certain salts, detergents or enzymes, and/or a vacuum/pressure process. In one embodiment, the detergent can be Triton X-100 (Rohm and Haas Company of Philadelphia, Pa.). In a certain embodiment, the Triton X-100 remove cellular membranes, see, for example, U.S. Pat. No. 4,801,299. Other decellularizing detergents include, but are not limited to, polyoxyethylene (20) sorbitan mono-oleate and polyoxyethylene (80) sorbitan mono-oleate (Tween 20 and 80), sodium deoxycholate, 3-[(3-chloramidopropyl)-dimethylammino]-1-propane-sulfonate, octyl-glucoside and/or sodium dodecyl sulfate or any other detergent known to one skilled in the art. In another embodiment, enzymes can be used to accomplish decellularization. In certain embodiments, the enzymes can be selected from the group including, but not limited to dispase II, trypsin, and/or thermolysin or any other enzyme known to one skilled in the art. These enzymes can react with different components of collagen and intercellular connections. For example, dispase II can attack Type IV collagen, which is a component of the lamina densa and anchoring fibrils of the basement membrane. In another example, thernolysin can attack the bulbous phemphigoid antigen in the hemidesmosome of the basal layer of keratinocytes. In a further example, trypsin can attack the desmosome complex between cells.

In additional or alternative embodiments, the de-cellularized xenograft can be exposed to a chemical agent to tan or crosslink the proteins within the extracellular proteins, to further diminish or reduce the immunogenic determinants present in the xenograft. Any tanning or crosslinking agent may be used for this treatment, and more than one crosslinking step can be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, can be used to crosslink the extracellular collagen. Other suitable crosslinking agents include aliphatic and aromatic diamines, carbodiimides, diisocyanates, and the like. Alternatively, the xenograft can be exposed to a crosslinking agent in a vapor form, including, but not limited to, a vaporized aldehyde crosslinking agent, such as, for example, vaporized formaldehyde. The crosslinking reaction should continue until the immunogenic determinants are substantially removed from the xenogeneic tissue, but the reaction should be terminated prior to significant alterations of the mechanical properties of the xenograft. The crosslinking agents can be any agents known to one skilled in the art or described herein.

In certain embodiments, matrix material derived from such soft tissue can be used to form a scaffold or prosthetic device. The matrix material can be converted into a dry, porous volume matrix, a portion of which can optionally be cross-linked. The porous matrix of the prosthetic device encourages ingrowth of cells, such as meniscal fibrochondrocytes, endothelial cells, fibroblasts, and other cells that normally occupy the extracellular matrix as well as synthesize and deposit extracellular matrix components. Extracellular matrix fibers, such as collagen, elastin, reticulin, analogs thereof and mixtures thereof, can be added to the matrix material. These fibers can also be obtained from animals lacking any functional expression of alpha-1,3-gal. In one embodiment, the fibers can be randomly oriented throughout the matrix. Alternatively, the fibers can assume substantially circumferentially extending or substantially radially extending orientation throughout the matrix. The density of the fibers of the matrix can be uniform or non-uniform. In non-uniform configurations, relatively high densities of fibers can be established at anticipated points of high stress.

The matrix materials can also contain other types of materials, such as biopolymers as described above. The matrix material can contain glycosaminoglycan molecules (GAGs), such as, but are not limited to, chondroitin 4-sulfate, chondroitin 6-sulfate, keratan sulfate, dermatan sulfate, heparan sulfate, hyaluronic acid, and mixtures thereof can be components of the matrix material. In addition, the matrix material can contain GAGs interspersed throughout the fibers. The GAGs can be uniformly dispersed throughout the matrix as individual molecules, or they can be present in varying amounts in different regions of the device.

In another embodiment, the scaffolds formed from tissues from animal lacking any functional expression of the alpha-1,3-GT gene as described herein can also contain extracellular matrix (ECM) components. In one embodiment, such ECM components can be derived from an animal lacking any functional expression of the alpha-1,3-GT gene. Extracelluar matrix materials can be derived from any tissue, including, but not limited to, skin, urinary, bladder or organ submucosal tissues. The scaffold can function as a prosthetic device. The scaffold can be synthesized from fragmented ECM components, or in a preferred embodiment, is derived via decellularization or processing of native tissue, thus removing live cells and leaving behind the ECM as a preformed scaffold with a 3-D structure and fiber configuration similar to the natural tissue. The scaffold or device can be derived from matrix material obtained from soft tissue of an animal that lacks any functional expression of alpha-1,3-Gal. The soft tissue can include, but is not limited to, dermis, organ submucosa (ie. small intestine submucosa (SIS)), the lateral meniscus removed from a knee joint, articlar cartilage removed from any joint, ligaments and/or tendons, such as the Achilles tendon. The tissue can then be processed as described below to obtain a matrix material, such as biocompatible and bioresorbable fibers.

The extracellular matrix (ECM) is a complex structural entity surrounding and supporting cells that are found within mammalian tissues. The ECM can also be referred to as connective tissue. The ECM is composed of structural proteins, such as collagen and elastin, specialized proteins, such as fibrillin, fibronectin, and laminin, and proteoglycans. Glycosaminoglycans (GAGs) are long chains of repeating disaccharide units forming extremely complex high molecular weight components of the ECM. These disaccharide units contain an N-acetylated hexosamine and provide lubrication and cross-links. Examples of GAGs include, but are not limited to, chondroitin 4-sulfate, chondroitin 6-sulfate, keratan sulfate, dermatan sulfate, heparan sulfate and hyaluronic acid.

TABLE 1

Representative matrix types produced by vertebrate cells

| Collagen | Anchor | Proteoglycan | Cell-Surface Receptor | Cells |
|---|---|---|---|---|
| I | fibronectin | chondroitin and dermatan sulfates | Integrin | fibroblasts |
| II | fibronectin | chondroitin sulfate | Integrin | chondrocytes |
| III | fibronectin | heparan sulfate and heparin | Integrin | quiescent hepatocytes, epithelial; assoc. fibroblasts |
| IV | laminin | heparan sulfate and heparin | laminin receptors | all epithelial cells, endothelial cells, regenerating hepatocytes |
| V | fibronectin | heparan sulfate and heparin | Integrin | quiescent fibroblasts |
| VI | fibronectin | heparan sulfate | Iitegrin | quiescent fibroblasts |

Collagens are the most abundant proteins found in the animal kingdom. It is the major protein comprising the ECM. There are at least 12 types of collagen. Types I, II and III are the most abundant and form fibrils of similar structure. Type IV collagen forms a two-dimensional reticulum and is a major component of the basal lamina. Collagens are predominantly synthesized by fibroblasts but epithelial cells also synthesize these proteins. The fundamental higher order structure of collagens is a long and thin diameter rod-like protein. Type I collagen for instance is approximately 300 nm long, 1.5 nm in diameter and consists of 3 coiled subunits composed of two $\alpha1(I)$ chains and one $\alpha2(I)$ chain. Each chain consists of 1050 amino acids wound around each other in a characteristic right-handed triple helix. There are 3 amino acids per turn of the helix and every third amino acid is a Guanine. Collagens are also rich in proline and hydroxyproline. The bulky pyrollidone rings of proline reside on the outside of the triple helix. Lateral interactions of triple helices of collagens result in the formation of fibrils roughly 50 nm diameter. The packing of collagen is such that adjacent molecules are displaced approximately ¼ of their length (67 nm). This staggered array produces a striated effect that can be seen in the electron microscope.

Collagens are synthesized as longer precursor proteins called procollagens. Type I procollagen contains an additional 150 amino acids at the N-terminus and 250 at the C-terminus. These pro-domains are globular and form multiple intrachain disulfide bonds. The disulfides stabilize the proprotein allowing the triple helical section to form. Collagen fibers begin to assemble in the endoplasmic reticulum (ER) and Golgi complexes. The signal sequence is removed and numerous modifications take place in the collagen chains. Specific proline residues can be hydroxylated by prolyl 4-hydroxylase and prolyl 3-hydroxylase. Specific lysine residues also are hydroxylated by lysyl hydroxylase. Prolyl hydraoxylases are dependent upon vitamin C as co-factor. Glycosylations of the O-linked type also occurs during Golgi transit. Following completion of processing the procollagens are secreted into the extracellular space where extracellular enzymes remove the pro-domains. The collagen molecules then polymerize to form collagen fibrils. Accompanying fibril formation is the oxidation of certain lysine residues by the extracellular enzyme lysyl oxidase foming reactive aldehydes. These reactive aldehydes form specific cross-links between two chains thereby, stabilizing the staggered array of the collagens in the fibril.

arise by alternative RNA splicing of the primary transcript from a single fibronectin gene. Fibronectins contain at least 6 tightly folded domains each with a high affinity for a different substrate such as heparan sulfate, collagen (separate domains for types I, II and III), fibrin and cell-surface receptors. The cell-surface receptor-binding domain contains a consensus amino acid sequence, RGDS.

All basal laminae contain a common set of proteins and GAGs. These are type IV collagen, heparan sulfate proteoglycans, entactin and laminin. The basal lamina is often refered to as the type IV matrix. Each of the components of the basal lamina is synthesized by the cells that rest upon it. Laminin anchors cell surfaces to the basal lamina.

In one embodiment, any of the ECM components or combinations thereof described above can be used to form a scaffold, which can optionally be used as a prosthetic device. The ECM-derived scaffold can alternatively be produced by mechanical, chemical or enzymatic treatment of tissue from alpha 1,3 gal knockout pigs, such that all cells and debris are removed leaving behind the ECM in a fiber pattern well suited for recruitment of host cells and tissue regeneration. The scaffold or prosthetic device fabricated from biocompatible and bioresorbable fibers can be surgically implanted into a region disposed between and connecting two of the subject's bones, so as to provide normal motion and strength (for surgical implantation, see, for example, U.S. Pat. Nos. 6,042,610, 5,735,903, 5,479,033, 5,624,463, 5,306,311, 5,108,438, 5,007,934 and 4,880,429). The prosthetic device can act as a scaffold for regenerating tissue since the physical characteristics of the scaffold encourage the in-growth of the new tissue. This can result in a composite of the subject host body region and the prosthetic device that has an in vivo outer surface contour that is substantially the same as a natural body region.

TABLE 2

Types of Collagen

| Types | Chain Composition | Structural Details | Localization |
|---|---|---|---|
| I | [α1(I)]$_2$[α(I)] | 300 nm, 67 nm banded fibrils | skin, tendon, bone, etc. |
| II | [α1(II)]$_3$ | 300 nm, small 67 nm fibrils | cartilage, vitreous humor |
| III | [α1(III)]$_3$ | 300 nm, small 67 nm fibrils | skin, muscle, frequently with type I |
| IV | [α1(IV)$_2$[α2(IV)] | 390 nm C-term globular domain, nonfibrillar | all basal lamina |
| V | [α1(V)][α2(V)][α3(V)] | 390 nm N-term globular domain, small fibers | most interstitial tissue, assoc. with type I |
| VI | [α1(VI)][α2(VI)][α3(VI)] | 150 nm, N + C term. globular domains, microfibrils, 100 nm banded fibrils | most interstitial tissue, assoc. with type I |
| VII | [α1(VII)]$_3$ | 450 nm, dimer | epithelia |
| VIII | [α1(VIII)]$_3$ | — | some endothelial cells |
| IX | [α1(IX)][α2(IX)][α3(IX)] | 200 nm, N-term. globular domain, bound proteoglycan | cartilage, assoc. with type II |
| X | [α1(X)]$_3$ | 150 nm, C-term. globular domain | hypertrophic and mineralizing cartilage |
| XI | [α1(XI)][α2(XI)][α3(XI)] | 300 nm, small fibers | cartilage |
| XII | α1(XII) | — | interacts with types I and III |

The role of fibronectins is to attach cells to a variety of extracellular matrices. Fibronectin attaches cells to all matrices except type IV that involves laminin as the adhesive molecule. Fibronectins are dimers of 2 similar peptides. Each chain is approximately 60-70 nm long and 2-3 nm thick. At least 20 different fibronectin chains have been identified that The device can be implanted into a region between and/or connecting two of the subject's bones, the composite formed by the subject's body region and the device can have an in vivo outer surface contour substantially the same as a natural region that is being treated. The device can establish a biocompatible and partially bioresorbable scaffold adapted for ingrowth of fibrochondrocytes, fibroblasts or chondrocytes (such as meniscal fibrochondrocytes, vertebral fibrochondrocytes, etc.). The scaffold, together with the ingrown cells can support natural load forces in the region.

In another embodiment, methods for fabricating a prosthetic device having in vivo the shape desired (such as a segmental defect in a meniscus, for example) is provided. The method involves obtaining a fiber matrix material from tissues of an animal lacking any functional expression of alpha-1,3-gal and placing this biocompatible and partially bioresorbable fiber matrix into a mold defining the desired shape (The mold defines the outer surface of the device to complement the desired body region.). The fibers can then be lyophilized and/or contacted with a chemical cross-linking agent such that the fibers assume the shape of the mold. Alternatively, after the molding is completed, the structure or matrix formed in the mold can be cut so that its outer surface is complementary to a segmental defect. This method can yield a matrix adapted to have an outer surface contour complementary to that of the segmental defect in the meniscus. This type of matrix can be implanted to correct a segmental defect of meniscus or as a meniscal augmentation device, the matrix can establish a biocompatible and an at least partially bioresorbable scaffold for ingrowth of meniscal fibrochondrocytes and for supporting natural meniscal load forces.

4. Hard and Soft Tissue Grafts

In another aspect of the invention, bone tendon bone grafts are provided that can be useful in orthopedic surgery. Bone tendon bone grafts can contain one or more bone blocks, and a tendon attached to the bone blocks. The bone blocks can be cut to provide a groove sufficient to accommodate a fixation screw. Alternatively, a bone tendon bone graft is provided that conatins one or more bone blocks, wherein the bone block is pre-shaped into a dowel, and a tendon attached to the bone blocks. A method to obtain bone tendon bone grafts is also prvided whereby a first bone plug having attached thereto a tendon or ligament is first excised and then a second bone plug having attached thereto a tendon or ligament is excised; such that the first bone plug and the second bone plug are derived from contiguous bone stock and overlap such that excision of the first bone plug or the second bone plug forms a groove in the bone plug that is excised subsequent to the other.

In other embodiments, bone tendon bone grafts are provided that contain a tendon and one bone block. The tendon can be looped around a bone to create a tendon, bone, tendon layer that can be held in place with sutures. This can also contain two trailing portions of the tendon available for fixation to secure the transplant. This type of graft can increase tissue strength while decreasing shear that may cause tissue failure by taking advantage of the natural cyclic creep associated with tendon movement to balance opposing forces in a pulley type fashion.

5. Skin Repair

In a further aspect of the present invention, the hard and soft tissue from animals lacking any expression of functional alpha-1,3-galactosyltransferase can be used in skin repair.

The skin can be divided into three layers: the epidermis, the dermis and the subcutaneous layer. The epidermis is divided into four layers, starting from bottom to top: the basal cell layer, stratum spinosum, stratum granulosum, and stratum corneum.

The basal cell layer of the epidermis contains basal cells which divide and differentiate into other cells in the epidermis, and melanocytes, the cells that make melanin which gives skin its color. The stratum spinosum lies above the basal cell layer and is made of keratinocytes, cells that make the protein keratin. Keratin is an important component of the stratum corneum as well as hair and nails. Cells in the stratum granulosum are flattened and contain dark granules that are expelled and provide the "cement" that holds cells together in the overlying stratum corneum. This uppermost layer of the epidermis is actually made of tightly-packed layers of dead cells filled with keratin that form the major physical barrier for the skin. The stratum corneum is thicker in areas like the palms and soles that withstand more daily wear and tear than other parts of the body. The epidermis also contains Langerhans cells, which act as part of the skin's defense against infection. The dermal-epidermal junction is where the epidermis meets the dermis. The basement membrane zone serves as the "glue" between these two layers.

The dermis is divided into the upper papillary dermis and the lower reticular dermis. The structural components of the dermis include collagen, elastic fibers, and ground substance. Nerves and blood vessels also course through the dermis. Skin appendages are the eccrine and apocrine sweat glands, hair follicles, sebaceous glands, and nails. Except for nails, all the skin appendages are located in the dermis.

The release of sweat from eccrine glands is the body's cooling process. Sweat is produced in a coiled tubule in the dermis and is transported by a sweat duct through the epidermis to be secreted. The entire body surface has about 2-3 million eccrine sweat glands and can produce up to 10 L of sweat per day.

In humans, apocrine sweat glands serve no known function and are regarded as vestigial glands perhaps useful to our ancestors. They are located mainly in the underarm and genital areas. Like eccrine sweat, apocrine sweat is also produced in coiled tubules in the dermis, but the apocrine duct drains sweat into a hair follicle from which it reaches the skins surface.

Hair is made of keratin, the same substance that forms nails and the top layer of the epidermis (stratum corneum). Different cells located in the root of the hair make keratin and melanin, which gives hair its color. Humans have two types of hair: vellus (light and fine) and terminal (dark and thick). A sebaceous gland secretes an oily substance called sebum that drains into the canal of a hair follicle to reach the surface of the skin. Together, a hair follicle and its associated sebaceous gland are called a pilosebaceous unit. Hair follicles are distributed everywhere on the body except the palms and soles. In humans, hair is largely decorative, but it also serves a protective function. Eyebrows and eyelashes protect the eyes from dust and sun, while nasal hairs block out foreign bodies from your nose. Scalp hair provides some temperature insulation.

Sebaceous glands produce an oily substance called sebum. They are most prominent in the skin of the scalp, face, and upper trunk and are absent from the palms and soles. As part of the pilosebaceous unit, sebaceous glands secrete sebum that drains into the follicular canal and eventually onto the surface of the skin. Sebaceous glands increase in size and produce more sebum in response to increased hormone levels, specifically androgen, during adolescence. They play an important role in the development of acne.

The subcutaneous layer lies between the dermis and the underlying fascia covering muscle. This layer is made of groups of adipocytes (fat cells) that are separated by fibrous septa. It serves three main functions: to insulate the body from cold, to absorb trauma and cushion deeper tissues, and to act as storage for the body's reserve fuel.

Nails are the only skin appendages that are not located in the dermis but instead are located at the ends of fingers and toes. The nail plate is made of dead keratin, which forms a hard protective structure about 0.3-0.65 mm thick. Keratin is formed in the nail matrix by dividing epidermal cells. The nail bed is the epithelial layer that is tightly attached to the bottom of the nail plate. The blood vessels of the nail bed give nails their pink color. The proximal nail fold, or cuticle, protects the base of the nail from infection-causing organisms. Nails grow at an average rate of 0.1 mm per day, and toenails grow slower than fingernails.

In a further embodiment, the hard and soft tissue from animals lacking any expression of functional alpha-1,3-galactosyltransferase can be used in skin repair. Any component or combination of skin components derived from such animals can be used, including, but not limited to, the epidermal tissue, basal cell layer, stratum spinosum, stratum granulosum, stratum corneum, dermal tissue, upper papillary dermal tissue, lower reticular dermal tissue, collagen, elastic fibers, ground substance, eccrine glands, apocrine glands, hair follicles, sebaceous glands, nails, hair and subcutaneous tissue. Such tissue can be used to replace human skin, for example, to repair deep tissue burns of the skin.

Skin tissues include, but are not limited to, dermal or epidermal tissue or derivatives thereof. Below the skin is the fatty subcutaneous tissue. In one embodiment, the skin xenograft can include the epidermis. In another embodiment, the skin xenograft can include the epidermis and the dermis. The dermis can be provided in variable thicknesses, for example, 1, 5, 10 or 20 mm. In addition, skin grafts are provided that contain epidermis, dermis and subcutaneous tissue. In one embodiment skin graft that contain epidermis, dermis and subcutaneous tissue can be used to replace skin overlying bony areas or over tendons.

In another embodiment, skin tissue is used in its native form, or in a de-cellularized form, as a scaffold for repair or replacement of rotator cuff, intrabdominal wall repair, gynecological or urological tissue repair, as part of a process to repair or replace ligaments or tendons, or other soft tissue applications (for example as described in Table 6). The skin tissue xenograft can be a permanent replacement or used as a temporary replacement until the patient can regrow new skin. In one embodiment, the skin graft can be used as a temporary substitute, Temporary skin substitutes can heal partial-thickness burns, promote wound healing and prevent infection, and can be used if a patient in not healthy enough for reconstructive surgery. In another embodiment, permanent skin grafts are provided.

In further embodiments, different types of skin xenografts are provided. In one embodiment, the graft is a split-thickness grafts. Split-thickness grafts can contain the dermis with only a portion of the epidermis and can be used over burns or large wounds. In another embodiment, the graft is a full-thickness grafts. Full thickness grafts can include the epidermis and the dermis and can be used to cover small areas. In a further embodiment, the graft can be a pedicle flaps or grafts. Pedicle flaps or grafts can include the epidermis, the dermis and subcutaneous tissue. Pedicle flaps or grafts can be used to cover wounds or other areas that can require additional operations to repair bone, tendon, or nerve damage.

6. Internal Tissue Repair

In another aspect of the present invention, the hard and soft tissue from animals lacking any expression of functional alpha-1,3-galactosyltransferase can be used in internal tissue repair, such as hernia repair, tendon pulleys, gliding surfaces, blood vessel anastamoses, heart valve repair or replacement and dura repair. Internal tissues include pericardial tissue, heart valves and submucosal tissue. In one embodiment, the submucosal tissue can be used to repair or replace connective tissue.

In another embodiment, the xenograft tissue is prepared from a delaminated segment derived from submucosa of animal organs, preferably the organ submucosa from an alpha 1,3 GT knockout pig. In a preferred embodiment the submucosa is derived from the intestinal tissue of an animal. The segment can include the tunica submucosa and basilar tissue of the tunica mucosa, generally including the muscularis mucosa and the stratum compactum. The tunica submucosa and basilar mucosa tissue can be delaminated from the tunica muscularis and the luminal portion of the tunica mucosa of the segment of intestinal tissue. This processing can result in a tri-layer intestinal tissue segment that is tubular, very tough, fibrous, collagenous material (see, for example, U.S. Pat. Nos. 4,902,508 and 4,956,178). In another embodiment, this tissue is extracted from mature animals, such as sows that, for example weigh between 400 and 600 lbs. The tri-layer intestinal segments can be used to form xenografts or they can be cut longitudinally or laterally to form elongated tissue segments. In either form, such segments have an intermediate portion and opposite end positions and opposite lateral portions which can be formed for surgical attachment to existing physiological structures, using surgically acceptable techniques (see also U.S. Pat. No. 5,372,821). In a related embodiment, the soft tissue is derived from dermal or skin tissue, which also can be formed or cut and used for surgical attachment to existing physiological structures.

In another embodiment, the invention provides a method for preparing or processing a soft tissue for engraftment into humans. An intact portion of tissue can be removed from any tissue of the animal. In one embodiment, an intact heart can be removed from the animal and heart valve tissues can then be excised, or pericardium can be harvested. In other embodiments, tissues can include, but are not limited to, epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gamgee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue.

In one embodiment, the tissue can be collected from freshly killed animals. Alternatively, the tissue can be surgically removed from viable animals. In one embodiment, after removal, the tissue can be placed in a suitable sterile isotonic or other tissue preserving solution. Harvesting of the tissue after slaughter of the animal can be done as soon as possible after slaughter and can be performed at cold temperature. For example, between about 5° C. and about 20° C., about 0° C. and about 20° C., about 0° C. and about 10° C., or about 0° C. and about 25° C. The harvested tissues and valves can be dissected free of adjoining tissue. In one embodiment, a tissue or heart valve or portion thereof can be dissected free of adhering tissue, plaques, calcifications and the like. Alternatively, a tissue or valve can be dissected with portions of the surrounding tissue.

In one specific embodiment, tricuspid valves can be excised as separate leaflets. In another embodiment, tricuspid valves can be extracted as an intact valve including the fibrous ring surrounding the auriculo-ventricular orifice and the tendinous chords. In another embodiment, after dissection of the valve, the valve or valve portions can be supported with stents, rings and the like. In another embodiment, peritoneum or pericardium can be harvested to form a heart valve xenografts or matrix material according to procedures known to those of ordinary skill in the art. (See, for example, U.S. Pat. No. 4,755,593 by Lauren).

Soft tissue xenografts can be used in a variety of applications for the repair or reconstructions of human body parts, for example, those disclosed in Table 6.

Heart Valves

In one embodiment, heart valves are extracted from animals that lack any expression of alpha-1,3-Gal. Bovine, ovine, or porcine hearts, and specifically porcine hearts, from animals lacking any functional expression of alpha-1,3-Gal, can serve as sources of heart valves. Heart valves are composed of fibrochondrocytes and an extracellular matrix of collagen and elastic fibers, as well as a variety of proteoglycans. Types of heart valves include, but are not limited to the mitral valve, the atrial valve, the aortic valve, the tricuspid valve, pulmonary valve, plumonic patch, descending thoracic aorta, aortic non-valve conduit, pulmonic non-valve conduit with LPA and RPA, right or left pulmonary hemi-artery with or without intact cusp, saphenous vein, aortoiliac, femoral vein, femoral artery and/or semi-lunar valve In certain embodiments, tools can be used to secure a heart valve prosthesis to an aortic wall. Tools can include fasteners and/or reinforcements. In particular embodiments, heart valve prostheses can have flexible leaflets. In one embodiment, the heart valve prosthesis can be constructed from natural materials such as tissue, synthetic materials such as polymers or a combination thereof. In another embodiment, the valve prosthesis can be a tissue valve, and can additionally include a stent, or be stentless, and be of porcine, bovine, or other animal tissue source. A heart valve xenograft prepared in accordance with the invention can have the general appearance of a native heart valve xenograft. The heart valve xenograft can also be valve segments, such as individual leaflets, each of which may be implanted into receipient heart. Alternatively, porcine pericardium can be used to form the heart valve xenografts of the present invention.

The heart is a hollow, muscular organ that circulates blood throughout an animal's body by contracting rhythmically. In mammals, the heart has four-chambers situated such that the right atrium and ventricle are completely separated from the left atrium and ventricle. Normally, blood flows from systemic veins to the right atrium, and then to the right ventricle from which it is driven to the lungs via the pulmonary artery. Upon return from the lungs, the blood enters the left atrium, and then flows to the left ventricle from which it is driven into the systematic arteries.

Four main heart valves prevent the backflow of blood during the rhythmic contractions: the tricuspid, pulmonary, mitral, and aortic valves. The tricuspid valve separates the right atrium and right ventricle, the pulmonary valve separates the right atrium and pulmonary artery, the mitral valve separates the left atrium and left ventricle, and the aortic valve separates the left ventricle and aorta. Generally, patients having an abnormality of a heart valve are characterized as having valvular heart disease.

A heart valve can malfunction either by failing to open properly (stenosis) or by leaking (regurgitation). For example, a patient with a malfunctioning aortic valve can be diagnosed with either aortic valve stenosis or aortic valve regurgitation. In either case, valve replacement by surgical means is a possible treatment. Replacement valves can be autografts, allografts, or xenografts as well as mechanical valves or valves made partly from pig valves. Interestingly, cryopreserved allografts remain viable within the recipient patient for many years after transplantation. Unfortunately, replacement valves are susceptible to problems such as degeneration, thrombosis, and calcification.

The heart valve xenograft of the invention, or a segment thereof, can be implanted into damaged human or animal hearts by those of skill in the art using known surgical techniques, for example, by open heart surgery, or minimally invasive techniques such as endoscopic surgery, and transluminal implantation. Specific instruments for performing such surgical techniques are known to those of skill in the art, which ensure accurate and reproducible placement of heart valve implants.

In a particular embodiment, heart valves as a prosthesis can be used for patients with various forms of disease to the heart and/or valve. Porcine hearts can be obtained from market weight pigs (for example, pigs greater than 120 kg). After rinsing in sterile phosphate buffered saline, the hearts can be field dissected (apex removed) and shipped at 4° C. in sterile PBS. All hearts can arrive at the processing center, for example, within 24 hr of animal slaughter. Aortic and pulmonary valves can be dissected as roots. In a specific embodiment, these tissues can be subjected to a bioburden reduction step of incubation in a mixture of antibiotics and antimycotics for aproximately 48 hr at approximately 48° C. The disinfected tissues can either be cryopreserved (for example in 10% (v/v) DMSO and 10% (v/v) fetal bovine serum, −1° C./min) or can be decellularized by a procedure involving treatment with hypotonic medium followed by digestion with a mixture of deoxyribonuclease I and ribonuclease A. After 12 days, the decellularized valves can either be cryopreserved or chemically fixed, for example, in 0.35% (w/v) glutaraldehyde at 2 mmHg in phosphate buffered saline (pH 7.4) for a total of 7 days (the low pressure fixation ensures maintenance of the natural crimp of the collagen matrix). In one embodiment, the fixed tissues is not cryopreserved, but can be stored in a cross-fixing solution, such as a glutaraldehyde solution (such as 0.35% gluteraldehyde).

A tissue-based valve prosthesis can maintain structural elements, such as leaflets, from its native form and/or structural elements can be incorporated into the prosthesis from the assembly of distinct pieces of tissue. For example, the valve prosthesis can be assembled from a porcine heart valve, from bovine pericardium or from a combination thereof. Porcine tissue valves, for example, the Toronto SPV™ valve marketed by St. Jude Medical, Inc. St. Paul, Minn., can be implanted in the patient using the tools described herein. The Toronto SPV.RTM. valve is designed for implantation in an aortic heart valve position, see, for example, David et al., J. Heart Valve Dis. 1:244-248 (1992). The tools of the present invention are applicable to any valve, especially any tissue valve prosthesis, that is adapted for implanting in a patient.

Heart valve prosthesis includes a harvested tissue valve, such as a crosslinked porcine valve. Prosthesis can further include a sewing cover. The valve can have three leaflets, which can include a generally cylindrical base and three commissures support the leaflets.

In further embodiments, fasteners can be used to secure an heart valve, such as an aortic valve, prosthesis to the vessel wall. The fasteners can be generally secured to the vessel wall during the implantation procedure of the heart valve prosthesis. The fasteners can have a shape similar to a needle or nail, although the fastener can alternatively have a plurality of sharp tips. In addition, the fasteners can have one or more barbs near the tips of the fasteners. The fastener can include an elongated portion with a tip end. The fastener can also have an optional head at the end opposite tip end. In other embodiments, a barb can be located at or near tip end. Fasteners can include two or more barbs extending from the same or different sides of fastener. The fasteners can be formed from a biocompatible material. Preferable biocompatible materials for the fasteners yield the desired mechanical properties with respect to, for example, durability, mechanical strength, and flexibility/rigidity. Fasteners can be sufficiently rigid to hold their shape when pressure is applied by a physician to insert the fastener. A fastener that is not sufficiently rigid may bend when pressure is applied for insertion. Some bending may be tolerable as long as the fastener is able to penetrate the materials. A fastener without sufficient rigidity may not insert properly, thus increasing the propensity of prosthesis damage, aortic wall damage, improper attachment of the prosthesis and/or increased cross-clamp times. After implantation, the fasteners can remain in the patient to secure the valve prosthesis for the life-span of the prosthesis or at least until the healing process secures the valve to the vessel through cellular growth, if a bioresorbable material is used for the fastener. The fasteners can be made from, for example, metal, ceramic, polymers or combinations thereof. Suitable metals include, for example, titanium and stainless steel. Suitable ceramics include, for example, hydroxyapatite, such as bone fragments, carbon materials, such as graphite, and alumina. Suitable polymers include sufficiently rigid polymers, such as polyetheretherketone (PEEK). The fasteners can also be formed from bioresorbable polymers, as described above, such that over time the fasteners are resorbed after sufficient tissue has been generated to secure the valve prosthesis without the fasteners.

The length of the fastener can be between about 2 millimeters (mm) and about 8 mm, for example, about 4 mm to about 7 mm. In one embodiment, the diameter of the elongated portion of the fastner can be less than about 2 mm, for example between about 0.2 mm and about 1.5 mm or between about 0.2 mm and about 1 mm.

In other embodiments, methods of attaching a heart valve prosthesis to a vessel wall can be based on the fasteners and the reinforcements described above. The reinforcements themselves can be secured either with the fastener or other device. The fasteners can be deployed to secure all of the elements simultaneously or one or more components can be associated with each other or the valve prosthesis prior to the final deployment of the fasteners.

In one embodiment, the heart valves can be inserted into the heart, for example, during an open heart procedure. In one embodiment, the process can initiated by placing the subject, such as a human patient or primate or other large animal model, such as a sheep, on appropriate life support and by opening the chest cavity to make the heart accessible. Then, a transverse aortotomy can be performed to make the natural valve accessible through the vessel, such as the aorta. In one embodiment, the vessel is the aorta and the location for opening the aorta can depend on precise structure of the prosthesis. For typical prosthesis, the aorta generally can be cut about 1 cm from the sinotubular junction. The damaged or diseased natural valve is removed, preferably along with all calcium and calcific debris. The aortic valve prosthesis can be placed between the aortic annulus, a slight narrowing where the aorta joins the heart, and the sinotubular junction, a slight narrowing of the aorta just down stream from the coronary arteries. However, the prosthesis can extend beyond the aortic annulus and/or the sinotubular junction. For placement at the aortic annulus, the prosthesis can be parachuted down the severed aorta.

In additional embodiments, the heart valve prosthesis can be positioned at the site of implantation, adjacent to the appropriate vasculature, for example, the aorta. In one embodiment, the inflow edge of the valve can be sutured or otherwise secured prior to securing the outflow edge with the fasteners described herein, although the inflow edge can be secured after the outflow edge. In addition, it may be desirable to tack the commissures in place prior to application of the fasteners described herein. In a particular embodiment, the fasteners, the reinforcements, if any, and the prosthesis can be separate at the start of the implantation procedure. Alternatively, the elements can be pre-assembled. In another embodiment, once the prosthesis is properly aligned, a reinforcement can be placed in position and fasteners can be sequentially inserted into an aperture in the reinforcement, through the prosthesis and through the aortic wall. When all the fasteners have been inserted through one reinforcement, any additional reinforcements are similarly secured with fasteners. The fasteners can be inserted using finger pressure, forceps, a pusher tool, a hammer, or the like. Specific forceps can be used that specifically interface with the head of a fastener. If there are no reinforcements, the fasteners are placed in a desired position and similarly inserted through the prosthesis and aortic wall.

In some embodiments, fasteners can be inserted into reinforcements prior to the initiation of the implantation procedure. The reinforcements can be supplied to the surgeon with the fasteners inserted through or partly through apertures in the reinforcement. In these embodiments, the head or blunt end of the fasteners can stick out from the surface of the reinforcements. Thus, the procedure can be somewhat simplified relative to a procedure in which all of the components are separate prior to beginning the procedure. In these embodiments, once the prosthesis is correctly positioned in the vessel, a reinforcement with fasteners can be aligned at a desired location, and the fasteners can be directly deployed by pushing the fastener through the prosthesis and through the wall of the aorta. The fasteners can be inserted sequentially, and a plurality of reinforcements can be secured in this approach.

In alternative embodiments, one or more reinforcements can be attached to the prosthesis prior to beginning the implantation procedure. The reinforcements can be secured to the prosthesis by the manufacturer. Suture, biocompatible adhesive or other suitable fastener can be used to secure a reinforcement to the prosthesis. Suitable biocompatible adhesives include, for example, fibrin glue and other surgical glues. Once the prosthesis is correctly positioned, fasteners can be sequentially or simultaneously placed within an aperture in the reinforcement and inserted through the prosthesis and the wall of the aorta. This can be continued until all of the fasteners are deployed.

In still other embodiments, the prostheses can be supplied with reinforcements in place and fasteners inserted in the reinforcements. The reinforcements can be secured to the prosthesis using the fastener inserted through the reinforcement and, at least, partly through the prosthesis. Alternatively, the reinforcement can be secured to the prosthesis using suture, adhesive or other fastener. Once the prosthesis is in place within the animal or patient, each fastener can be pushed through the wall of the vessel to secure the prosthesis. In other embodiments, conventional sutures, while effective and straightforward, can be used as fastners.

7. Additional Applications for Xenografts

In a further aspect of the present invention, the tissue products derived from animals lacking expression of functional alpha-1,3-GT can be used to reconstruct body parts of a human. In certain embodiments, decellularized or cellularized dermal tissue, bone, ligaments, tendons, heart valves, nucleus pulposa, cartilage, meniscus, blood vessels, pericardium or other tissues described herein can be used, for example, as described in Table 6. In particular embodiments, the tissue can be used for human orthopedic reconstruction or repair, such as rotator cuff repair, human skin repair, and/or human soft tissue repair. The xenografts can be tested in a variety of animal models, such as primate or non-primate, such as sheep, models.

The xenografts can be applied using routine surgical procedures commonly employed for tissue graft applications. In one embodiment, for example, for use in non-vascular tissue graft applications, the tubular graft material can be cut longitudinally and rolled out to form a "patch" of tissue. In another embodiment, tissue delamination can be carried out on "patches" of tissue, such as intestinal tissue, prepared by cutting the intestinal segment longitudinally and "unrolling" it to form a pre-graft patch. The prepared graft tissue patches can be utilized, for example, as a skin graft material, for dura repair, or for repair of other body tissue defects lending themselves to surgical application of a tissue graft patch having the physical and functional characteristics of the present graft composition.

TABLE 6

Applications/Uses of Tissues harvested from Animals lacking any expression of functional alpha-1,3-GT Dermal Tissue, cellularized or de-cellularized
Applications:

Hernia
Abdominal wall repair
Rotator cuff repair
Slings to treat urinary incontinence
Cosmetic surgery including breast reconstruction, facial defects, lip reconstruction, eyelid spacer grafts, depressed scar repair,
Burns, skin replacement
Mucosal grafts
Nasolabial folds
Oral resurfacing
Parotidectomy
Rhinoplasty
Septal perforation repair
Temporary wound dressing
Wound coverage
Tympanoplasty
Vestibuloplasty
Other soft tissue defects
Dermal tissue can be combined with the following additional materials:

Growth factors to facilitate faster healing, recruitment of cells (scaffold), in combination to promote hemostasis
Anti-scarring (fibrinogen, Fibrin 1)
Bone
Applications:

Use in fracture and small skeletal defect repair and osseous defects, gaps in bone, spinal repair, maxilliofacial reconstruction, dental implants
Paste
Bone plugs
Bone implants
Chips
Screws
Rings (humeral, fibular, machined wedge)
Dowels (unicortical, threaded cortical dowel,)
Blocks (tricortical iliac block, unicortical block, bicortical block, cancellous block)
Wedges (cortical wedge, patellar cortical wedge)
Moldable strips
Cancellous chips
Powder
Vetebral fusions
Femoral shafts
Hemi femoral shafts
Fibular shafts
Humeral shafts
Tibial shafts TABLE 6-continued Applications/Uses of Tissues harvested from Animals lacking any expression of functional alpha-1,3-GT Ilium strip tricordical
Cancellous cortical strips
Cortical strips
Intercalary grafts including femoral head with or without cartilage, whole or partial femur, proximal or distal femur, proximal or distal tibia
Cortical cancellous chips
Total joint replacement
Demineralized bone matrix
Lordotic cortical block
Bone tissue can be combined with any of the following additional materials:

Growth factors (BMP) for non-union fracture repair
Porcine gelatin as a delivery matrix
Ligaments/Tendons
Applications:

ACL repair/replacement
PCL repair/replacement
Patellar tendon including bone
Posterior tibialis tendon
Anterior tibialis tendon
Semitendonosis tendon
Gracilis tendon
Heart Valves
Applications/Types:

Repair/replacement
Aortic valve
Pulmonary valve
Plumonic patch
Descending thoracic aorta
Aortic non-valve conduit
Pulmonic non-valve conduit with LPA and RPA
Right/Left Pulmonary Hemi-artery with or without intact cusp
Saphenous vein
Aortoiliac
Femoral vein
Femoral artery
Heart valves can be combined with any of the following additional materials:

Use of a ring material for surgical insertion
Nucleus Pulposa
Applications:

Inter-vertebral repair/replacement
Cartilage (cells)
Applications:

Cartilage replacement (replacement or as a scaffold to promote new cartilage growth).
Cartilage can be combined with any of the following additional materials:

Growth factors to promote cellular infiltration
Meniscus
Applications:

Repair/replacement
Meniscus lateral with bone bridge
Meniscus medial with bone bridge
Meniscus can be combined with any of the following additional materials:

Plastic or metals to facilitate implantation
Blood Vessels
Applications:

Replacement/repair of blood vessels, excluding those blood vessels associated with, or an integral part of, whole organs for transplantation.
Carotid artery replacement/repair
Pericardium
Applications:

Patch used in surgical procedures when tissue regeneration is needed; works as a stabilizing and protective barrier at a surgical

TABLE 6-continued

Applications/Uses of Tissues harvested from Animals lacking any expression of functional alpha-1,3-GT site Combination of other materials:
Growth factors to facilitate faster healing, recruitment of cells (scaffold), in combination to promote hemostasis
Anti-scarring (fibrinogen, Fibrin 1)
Small Intestine Submucosa
Applications:

rotator cuff repair
hernia
abdominal wall repair
slings to treat urinary incontinence
burns
skin replacement
cosmetic surgery including breast reconstruction, facial defects, lip reconstruction, eyelid spacer grafts, depressed scar repair, mucosal grafts, nasolavial folds, oral resurfacing, parotidectomy, septal perforation repair, rhinoplasty
temporary wound dressing, wound coverage
tympanoplasty
vestibuloplasty
other soft tissue defects
vascular grafts, including venous, arterial or capillary
Other Soft Tissues HTO wedge to correct valgus and varus misalignment
Fascia used to correct uninary incontinence

II. Animals Lacking any Expression of Functional Alpha-1,3-Galactosyltransferase Tissues from animals that lack any functional expression of alpha-1,3-galactosyltransferase are provided. In one embodiment, the animal is a porcine. In another embodiment, the animal is a bovine or an ovine. In other embodiments, animals are provided in which one allele of the alpha-1,3-GT gene is inactivated via a genetic targeting event. In another aspect of the present invention, animals are provided in which both alleles of the alpha-1,3-GT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can be inserted.

Animals besides old world monkeys and humans, such as pigs, that possess two inactive alleles of the alpha-1,3-GT gene are not naturally occurring. It was surprisingly discovered that while attempting to knockout the second allele of the alpha-1,3-GT gene through a genetic targeting event, a point mutation was identified, which rendered the second allele inactive.

Thus, in another aspect of the present invention, the alpha-1,3-GT gene can be rendered inactive through at least one point mutation. In one embodiment, one allele of the alpha-1,3-GT gene can be rendered inactive through at least one point mutation. In another embodiment, both alleles of the alpha-1,3-GT gene can be rendered inactive through at least one point mutation. In one embodiment, this point mutation can occur via a genetic targeting event. In another embodiment, this point mutation can be naturally occurring. In one specific embodiment the point mutation can be a T-to-G mutation at the second base of exon 9 of the alpha-1,3-GT gene. Pigs carrying a naturally occurring point mutation in the alpha-1,3-GT allow for the production of alpha1,3GT-deficient pigs free of antibiotic-resistance genes and thus have the potential to make a safer product for human use. In other embodiments, at least two, at least three, at least four, at least five, at least ten or at least twenty point mutations can exist to render the alpha-1,3-GT gene inactive. In other embodiments, pigs are provided in which both alleles of the alpha-1,3-GT gene contain point mutations that prevent any expression of functional alpha1,3GT. In a specific embodiment, pigs are provided that contain the T-to-G mutation at the second base of exon 9 in both alleles of the alpha-1,3-GT gene.

Another aspect of the present invention provides an animal, in which both alleles of the alpha-1,3-GT gene are inactivated, whereby one allele is inactivated by a genetic targeting event and the other allele is inactivated via a naturally occurring point mutation. In one embodiment, a porcine animal is provided, in which both alleles of the alpha-1,3-GT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the alpha-1,3-GT gene are inactivated, whereby one allele is inactivated via a targeting construct directed to Exon 9 and the other allele is inactivated due to presence of a T-to-G point mutation at the second base of exon 9.

Genetic Targeting of the Alpha-1,3-GT Gene

Animal cells that can be genetically modified can be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In one embodiment of the invention, cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts.

In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF). In a preferred embodiment, the cells can be fibroblasts; in one specific embodiment, the cells can be fetal fibroblasts. Fibroblast cells are a preferred somatic cell type because they can be obtained from developing fetuses and adult animals in large quantities. These cells can be easily propagated in vitro with a rapid doubling time and can be clonally propagated for use in gene targeting procedures.

Targeting Constructs

Homologous Recombination

Homologous recombination permits site-specific modifications in endogenous genes and thus novel alterations can be engineered into the genome. In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati et al., Proc. Natl. Acad. Sci. USA 81:3153-3157, 1984; Kucherlapati et al., Mol. Cell. Bio. 5:714-720, 1985; Smithies et al, Nature 317:230-234, 1985; Wake et al., Mol. Cell. Bio. 8:2080-2089, 1985; Ayares et al., Genetics 111:375-388, 1985; Ayares et al., Mol. Cell. Bio. 7:1656-1662, 1986; Song et al., Proc. Natl. Acad. Sci. USA 84:6820-6824, 1987; Thomas et al. Cell 44:419-428, 1986; Thomas and Capecchi, Cell 51: 503-512, 1987; Nandi et al., Proc. Natl. Acad. Sci. USA 85:3845-3849, 1988; and Mansour et al., Nature 336:348-352, 1988. Evans and Kaufman, Nature 294:146-154, 1981; Doetschman et al., Nature 330: 576-578, 1987; Thoma and Capecchi, Cell 51:503-512, 4987; Thompson et al., Cell 56:316-321, 1989.

One aspect of the present invention uses homologous recombination to inactivate the alpha-1,3-GT gene in cells, such as the cells described above. The DNA can comprise at least a portion of the gene(s) at the particular locus with introduction of an alteration into at least one, optionally both copies, of the native gene(s), so as to prevent expression of functional alpha1,3GT. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Targeting Vectors

Modification of a targeted locus of a cell can be produced by introducing DNA into the cells, where the DNA has homology to the target locus and includes a marker gene, allowing for selection of cells comprising the integrated construct. The homologous DNA in the target vector will recombine with the chromosomal DNA at the target locus. The marker gene can be flanked on both sides by homologous DNA sequences, a 3' recombination arm and a 5' recombination arm. Methods for the construction of targeting vectors have been described in the art, see, for example, Dai et al., Nature Biotechnology 20: 251-255, 2002; WO 00/51424.

Various constructs can be prepared for homologous recombination at a target locus. The construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of the porcine alpha-1,3-GT gene (see, for example, GenBank Acc. No. L36152, WO0130992 to The University of Pittsburgh of the Commonwealth System of Higher Education; WO 01/123541 to Alexion, Inc.).

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The DNA constructs can be designed to modify the endogenous, target alpha1,3GT. The homologous sequence for targeting the construct can have one or more deletions, insertions, substitutions or combinations thereof. The alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. Proc. Nat'l Acad. Sci. U.S.A. 84:6820-6824 (1987); Sambrook, J., et al., Molecular Cloning—A Laboratory Manual, Cold Spring Harbor Laboratory, Cold Spring Harbor, N.Y. (1989), Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, J. Mol. Appl. Genet. 1:327-341 (1982)); and the hygromycin resistance gene (hyg) (Nucleic Acids Research 11:6895-6911 (1983), and Te Riele, H., et al., Nature 348:649-651 (1990)). Other selectable marker genes include: acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. No. 6,080,576; U.S. Pat. No. 6,136,566; Niwa et al., J. Biochem. 113:343-349 (1993); and Yoshida et al., Transgenic Research 4:277-287 (1995)).

Combinations of selectable markers can also be used. For example, to target alpha1,3GT, a neo gene (with or without its own promoter, as discussed above) can be cloned into a DNA sequence which is homologous to the alpha-1,3-GT gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the alpha-1,3-GT gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. The mutation can be a subtle change, not exceeding about 5% of the homologous flanking sequences. Where mutation of a gene is desired, the marker gene can be inserted into an intron or an exon.

The construct can be prepared in accordance with methods known in the art, various fragments can be brought together, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

The present invention further includes recombinant constructs containing sequences of the alpha-1,3-GT gene. The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia), viral origin vectors (M13 vectors, bacterial phage 1 vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8). Other vectors include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof. Additional vectors that can be used include: pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen), pTrxFus, pThioHis, pLEX, pTrcHis, pTrcHis2, pRSET, pBlueBacHis2, pcDNA3.1/His, pcDNA3.1(-)/Myc-His, pSecTag, pEBVHis, pPIC9K, pPIC3.5K, pAO815, pPICZ, pPICZ☐, pGAPZ, pGAPZ☐, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis; pCR3.1, pCR2.1, pCR3.1-Uni, and pCRBac from Invitrogen; ☐ ExCell, ☐ gt11, pTrc99A, pKK223-3, pGEX-1☐T, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, □SCREEN-1, □BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBACgus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, p□gal-Basic, p□gal-Control, p□gal-Promoter, p□gal-Enhancer, pCMV□, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, □gt10, □gt11, pWE15, and □TriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRT□GAL, pNEO□GAL, pRS403, pRS404, pRS405, pRS406, pRS413, pRS414, pRS415, and pRS416 from Stratagene and variants or derivatives thereof. Two-hybrid and reverse two-hybrid vectors can also be used, for example, pPC86, pDBLeu, pDB-Trp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof. Any other plasmids and vectors may be used as long as they are replicable and viable in the host.

Techniques which can be used to allow the DNA construct entry into the host cell include calcium phosphate/DNA co precipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., Methods in Enzymology Vol. 185, pp. 527-537 (1990).

In one specific embodiment, heterozygous knockout cells can be produced by transfection of primary fetal fibroblasts with a knockout vector containing alpha-1,3-GT sequence isolated from isogenic DNA. As described in Dai et al. (Nature Biotechnology, 20:451-455), the 5' arm can be 4.9 kb and be comprised of a large fragment of intron 8 and the 5' end of exon 9. The 3' arm can be and be comprised of exon 9 sequence. The vector can incorporate a promoter trap strategy, using, for example, IRES (internal ribosome entry site) to initiate translation of the Neor gene.

Selection of Homologously Recombined Cells

The cells can then be grown in appropriately-selected medium to identify cells providing the appropriate integration. The presence of the selectable marker gene inserted into the alpha-1,3-GT gene establishes the integration of the target construct into the host genome. Those cells which show the desired phenotype can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the alpha-1,3-GT gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is known in the art, see, for example, Kim and Smithies, Nucleic Acids Res. 16:8887-8903, 1988; and Joyner et al., Nature 338:153-156, 1989. The specific combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, 1983.

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

Induced Mutation in the Alpha 1,3 GT Locus

In certain other embodiments, the methods of the invention involve the intentional introduction of a mutation via a mutagenic agent. Examples of mutagenic agents known in the art and suitable for use in the present invention include, but are not limited to, chemical mutagens (e.g., DNA-intercalating or DNA-binding chemicals such as N-ethyl-N-nitrosourea (ENU), ethylmethanesulphonate (EMS), mustard gas, ICR191 and the like; see, e.g., E. C. Friedberg, G. C. Walker, W. Siede, DNA Repair and Mutagenesis, ASM Press, Washington D.C. (1995), physical mutagens (e.g., UV radiation, radiation, x-rays), biochemical mutagens (e.g., restriction enzymes, DNA repair mutagens, DNA repair inhibitors, and error-prone DNA polymerases and replication proteins), as well as transposon insertion. According to the methods of the present invention, cells in culture can be exposed to one of these agents, and any mutation resulting in the depletion of galactose alpha1,3-galactose on the cell surface can be selected, for example, via exposure to toxin A.

Preferred doses of chemical mutagens for inducing mutations in cells are known in the art, or can be readily determined by the ordinarily skilled artisan using assays of mutagenesis known in the art. Chemical mutagenesis of cells in vitro can be achieved by treating the cells with various doses of the mutagenic agent and/or controlling the time of exposure to the agent. By titrating the mutagenic agent exposure and/or dose, it is possible to carry out the optimal degree of mutagenesis for the intended purpose, thereby mutating a desired number of genes in each target cell. For example, useful doses of ENU can be 0.1-0.4 mg/ml for approximately 1-2 hours. In another example, useful doses of EMS can be 0.1-1 mg/ml for approximately 10-30 hours. In addition, lower and higher doses and exposure times can also be used to achieve the desired mutation frequency.

Identification of Cells that do not Express Functional Alpha-1,3-GT

In one embodiment, the selection procedure can be based on a bacterial toxin to select for cells that lack expression of functional alpha1,3GT. In another embodiment, the bacterial toxin, toxin A produced by *Clostridium difficile*, can be used to select for cells lacking the cell surface epitope galactose alpha1,3-galactose. Exposure to *C. difficile* toxin can cause rounding of cells that exhibit this epitope on their surface, releasing the cells from the plate matrix. Both targeted gene knockouts and mutations that disable enzyme function or expression can be detected using this selection method. Cells lacking cell surface expression of the galactose alpha 1,3-galactose epitope, identified using Toxin A mediated selection described, or produced using standard methods of gene inactivation including gene targeting, can then be used to produce animals, in which both alleles of the alpha 1,3 GT gene are inactive.

In one embodiment, the selection method can detect the depletion of the alpha 1,3GT epitope directly, whether due to targeted knockout of the alpha 1,3GT gene by homologous recombination, or a mutation in the gene that results in a nonfunctioning or nonexpressed enzyme. Selection via antibiotic resistance has been used most commonly for screening (see above). This method can detect the presence of the resistance gene on the targeting vector, but does not directly indicate whether integration was a targeted recombination event or a random integration. Certain technology, such as Poly A and promoter trap technology, increase the probability of targeted events, but again, do not give direct evidence that the desired phenotype, a cell deficient in gal alpha 1,3 gal epitopes on the cell surface, has been achieved. In addition, negative forms of selection can be used to select for targeted integration; in these cases, the gene for a factor lethal to the cells is inserted in such a way that only targeted events allow the cell to avoid death. Cells selected by these methods can then be assayed for gene disruption, vector integration and, finally, alpha 1,3gal epitope depletion. In these cases, since the selection is based on detection of targeting vector integration and not at the altered phenotype, only targeted knockouts, not point mutations, gene rearrangements or truncations or other such modifications can be detected.

In another embodiment, the selection procedure can be conducted using serum containing complement factors and natural antibodies to the gal alpha1,3gal epitope (see, for example, Koike et al., Xenotransplantation 4:147-153, 1997). Exposure to serum from a human or non-human primate that contains anti-Gal antibodies can cause cell lysis due to specific antibody binding and complement activation in cells that exhibit gal alpha 1,3 gal epitope. Therefore, cells deficient in alpha-1,3-GT will remain alive and thus can be selected.

Animal cells believed to lacking expression of functional alpha-1,3-GT can be further characterized. Such characterization can be accomplished by the following techniques, including, but not limited to: PCR analysis, Southern blot analysis, Northern blot analysis, specific lectin binding assays, and/or sequencing analysis.

PCR analysis as described in the art (see, for example, Dai et al. Nature Biotechnology 20:431-455) can be used to determine the integration of targeting vectors. In one embodiment, amplimers can originate in the antibiotic resistance gene and extend into a region outside the vector sequence. Southern analysis (see, for example, Dai et al. Nature Biotechnology 20:431-455) can also be used to characterize gross modifications in the locus, such as the integration of a targeting vector into the alpha 1,3GT locus. Whereas, Northern analysis can be used to characterize the transcript produced from each of the alleles.

Specific lectin binding, using GSL IB4 lectin from Griffonia (Bandeiraea) simplicifolia (Vector Labs), a lectin that specifically binds the carbohydrate moiety gal alpha 1,3 gal, and FACS (fluorescent antibody cell sorting) analysis of binding can determine whether or not the alpha 1,3 gal epitope is present on the cells. This type of analysis involves the addition of fluorescein-labeled GSL-IB4 lectin to the cells and subsequent cell sorting.

Further, sequencing analysis of the cDNA produced from the RNA transcript can also be used to determine the precise location of any mutations in the alpha 1,3GT allele.

In yet another aspect, the present invention provides a method for producing viable animals, such as pigs, in which both alleles of the alpha-1,3-GT gene have been rendered inactive. In one embodiment, the animals are produced by cloning using a donor nucleus from a cell in which both alleles of the alpha-1,3-GT gene have been inactivated. In one embodiment, both alleles of the alpha-1,3-GT gene are inactivated via a genetic targeting event. In another embodiment, both alleles of the alpha-1,3-GT gene are inactivated due to the presence of a point mutation. In another embodiment, one allele is inactivated by a genetic targeting event and the other allele is inactivated via a point mutation. In a further embodiment, one allele is inactivated by a genetic targeting event and the other allele is inactivated due to presence of a T-to-G point mutation at the second base of exon 9 of the alpha-1,3-GT gene. In a specific embodiment, one allele is inactivated via a targeting construct directed to Exon 9 and the other allele is inactivated due to presence of a T-to-G point mutation at the second base of exon 9 of the alpha-1,3-GT gene. In another embodiment, a method to clone such animals, for example, pigs, includes: enucleating an oocyte, fusing the oocyte with a donor nucleus from a cell in which both alleles of the alpha-1,3-GT gene have been inactivated, and implanting the nuclear transfer-derived embryo into a surrogate mother.

Alternatively, a method is provided for producing viable aniamls that lack any expression of functional alpha-1,3-GT by inactivating both alleles of the alpha-1,3-GT gene in embryonic stem cells, which can then be used to produce offspring.

Genetically altered animals that can be created by modifying zygotes directly. For mammals, the modified zygotes can be then introduced into the uterus of a pseudopregnant female capable of carrying the animal to term. For example, if whole animals lacking the alpha-1,3-GT gene are desired, then embryonic stem cells derived from that animal can be targeted and later introduced into blastocysts for growing the modified cells into chimeric animals. For embryonic stem cells, either an embryonic stem cell line or freshly obtained stem cells can be used.

In a suitable embodiment of the invention, the totipotent cells are embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992). In another suitable embodiment of the invention, the totipotent cells are embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359:550-551 (1992)). The cultivation of EG cells can be carried out using methods described in the article by Donovan et al., "Transgenic Animals, Generation and Use," Ed. L. M. Houdebine, Harwood Academic Publishers (1997), and in the original literature cited therein.

Tetraploid blastocysts for use in the invention may be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art. A suitable method for the purposes of the present invention is the microinjection method as described by Wang et al., EMBO J. 10:2437-2450 (1991).

Alternatively, by modified embryonic stem cells transgenic animals can be produced. The genetically modified embryonic stem cells can be injected into a blastocyst and then brought to term in a female host mammal in accordance with conventional techniques. Heterozygous progeny can then be screened for the presence of the alteration at the site of the target locus, using techniques such as PCR or Southern blotting. After mating with a wild-type host of the same species, the resulting chimeric progeny can then be cross-mated to achieve homozygous hosts.

After transforming embryonic stem cells with the targeting vector to alter the alpha-1,3-GT gene, the cells can be plated onto a feeder layer in an appropriate medium, e.g., fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified alpha-1,3-GT gene.

Somatic Cell Nuclear Transfer to Produce Cloned, Transgenic Offspring

The present invention provides a method for cloning an animal, such as a pig, lacking a functional alpha-1,3-GT gene via somatic cell nuclear transfer. In general, the animal can be produced by a nuclear transfer process comprising the following steps: obtaining desired differentiated cells to be used as a source of donor nuclei; obtaining oocytes from the animal; enucleating said oocytes; transferring the desired differentiated cell or cell nucleus into the enucleated oocyte, e.g., by fusion or injection, to form NT units; activating the resultant NT unit; and transferring said cultured NT unit to a host animal such that the NT unit develops into a fetus.

Nuclear transfer techniques or nuclear transplantation techniques are known in the art (Dai et al. Nature Biotechnology 20:251-255; Polejaeva et al Nature 407:86-90 (2000); Campbell et al, Theriogenology, 43:181 (1995); Collas et al, Mol. Report Dev., 38:264-267 (1994); Keefer et al, Biol. Reprod., 50:935-939 (1994); Sims et al, Proc. Natl. Acad. Sci., USA, 90:6143-6147 (1993); WO 94/26884; WO 94/24274, and WO 90/03432, U.S. Pat. Nos. 4,944,384 and 5,057,420).

A donor cell nucleus, which has been modified to alter the alpha-1,3-GT gene, is transferred to a recipient oocyte. The use of this method is not restricted to a particular donor cell type. The donor cell can be as described herein, see also, for example, Wilmut et al Nature 385 810 (1997); Campbell et al Nature 380 64-66 (1996); Dai et al., Nature Biotechnology 20:251-255, 2002 or Cibelli et al Science 280 1256-1258 (1998). All cells of normal karyotype, including embryonic, fetal and adult somatic cells which can be used successfully in nuclear transfer can be employed. Fetal fibroblasts are a particularly useful class of donor cells. Generally suitable methods of nuclear transfer are described in Campbell et al Theriogenology 43 181 (1995), Dai et al. Nature Biotechnology 20:251-255, Polejaeva et al Nature 407:86-90 (2000), Collas et al Mol. Reprod. Dev. 38 264-267 (1994), Keefer et al Biol. Reprod. 50 935-939 (1994), Sims et al Proc. Nat'l. Acad. Sci. USA 90 6143-6147 (1993), WO-A-9426884, WO-A-9424274, WO-A-9807841, WO-A-9003432, U.S. Pat. No. 4,994,384 and U.S. Pat. No. 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell et al (Nature, 380:64-68, 1996) and Stice et al (Biol. Reprod., 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus, or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells or endothelial cells. In another embodiment, the nuclear donor cell is an embryonic stem cell. In a preferred embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (G0, G1, G2, S, M) so as to ensure coordination with the acceptor cell. Any method known in the art may be used to manipulate the cell cycle phase. Methods to control the cell cycle phase include, but are not limited to, G0 quiescence induced by contact inhibition of cultured cells, G0 quiescence induced by removal of serum or other essential nutrient, G0 quiescence induced by senescence, G0 quiescence induced by addition of a specific growth factor; G0 or G1 quiescence induced by physical or chemical means such as heat shock, hyperbaric pressure or other treatment with a chemical, hormone, growth factor or other substance; S-phase control via treatment with a chemical agent which interferes with any point of the replication procedure; M-phase control via selection using fluorescence activated cell sorting, mitotic shake off, treatment with microtubule disrupting agents or any chemical which disrupts progression in mitosis (see also Freshney, R. I,. "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of an animal. A readily available source of oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period". In certain embodiments, the oocyte is obtained from a gilt. A "gilt" is a female pig that has never had offspring. In other embodiments, the oocyte is obtained from a sow. A "sow" is a female pig that has previously produced offspring.

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated animal 35 to 48, or 39-41, hours past the onset of estrus or past the injection of human chorionic gonadotropin (hCG) or similar hormone. The oocyte can be placed in an appropriate medium, such as a hyalurodase solution.

After a fixed time maturation period, which ranges from about 10 to 40 hours, about 16-18 hours, about 40-42 hours or about 39-41 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, Wister Inot. Symp. Monogr., 9, 19, 1969). Also, the nucleus can be injected directly into the oocyte rather than using electroporation fusion. See, for example, Collas and Barnes, Mol. Reprod. Dev., 38:264-267 (1994). After fusion, the resultant fused NT units are then placed in a suitable medium until activation, for example, CR1aa medium. Typically activation can be effected shortly thereafter, for example less than 24 hours later, or about 4-9 hours later, or optimally 1-2 hours after fusion. In a preferred embodiment, activation occurs at least one hour post fusion and at 40-41 hours post maturation.

The NT unit can be activated by known methods. Such methods include, for example, culturing the NT unit at subphysiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock can be used to activate NT embryos after fusion. See, for example, U.S. Pat. No. 5,496,720, to Susko-Parrish et al. Fusion and activation can be induced by application of an AC pulse of 5 V for 5 s followed by two DC pulses of 1.5 kV/cm for 60 μs each using an ECM2001 Electrocell Manipulator (BTX Inc., San Diego, Calif.). Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units, or "fused embyos", can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media, and, in one specific example, the activated NT units can be cultured in NCSU-23 medium for about 1-4 h at approximately 38.6° C. in a humidified atmosphere of 5% CO2.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, about 4 to 128 cells, or at least about 50 cells.

Activated NT units can then be transferred (embryo transfers) to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers can then be performed about 22-26 h after the hCG injection. In one embodiment, the pregnancy can be brought to term and result in the birth of live offspring. In another embodiment, the pregnancy can be terminated early and embryonic cells can be harvested.

Breeding for Desired Homozygous Knockout Animals

In another aspect, the present invention provides a method for producing viable animals that lack any expression of functional alpha-1,3-GT is provided by breeding a male heterozygous for the alpha-1,3-GT gene with a female heterozygous for the alpha-1,3-GT gene. In one embodiment, the animals are heterozygous due to the genetic modification of one allele of the alpha-1,3-GT gene to prevent expression of that allele. In another embodiment, the animals are heterozygous due to the presence of a point mutation in one allele of the alpha-1,3-GT gene. In another embodiment, the point mutation can be a T-to-G point mutation at the second base of exon 9 of the alpha-1,3-GT gene. In one specific embodiment, a method to produce an animal that lacks any expression of functional alpha-1,3-GT is provided wherein a male pig that contains a T-to-G point mutation at the second base of exon 9 of the alpha-1,3-GT gene is bred with a female pig that contains a T-to-G point mutation at the second base of exon 9 of the alpha-1,3-GT gene.

In one embodiment, sexually mature animals produced from nuclear transfer from donor cells that carrying a double knockout in the alpha-1,3-GT gene, can be bred and their offspring tested for the homozygous knockout. These homozygous knockout animals can then be bred to produce more animals.

In another embodiment, oocytes from a sexually mature double knockout animal can be in vitro fertilized using wild type sperm from two genetically diverse pig lines and the embryos implanted into suitable surrogates. Offspring from these matings can be tested for the presence of the knockout, for example, they can be tested by cDNA sequencing, PCR, toxin A sensitivity and/or lectin binding. Then, at sexual maturity, animals from each of these litters can be mated.

In certain methods according to this aspect of the invention, pregnancies can be terminated early so that fetal fibroblasts can be isolated and further characterized phenotypically and/or genotypically. Fibroblasts that lack expression of the alpha-1,3-GT gene can then be used for nuclear transfer according to the methods described herein (see also Dai et al.) to produce multiple pregnancies and offspring carrying the desired double knockout.

III. Types of Genetically Modified Animals/Additional Genetic Modifications

In one aspect of the present invention, animals are provided in which one allele of the alpha-1,3-GT gene is inactivated via a genetic targeting event. In another aspect of the present invention, porcine animals are provided in which both alleles of the alpha-1,3-GT gene are inactivated via a genetic targeting event. In one embodiment, the gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knockout") or insertion ("knockin") techniques. Additional genes for a desired protein or regulatory sequence that modulate transcription of an existing sequence can be inserted.

Thus, in another aspect of the present invention, the alpha-1,3-GT gene can be rendered inactive through at least one point mutation. In one embodiment, one allele of the alpha-1,3-GT gene can be rendered inactive through at least one point mutation. In another embodiment, both alleles of the alpha-1,3-GT gene can be rendered inactive through at least one point mutation. In one embodiment, this point mutation can occur via a genetic targeting event. In another embodiment, this point mutation can be naturally occurring. In one specific embodiment the point mutation can be a T-to-G mutation at the second base of exon 9 of the alpha-1,3-GT gene (FIG. 1). Pigs carrying a naturally occurring point mutation in the alpha-1,3-GT gene allow for the production of alpha1,3GT-deficient pigs free of antibiotic-resistance genes and thus have the potential to make a safer product for human use. In other embodiments, at least two, at least three, at least four, at least five, at least ten or at least twenty point mutations can exist to render the alpha-1,3-GT gene inactive. In other embodiments, pigs are provided in which both alleles of the alpha-1,3-GT gene contain point mutations that prevent any expression of functional alpha1,3GT. In a specific embodiment, pigs are provided that contain the T-to-G mutation at the second base of exon 9 in both alleles of the alpha-1,3-GT gene (FIG. 1).

Another aspect of the present invention provides an animal, in which both alleles of the alpha-1,3-GT gene are inactivated, whereby one allele is inactivated by a genetic targeting event and the other allele is inactivated via a naturally occurring point mutation. In one embodiment, a porcine animal is provided, in which both alleles of the alpha-1,3-GT gene are inactivated, whereby one allele is inactivated by a genetic targeting event and the other allele is inactivated due to presence of a T-to-G point mutation at the second base of exon 9. In a specific embodiment, a porcine animal is provided, in which both alleles of the alpha-1,3-GT gene are inactivated, whereby one allele is inactivated via a targeting construct directed to Exon 9 (FIG. 6) and the other allele is inactivated due to presence of a T-to-G point mutation at the second base of exon 9.

In a further embodiment, tissue can be obtained from animals lacking any functional expression of the alpha-1,3-GT gene that also can contain additional genetic modifications. Such genetic modifications can include additions and/or deletions of other genes to prevent rejection, promote wound healing, and/or minimize or eliminate unwanted pathogens (such as prions or retroviruses).

PERV refers to a family of retrovirus of which three main classes have been identified to date: PERV-A (Genbank Accession No. AF038601), PERV-B (EMBL Accession No. PERY17013) and PERV-C (Genbank Accession No. AF038600) (Patience et al 1997, Akiyoshi et al 1998). The gag and pol genes of PERV-A, B, and C are highly homologous, it is the env gene that differs between the different types of PERV (eg., PERV-A, PERV-B, PERV-C). PERV-D has also recently been identified (see, for example, U.S. Pat. No. 6,261,806).

In one of the present invention, porcine endogenous retrovirus (PERV) genes can be regulated by the expression interfering RNA molecules (iRNA). For example, at least two iRNA molecules can be used so that the expression of the PERV virus is functionally eliminated or below detection levels (see, for example, U.S. Ser. No. 60/523,938). In a further embodiment, other viruses, including but not limited to porcine respiratory and reproductive syndrome (PRRS) virus are inactivated or down modulated either via homologous recombination or using an inhibitory RNA (RNAi) approach. In the case of down regulation using RNAi, gene sequences encoding small inhibitory RNAs are expressed as a transgene and introduced into pigs either via microinjection, ICSI, nuclear transfer, or using sperm mediated gene tranfer.

In another embodiment, the expression of additional genes responsible for xenograft rejection can be eliminated or reduced. Such genes include, but are not limited to the CMP-NEUAc Hydroxylase Gene, the isoGloboside 3 Synthase gene, and the Forssman synthase gene. In addition, genes or cDNA encoding complement related proteins, which are responsible for the suppression of complement mediated lysis can also be expressed in the animals and tissues of the present invention. Such genes include, but are not limited to CD59, DAF, MCP and CD46 (see, for example, WO 99/53042; Chen et al. Xenotransplantation, Volume 6 Issue 3 Page 194—August 1999, which describes pigs that express CD59/DAF transgenes; Costa C et al, Xenotransplantation. 2002 January; 9(1):45-57, which describes transgenic pigs that express human CD59 and H-transferase; Zhao L et al.,; Diamond L E et al. Transplantation. 2001 Jan. 15; 71(1):132-42, which describes a human CD46 transgenic pigs.

Additional modifications can include expression of tissue factor pathway inhibitor (TFPI). heparin, antithrombin, hirudin, TFPI, tick anticoagulant peptide, or a snake venom factor, such as described in WO 98/42850 and U.S. Pat. No. 6,423,316, entitled "Anticoagulant fusion protein anchored to cell membrane"; or compounds, such as antibodies, which down-regulate the expression of a cell adhesion molecule by the cells, such as described in WO 00/31126, entitled "Suppression of xenograft rejection by down regulation of a cell adhesion molecules" and compounds in which co-stimulation by signal 2 is prevented, such as by administration to the organ recipient of a soluble form of CTLA-4 from the xenogeneic donor organism, for eample as described in WO 99/57266, entitled "Immunosuppression by blocking T cell co-stimulation signal 2 (B7/CD28 interaction)".

Certain aspects of the invention are described in greater detail in the non-limiting Examples that follow.

EXAMPLES

Example 1

Production of Porcine Cells Heterozygous for the Alpha-1,3-GT Gene

Isolation and transfection of primary porcine fetal fibroblasts. Fetal fibroblast cells (PCFF4-1 to PCFF4-10) were isolated from 10 fetuses of the same pregnancy at day 33 of gestation. After removing the head and viscera, fetuses were washed with Hanks' balanced salt solution (HBSS; Gibco-BRL, Rockville, Md.), placed in 20 ml of HBSS, and diced with small surgical scissors. The tissue was pelleted and resuspended in 50-ml tubes with 40 ml of DMEM and 100 U/ml collagenase (Gibco-BRL) per fetus. Tubes were incubated for 40 min in a shaking water bath at 37° C. The digested tissue was allowed to settle for 3-4 min and the cell-rich supernatant was transferred to a new 50-ml tube and pelleted. The cells were then resuspended in 40 ml of DMEM containing 10% fetal calf serum (FCS), 1× nonessential amino acids, 1 mM sodium pyruvate and 2 ng/ml bFGF, and seeded into 10 cm. dishes. All cells were cryopreserved upon reaching confluence. SLA-1 to SLA-10 cells were isolated from 10 fetuses at day 28 of pregnancy. Fetuses were mashed through a 60-mesh metal screen using curved surgical forceps slowly so as not to generate excessive heat. The cell suspension was then pelleted and resuspended in 30 ml of DMEM containing 10% FCS, 1× nonessential amino acids, 2 ng/ml bFGF, and 10 µg/ml gentamycin. Cells were seeded in 10-cm dishes, cultured one to three days, and cryopreserved. For transfections, 10 µg of linearized vector DNA was introduced into 2 million cells by electroporation. Forty-eight hours after transfection, the transfected cells were seeded into 48-well plates at a density of 2,000 cells per well and were selected with 250 µg/ml of G418.

Figure 6:
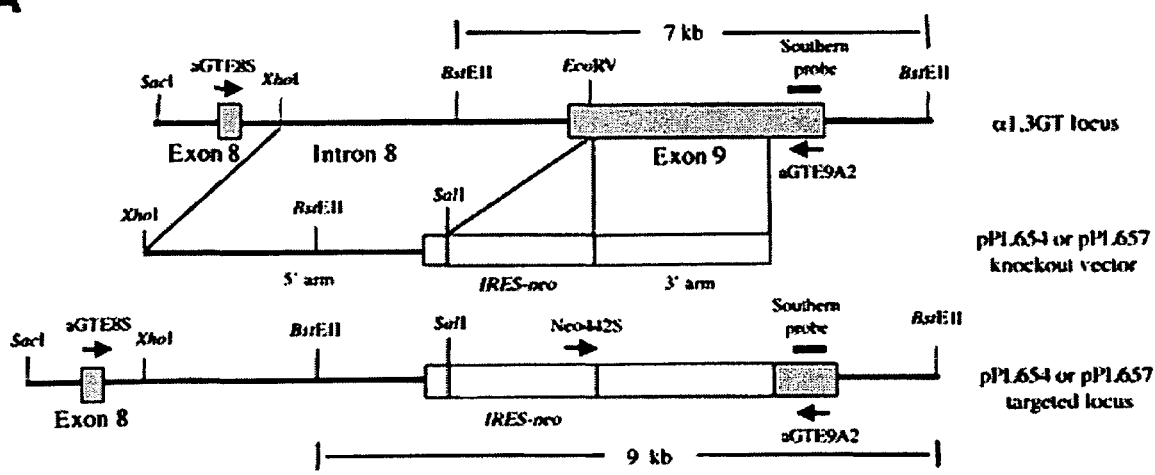
FIG. 6 is a diagram of the porcine alpha-1,3-GT locus, corresponding to alpha-1,3-GT genomic sequences that can be used as 5' and 3' arms in alpha-1,3-GT knockout vectors, and the structure of the targeted locus after homologous recombination. The names of names and positions of the primers used for 3'PCR and long-range PCR are indicated by short arrows. The short bar indicates the probe used for alpha-1,3-GT Southern blot analysis. The predicted size of Southern bands with BstEII digestion for both the endogenous alpha-1,3-GT locus and the alpha-1,3-GT targeted locus is also indicated.

Knockout vector construction Two alpha-1,3-GT knockout vectors, pPL654 and pPL657, were constructed from isogenic DNA of two primary porcine fetal fibroblasts, SLA1-10 and PCFF4-2 cells. A 6.8-kb alpha-1,3-GT genomic fragment, which includes most of intron 8 and exon 9, was generated by PCR from purified DNA of SLA1-10 cells and PCFF4-2 cells, respectively. The unique EcoRV site at the 5' end of exon 9 was converted into a SalI site and a 1.8-kb IRES-neo-poly A fragment was inserted into the SalI site. IRES (internal ribosome entry site) functions as a translation initial site for neo protein. Thus, both vectors have a 4.9-kb 5' recombination arm and a 1.9-kb 3' recombination arm (FIG. 6).

3'PCR and long-range PCR Approximately 1,000 cells were resuspended in 5 µl embryo lysis buffer (ELB) (40 mM Tris, pH 8.9, 0.9% Triton X-100, 0.9% NP40, 0.4 mg/ml Proteinase K), incubated at 65° C. for 15 min to lyse the cells and heated to 95° C. for 10 min to inactivate the Proteinase K. For 3' PCR analysis, fragments were amplified using the Expand High Fidelity PCR system (Roche Molecular Biochemicals) in 25 µl reaction volume with the following parameters: 35 cycles of 1 min at 94° C., 1 min at 60° C., and 2 min at 72° C. For LR-PCR, fragments were amplified by using TAKARA LA system (Panvera/Takara) in 50 µl reaction volume with the following parameters: 30 cycles of 10 s at 94° C., 30 s at 65° C., 10 min+20 s increase/cycle at 68° C., followed by one final cycle of 7 min at 68° C. 3'PCR and LR-PCR conditions for purified DNA was same as cells except that 1 µl of purified DNA (30 µg/ml) was mixed with 4 µl ELB.

Southern blot analysis of cell samples Approximately 106 cells were lysed overnight at 60° C. in lysis buffer (10 mM Tris, pH 7.5, 10 mM EDTA, 10 mM NaCl, 0.5% (w/v) Sarcosyl, 1 mg/ml proteinase K) and the DNA precipitated with ethanol. The DNA was then digested with BstEII and separated on a 1% agarose gel. After electrophoresis, the DNA was transferred to a nylon membrane and probed with the 3'-end digoxigenin-labeled probe. Bands were detected using a chemiluminescent substrate system (Roche Molecular Biochemicals).

Results Antibiotic (G418) resistant colonies were screened by 3' PCR with neo442S and αGTE9A2 as forward and reverse primers. Neo442S is at the 3' end of the neo gene and αGTE9A2 is at the 3' end of exon 9 in sequences located outside of the 3' recombination arm (FIG. 6). Therefore, only through successful targeting at the α1,3GT locus would the expected 2.4 kb PCR product be obtained. From a total of seven transfections in four different cell lines, 1105 G418 resistant colonies were picked, of which 100 (9%) were positive for α1,3 GT gene disruption in the initial 3' PCR screen (range 2.5-12%). Colonies 657A-A8, 657A-I6, and 657A-I11 showed the expected 2.4 kb band, while control PCFF4-6 cells, and another G418 resistant colony, 657A-P6, were negative. A portion of each 3' PCR positive colony was frozen down immediately, in several small aliquots, for future use in NT experiments, while the rest of cells were expanded for long-range PCR (LR-PCR) and Southern analysis.

Since PCR analysis to detect recombination junctions, or mRNA analysis (RT-PCR) can generate false positive results, a long-range PCR, which would encompass the entire targeted region, was performed. The LR-PCR covers the 7.4 kb α1,3GT genomic sequence from exon 8 to the end of exon 9, with both primers (aGTE8S and aGTE9A2) located outside of the recombination region (FIG. 2). The control PCFF4-6 cells, and the 3' PCR-negative colony, 657A-P6, showed only the endogenous 7.4 kb band from the wild-type α1,3GT locus. In contrast, three of the 3' PCR positive colonies, 657A-A8, 657A-I6 and 657A-I11, showed both the 7.4 kb endogenous band, and a new 9.2 kb band, of the size expected for targeted insertion of the 1.8 kb IRES-neo cassette into the α1,3GT locus.

Approximately half (17/30) of the LR-PCR positive colonies were successfully expanded to yield sufficient cell numbers (1×106 cells) for Southern analysis. It was anticipated that the colonies would be heterozygous for knockout at the α1,3 GT locus, and thus they should have one normal, unmodified gene copy, and one disrupted copy of the α1,3 GT gene. With BstEII digestion, the α1,3 GT knockout cells should show two bands: one 7 kb band of the size expected for the endogenous α1,3 GT allele, and a 9 kb band characteristic of insertion of the IRES-neo sequences at the α1,3 GT locus (FIG. 2). All 17 LR-PCR positive colonies were confirmed by Southern analysis for the knockout. The same membranes were re-probed with sequences specific for neo and the 9 kb band was detected with the neo probe, thus confirming targeted insertion of the IRES-neo cassette at the disrupted α1,3GT locus.

Example 2

Production of Porcine Cells Homozygous for the Alpha-1,3-GT Gene

Heterozygous alpha-1,3-GT knockout fetal fibroblasts, (657A-I11 1-6) cells, were isolated from a day-32 pregnancy as described above (See also Dai et al. Nature Biotechnology 20:451 (2002)). After removing the head and viscera, some fetuses were washed with Hanks' balanced salt solution (HBSS; Gibco-BRI, Rockville, Md.), placed in 20 ml of HBSS, and diced with small surgical scissors. The tissue was pelleted and resuspended in 50-ml tubes with 40 ml of DMEM and 100 U/ml collagenase (Gibco-BRL) per fetus. Tubes were incubated for 40 min in a shaking water bath at 37° C. The digested tissue was allowed to settle for 3-4 min and the cell-rich supernatant was transferred to a new 50-ml tube and pelleted. The cells were then resuspended in 40 ml of DMEM containing 10% fetal calf serum (FCS), 1× nonessential amino acids, 1 mM sodium pyruvate (Gibco-BRL), and 2 ng/ml basic fibroblast growth factor (bFGF; Roche Molecular Biochemicals, Indianapolis, Ind.) and seeded into 10-cm dishes. All cells were cryopreserved upon reaching confluence. After removing the head and viscera, some fetuses were washed with Hanks' balanced salt solution (HBSS; Gibco-BRI, Rockville, Md.), placed in 20 ml of HBSS, and diced with small surgical scissors. Fetuses were mashed through a 60-mesh metal screen (Sigma, St. Louis, Mo.) using curved surgical forceps slowly so as not to general excessive heat. The cell suspension was then pelleted and resuspended in 30 ml of DMEM containing 10% FCS, 1× nonessential amino acids, 2 ng/ml bFGF, and 10 µg/ml gentamycin. Cells were seeded in 10-cm dishes, cultured one to three days, and cryopreserved. For transfections, 10 µg of linearized vector DNA was introduced into 2 million cells by electroporation. Forty-eight hours after transfection, the transfected cells were seeded into 480-well plates at a density of 2,000 cells per well and were selected with 250 µg/ml of G418 (Gibco-BRL). An ATG (start codon)-targeting alpha-1,3-GT knockout vector was constructed (pPL680), which also contained a neo gene, to knock out the second allele of the alpha-1,3-GT gene. These cells were transfected by electroporation with pPL680 and selected for the alpha1,3Gal-negative phenotype with purified C. difficile toxin A (described below).

Example 3

Selection with C. difficile Toxin A for Porcine Cells Homozygous for the Alpha-1,3-GT Gene Toxin A Cyototoxicity Curve
Porcine cells (PCFF4-6) were exposed for 1 hour or overnight to ten-fold serial dilutions of toxin A (0.00001 □g/ml to 10 □g/ml). Cells were cultured in 24 well plates and were incubated with the toxin for 1 hour or overnight at 37 C. The results of this exposure are detailed in Table 2. Clearly, a 1 hour exposure to toxin A at >1 □g/ml resulted in a cytotoxic effect on >90% of the cells. A concentration of toxin A at or slightly above 1 □g/ml therefore was chosen for selection of genetically altered cells.

TABLE 2

Toxin A toxicity at 1 hour and overnight exposure

| [Toxin A], µg/ml | 1 hour incubation | Overnight incubation |
|---|---|---|
| 0 | 100% confluency | 100% confluency |
| .00001 | 100% confluency | 100% confluency |
| .0001 | 100% confluency | 100% confluency |
| .001 | 100% confluency | 100% confluency |
| .01 | 100% confluency | 50% confluency, 50% rounded |
| .1 | 90% confluency | Same as 10 ug/ml |
| 1 | >90% rounded | Same as 10 ug/ml |
| 10 | All cells rounded up | All cells rounded up, some lifted |

Disaggregated cells from a porcine embryo (I-11:1-6) which contained a previously identified targeted knockout in one allele of the gal alpha-1,3-GT gene (Dai et al.) were transfected with 10 ug linearized vector DNA (promoter trap) by electroporation. After 48 hours, the cells were seeded into 48 well plates at a density of 2000 cells per well and selected with 250 ug/ml G418. Five days post-transfection, media was withdrawn from the wells, and replaced with 2 ug/ml toxin A in culture media (DMEM high glucose with 2.8 ng/ml bFGF and 20% FCS). Cells were exposed to the selective effect of toxin A for 2 hours at 37 C. The toxin A-containing media, along with any affected cells that have released from the plate surface, was withdrawn, the remaining cells washed with fresh media, and the media without toxin A replaced. Ten days later, cells were again exposed to toxin A at 1.3 ug/ml in media for 2 hours at 37 C. The media, toxin A, and any cells in solution were removed, the remaining cells washed, and the media replaced.

Sixteen days post-transfection, a single colony that exhibited toxin A insensitivity, designated 680B1, was harvested and a portion sent for DNA analysis and lectin staining. DNA analysis indicated that the toxin A insensitivity was not due to integration of the second target vector; however, the cells did not stain with GSL IB-4 lectin, indicating that a functional knockout of the locus had occurred. The 680B1 double knockout cells were used for nuclear transfer into 5 recipients and three pregnancies resulted. Two of these pregnancies spontaneously aborted in the first month; the four fetuses from the remaining pregnancy were harvested on day 39 of the pregnancy and the cells disaggregated and seeded into tissue culture. These fetal cells (680B1-1, 680B1-2, 680B1-3, 680B1-4) were exposed to toxin A at 1 ug/ml for 1 hour at 37 C, followed by medium removal, cell washing, and medium replacement without toxin A. Fetuses 1, 2, and 4 were not affected by toxin A, whereas most of the cells from fetus 3 rounded up, indicating that this embryo was sensitive to the cytotoxic effects of the toxin A.

Fetuses 1, 2, and 4 did not bind GS IB4 lectin, as indicated by FACS analysis (see Table 3), while fetus 3 did bind lectin. This suggests that fetuses 1, 2, and 4 do not carry the epitope alpha 1,3 gal for which this particular lectin is specific.

TABLE 3

FACS Results of 680B1-1 to 680B1-4 Cells with GS-IB4 Lectin
GS IB4 lectin positive cells (%)

| Cell | Unstaining | 50 µg/ml IB4 lectin | 100 µg/ml IB4 lectin |
|---|---|---|---|
| HeLa Cells (Negative CTL) | 1% | 2% | 2.8% |
| PCFF4-6 cells (Positive CTL) | 0.2% | 76% | 91% |
| PFF4 cells (Positive CTL) | 1.5% | 82% | 94% |
| 680B1-1 cells | 0.6% | 0.8% | 0.9% |
| 680B1-2 cells | 1.2% | 1.2% | 1.1% |
| 680B1-3 cells | 8% | 35% | 62% |
| 680B1-4 cells | 0.6% | 0.8% | 0.9% |

A complement fixation assay was run on cells from all four fetuses. The complement lysis assay was developed as a bioassay for lack of alpha gal expression. Human serum contains high levels of pre-formed antibody against alpha gal as well as the full portfolio of complement regulatory proteins (the C3 pathway). The presence of alpha gal on the surface of a cell, upon binding of anti-alpha gal antibody, activates the complement cascade, and results in complement-mediated cell lysis. Alpha-gal negative cells would be resistant to complement mediated lysis. In three separate tests, B1 and control pig cells were exposed to human serum plus complement, and assays performed to evaluate sensitivity or resistance to alpha-gal-initiated, complement-mediated cell lysis. The assay was performed with B1-1, B1-2, and B1-4 cells, as well as heterozygous GT KO cells (B1-3, gal positive), and with wild-type alpha-gal (+) PCFF4-6 pig cells as a control. Cells were exposed to one of three treatments; two negative controls, bovine serum albumin (BSA), and heat-inactivated human serum (HIA-HS) do not contain any functional complement protein and thus would not be expected to cause any significant cell lysis; the third treatment, non-heat-inactivated human serum (NHS) contains functional human complement as well as anti-gal specific antibodies, and thus would be expected to lyse cells which have galactose alpha 1,3 galactose on their cell surface.

The results shown in FIG. 1 clearly demonstrate that B1-1, B-2 and B1-4 cells are resistant to human complement-mediated lysis while B1-3 cells, which is α1,3 Gal positive, is still as sensitive to human plasma as are wild-type PCFF4-6 cells.

Sequencing results of cDNA from all fetuses indicated that fetuses 1, 2 and 4 contain a point mutation in the second alpha 1,3 GT allele, a change that could yield a dysfunctional enzyme (see FIG. 2). This mutation occurred at bp424 of the coding region, specifically, the second base pair of exon 9, of the alpha-1,3-GT (GGTA1) gene (GenBank Accession No. L36152) as a conversion of a thymine to a guanine residue, which results in an amino acid substitution of tyrosine at aa 142 to an aspartic acid.

Figure 3:
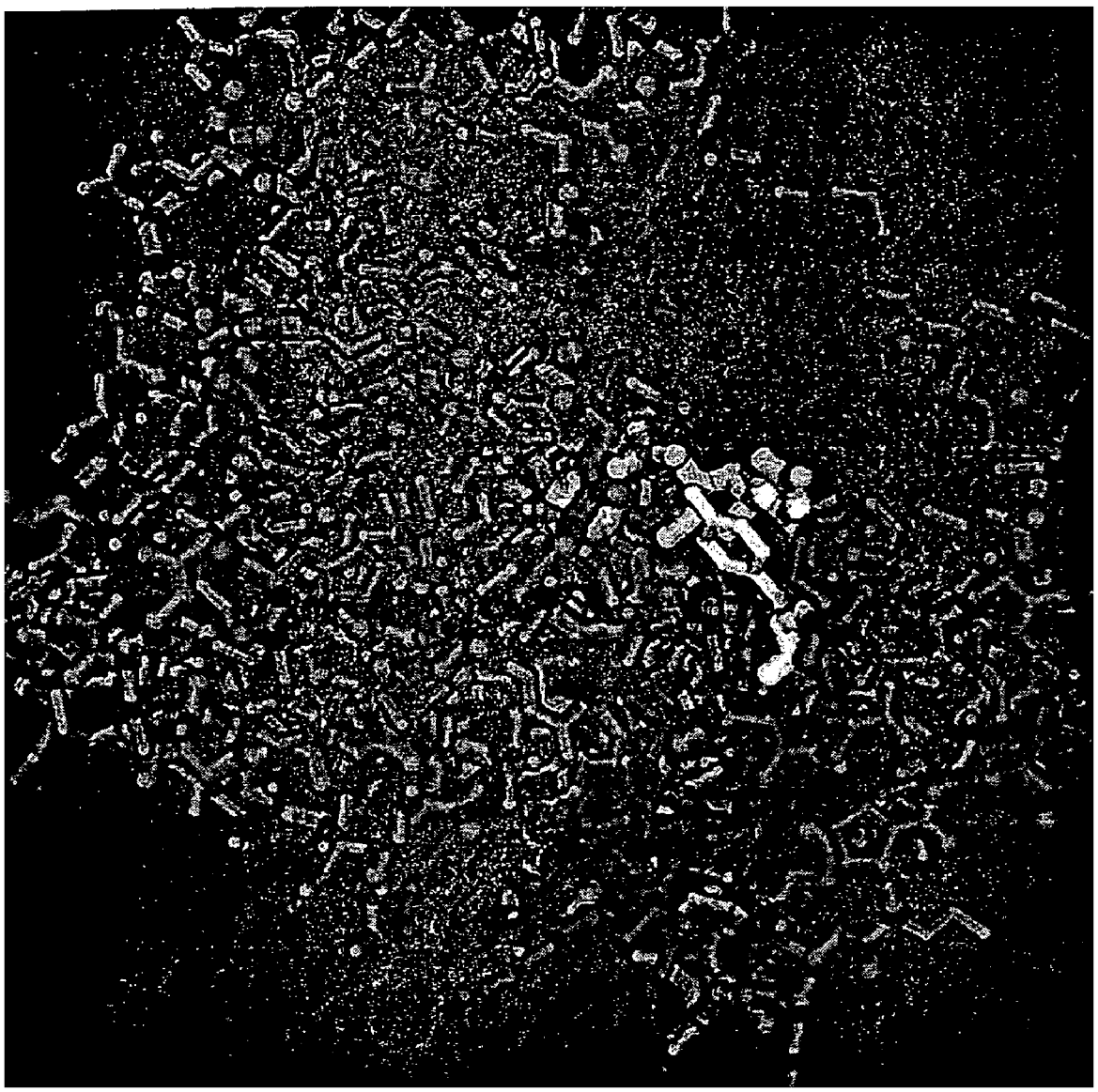
FIG. 3 is a representation of a 3-dimensional model of the UDP binding site of bovine alpha1,3GT. The aromatic ring of the tyrosine residue (foreground, white) can be seen in close proximity to the uracil base of UDP (grayscale).

This is a significant conversion, as the tyrosine, a hydrophilic amino acid, is a critical component of the UDP binding site of alpha 1,3GT (see FIG. 3). Analysis of the crystal structure of bovine alpha-1,3-GT protein showed that this tyrosine is the center of the catalytic domain of the enzyme, and is involved in UDP-Gal binding (Gastinel et. al., EMBO Journal 20(4): 638-649, 2001). Therefore, a change from tyrosine (a hydrophobic amino acid) to aspartic acid (a hydrophilic amino acid) would be expected to cause disruption of the αGT function (as observed).

To confirm that the mutated cDNA will not make functional αGT protein, the cDNAs from the second allele of all 4 cells were cloned into an expression vector and this GT expression vector transfected into human fibroblast cells (HeLa cells) as well as into primary Rhesus monkey cells. As humans and Old World monkeys lack a functional alpha 1,3 GT gene, the HeLa cells would not have an alpha 1,3 galactose on their cell surface (as assayed by lectin binding experiments). Results showed that the HeLa and monkey cells, when transfected with cDNA obtained from B1-1, B1-2 and B1-4 cells, were still α1,3 Gal negative by IB4-lectin staining, while Hela and Rhesus monkey cells transfected with cDNA from the B1-3, made a functional alpha 1,3 GT transcript and subsequently were α1,3Gal positive. Clearly, cells with the aspartate mutation (instead of tyrosine) cannot make functional alpha 1,3 galactosyl transferase Example 4

Generation of Cloned Pigs Using Homozygous Alpha 1,3 GT-Deficient Fetal Fibroblasts as Nuclear Donors Preparation of Cells for Nuclear Transfer.

Donor cells were genetically manipulated to produce cells homozygous for alpha 1,3 GT deficiency as described generally above. Nuclear transfer was performed by methods that are well known in the art (see, e.g., Dai et al., Nature Biotechnology 20: 251-255, 2002; and Polejaeva et al., Nature 407: 86-90, 2000).

Oocytres were collected 46-54 h after the hCG injection by reverse flush of the oviducts using pre-warmed Dulbecco's phosphate buffered saline (PBS) containing bovine serum albumin (BSA; 4 gl$^{-1}$) (as described in Polejaeva, I. A., et al. (Nature 407, 86-90 (2000)). Enucleation of in vitro-matured oocytes (BioMed, Madison, Wis.) was begun between 40 and 42 hours post-maturation as described in Polejaeva, I. A., et al. (Nature 407, 86-90 (2000)). Recovered oocytes were washed in PBS containing 4 gl$^{-1}$ BSA at 38° C., and transferred to calcium-free phosphate-buffered NCSU-23 medium at 38° C. for transport to the laboratory. For enucleation, we incubated the oocytes in calcium-free phosphate-buffered NCSU-23 medium containing 5 μg ml$^{-1}$ cytochalasin B (Sigma) and 7.5 μg ml$^{-1}$ Hoechst 33342 (Sigma) at 38° C. for 20 min. A small amount of cytoplasm from directly beneath the first polar body was then aspirated using an 18 μM glass pipette (Humagen, Charlottesville, Va.). We exposed the aspirated karyoplast to ultraviolet light to confirm the presence of a metaphase plate.

For nuclear transfer, a single fibroblast cell was placed under the zona pellucida in contact with each enucleated oocyte. Fusion and activation were induced by application of an AC pulse of 5 V for 5 s followed by two DC pulses of 1.5 kV/cm for 60 μs each using an ECM2001 Electrocell Manipulator (BTX Inc., San Diego, Calif.). Fused embryos were cultured in NCSU-23 medium for 1-4 h at 38.6° C. in a humidified atmosphere of 5% CO$_2$, and then transferred to the oviduct of an estrus-synchronized recipient gilt. Crossbred gilts (large white/Duroc/landrace) (280-400 lbs) were synchronized as recipients by oral administration of 18-20 mg Regu-Mate (Altrenogest, Hoechst, Warren, N.J.) mixed into their feed. Regu-Mate was fed for 14 consecutive days. Human chorionic gonadotropin (hCG, 1,000 units; Intervet America, Millsboro, Del.) was administered intramuscularly 105 h after the last Regu-Mate treatment. Embryo transfers were done 22-26 h after the hCG injection.

Toxin A was then used to selected the porcine fibroblasts as nuclear donors that were produced as described in detail herein above.

Embryo Transfers and Resulting Live Births.

Figure 4:
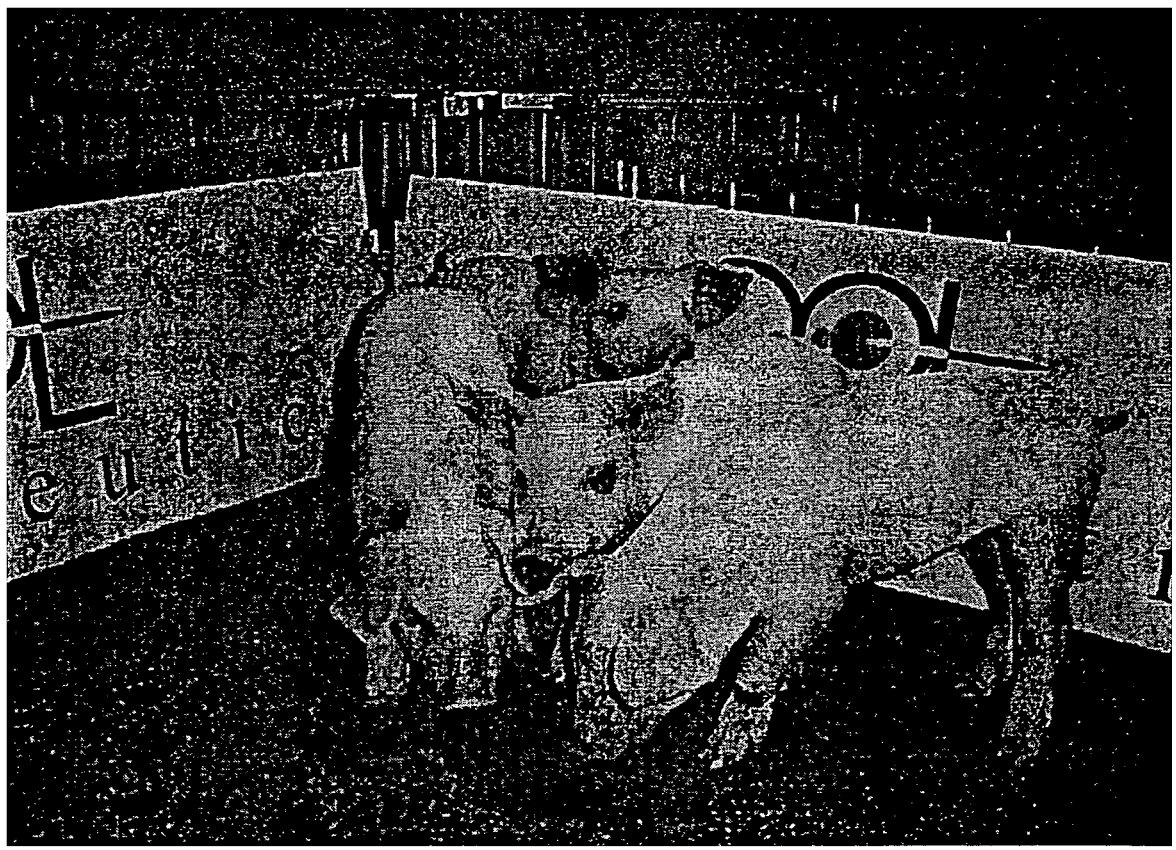
FIG. 4 is a photograph of homozygous, alpha-1,3-GT deficient cloned pigs produced by the methods of the invention, born on Jul. 25, 2002.

In the initial attempt to produce live alpha-1,3-GT dKO pigs by nuclear transfer, a total of 16 embryo transfers were performed with genetically manipulated donor cells. Nine initial pregnancies were established but only two went beyond Day 75 of gestation. Five piglets were born on the 25 Jul. 2002. One piglet died immediately after birth and another four were born alive and appeared normal (FIG. 4).

Example 5

Analysis of Homozygous Alpha 1,3 GT Knockout Pigs

Tail fibroblast cells and umbilicus tissue sections were obtained from all 5 double knockout piglets and stained using the GS-IB4 lectin as described previously. No staining was observed, indicating a complete lack of galactose alpha 1,3 galactose epitope on the surface of tissues from these animals (data not shown). Aorta endothelial cells and muscle and tail fibroblasts isolated from the dead piglet (761-1) were negative with GS-IB4 lectin staining. FACS analysis of muscle fibroblasts from piglet 761-1 also showed a negative result for GS-IB4 binding. Tissue sections of liver, kidney, spleen, skin, intestine, muscle, brain, heart, pancreas, lung, aorta, tongue, umbilicus, and tail obtained from piglet 761-1 were all negative with GS-IB4 staining, indicating a complete lack of detectable cell surface alpha 1,3Gal epitopes (Phelps et al., Science 299: 411-414, 2003 including figure S3).

Figure 5:
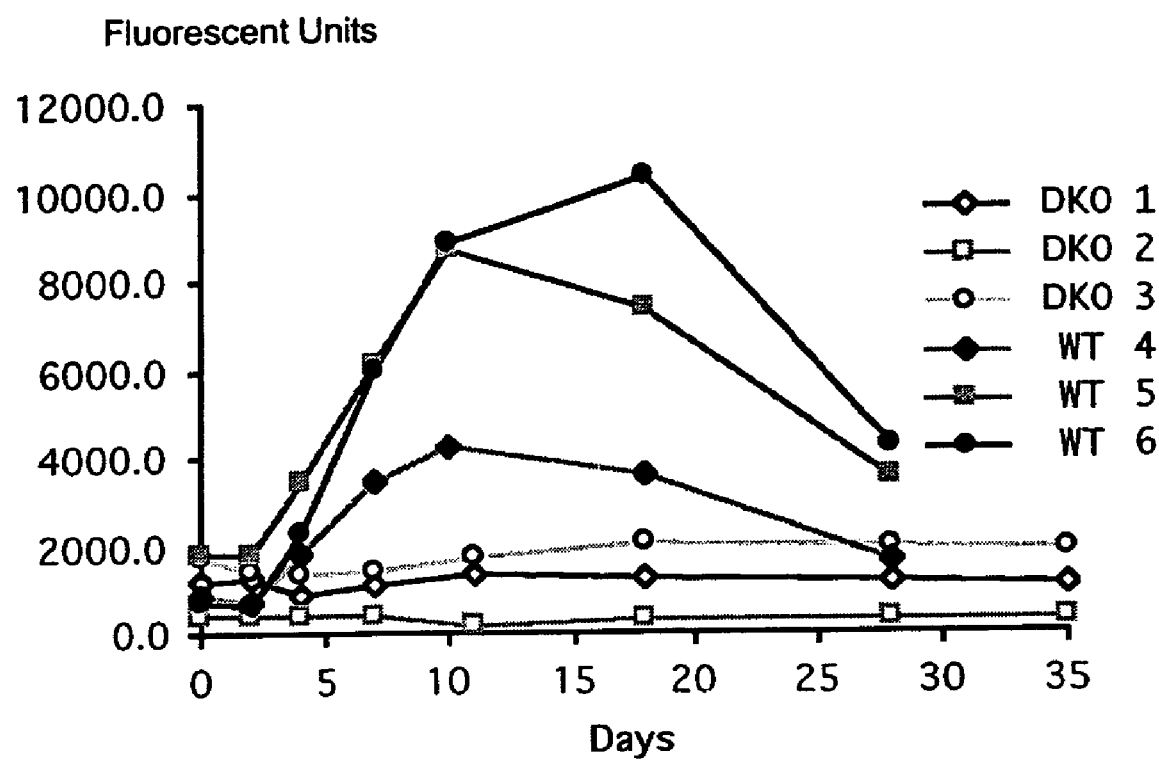
FIG. 5 is a graph depicting Anti-alpha-1,3-gal IgM levels before and after injections of piglet islet-like cell clusters (ICC) in alpha-1,3-GT KO mice. Each mouse received three serial ICC injections via i.p. (200-500 ICC per injection) over 4 days. All three recipients of wild-type (WT) piglet ICCs showed a significant elevation of anti-alpha 1,3Gal IgM titer and subsequent return to baseline 4 weeks after ICC implants. Sera from all three mice injected with alpha-1,3-GT DKO piglet ICCs maintained low baseline values of anti-alpha-1, 3-gal IgM titer during the observation time of 35 days (Phelps et al., Science 299: 411-414, 2003, figure S4).

We performed an in vivo immunogenicity test with alpha 1,3GT-knockout mice. We injected islet-like cell clusters (ICCs) isolated from the pancreas of piglet 761-1 intraperitoneally into alpha 1,3GT knockout mice. We used ICCs from a neonatal wild-type piglet as a control. As shown in FIG. 5, no increase in the titer of immunoglobulin M (IgM) to alpha 1,3Gal was observed in alpha 1,3GT knockout mice after injection with ICCs from the alpha 1,3GT DKO piglet, in contrast to significant IgM titer increases observed in those mice injected with wild-type piglet ICCs (Phelps et al., Science 299: 411-414, 2003 including figure S4). This result clearly demonstrates that the DKO piglet cells do not make any alpha 1,3Gal epitopes.

Sequencing of DNA obtained from all five piglets confirmed the presence of the mutation at bp 424 of the GGTA1 gene, as observed in the 680B1-2 cells used to clone these animals (FIG. 2).

Since this first successful production of a litter of alpha-GT dKO pigs, two subsequent litters of dKO piglets have been produced by nuclear transfer, in one case (litter 662) using the dKO fetal fibroblasts as nuclear donor cells. Litter 660 was produced by nuclear transfer using tail fibroblast cells from a member of the litter 761 as nuclear donor. These births are summarized in Table 4.

TABLE 4

Summary of alpha-GT double knockout births produced by nuclear transfer

| Cell Line | No. Litters | No. Live piglets produced |
|---|---|---|
| A | 8 | 14 |
| B | 2 | 2 |
| C | 1 | 1 |
| Total | | 17 |

* PM = GT allele knockout via point mutation; Neo = GT allele knockout via homologous recombination and insertion of Neo selectable marker gene. All pigs presented in this table are homozygous GT knockouts.

Example 6

Breeding of Heterozygous Alpha 1,3 GT Single Knockout (SKO) Male and Female Pigs to Establish a Miniherd of Double Knockout (DKO) Pigs Southern blot confirmed cloned GT-SKO females and male cloned pigs have been generated. Male and female heterozygous (single gene alpha1,3GT knockout pigs) have been bred by natural breeding and by artificial insemination (AI), in order to generate a herd of DKO pigs for use in preclinical studies and human clinical trials.

Example 7

Decellularization of Dermal Tissue from Double Knockout Animals

The biological tissue to be processed is first procured or harvested from an animal donor in which functional alpha 1,3GT has been inactivated, for example in pigs, as described above. Dermal tissue is excised from the donor animal using a dermatome or other device known to one skilled in the art. The tissue is placed in a stabilizing transportation solution which arrests and prevents osmotic, hypoxic, autolytic and proteolytic degradation, protects against bacterial contamination and reduces mechanical damage that can occur. The stabilizing solution generally contains an appropriate buffer, one or more antioxidants, one or more oncotic agents, an antibiotic, one or more protease inhibitors, as described herein or known to one of skill in the art.

The tissue is then incubated in a processing solution to remove viable antigenic cells (including epithelial cells, endothelial cells, smooth muscle cells and fibroblasts) from the structural matrix without damaging the basement membrane complex or the structural integrity of the collagen matrix. The processing solution generally contains an appropriate buffer, salt, an antibiotic, one or more detergents, one or more protease inhibitors, and/or one or more enzymes as described herein or known to one skilled in the art. Treatment of the tissue with this processing solution is done at a concentration for a period of time such that degradation of the basement membrane complex is avoided and the structural integrity of the matrix is maintained including collagen fibers and elastin to produce decellularized tissue.

After the tissue is decellularized, it is incubated in a cryopreservation solution. This solution generally contains one or more cryoprotectants to minimize ice crystal damage to the structural matrix that could occur during freezing, and one or more dry-protective components, to minimize structural damage alteration during drying and may include a combination of an organic solvent and water which undergoes neither expansion or contraction during freezing. Following incubation in this cryopreservation solution, the tissue is packaged inside a sterile container. As an additional or alternate method, the decellularized tissue matrix is fixed with a crosslinking agent such as glutaraldehyde and stored prior to transplantation.

Example 8

Ligament Harvesting for Xenografts from Double Knockout Animals

The biological tissue to be processed is first procured or harvested from an animal donor in which functional alpha 1,3GT has been inactivated, as described herein. Ligament tissue is excised from the donor animal using an appropriate surgical technique. In the first step, an intact ligament is removed from the knee of a non-human animal. The joint which serves as the source of the ligament is collected from freshly killed animals and immediately placed in a suitable sterile isotonic or other tissue preserving solution. Harvesting of the joints occurs as soon as possible after slaughter of the animal and performed in the cold, i.e., in the approximate range of about 5° C. to about 20° C., to minimize enzymatic degradation of the ligament tissue. The ligament is harvested alone or the ligament is harvested with a block of bone attached to one or both ends. A block of bone representing a cylindrical plug of approximately 9-10 mm in diameter by 20-40 mm in length is left attached to the ligament. The ligament is carefully identified and dissected free of adhering tissue. The xenograft is then washed in about ten volumes of sterile cold water to remove residual blood proteins and water soluble materials. The xenograft is then immersed in alcohol at room temperature for about five minutes, to sterilize the tissue and to remove non-collagenous materials.

After alcohol immersion, the xenograft is implanted into a knee. Alternatively, the xenograft is subjected to at least one of the following treatments: radiation treatment, treatment with alcohol or ozonation, one or more cycles of freezing and thawing, and/or treatment with a chemical cross-linking agent. In the freeze/thaw cycling treatment, the xenograft is thawed by immersion in an isotonic saline bath at room temperature (about 25° C.) for about ten minutes. No external heat or radiation source is used, in order to minimize fiber degradation.

In addition or alternatively, the xenograft is subjected to a cellular disruption treatment to kill the cells of the ligament prior to in vitro digestion of the xenograft with glycosidases. After surface carbohydrate moieties are removed from nucleated cells and extracellular components, nucleated cells, i.e., living cells reexpress the surface carbohydrate moieties.

In addition or alternatively, either before or after the ligament cells are killed, the xenograft is subject to in vitro digestion of the xenograft with glycosidases, enzymatically eliminate antigenic surface carbohydrate moieties. Other enzymes may also be used, in order to remove any residual non-alpha gal charbohydrate moieties.

Prior to implantation, the ligament xenograft of the invention is treated with limited digestion by proteolytic enzymes such as ficin or trypsin to increase tissue flexibility or coated with anticalcification agents, antithrombotic coatings, antibiotics, growth factors, or other drugs known in the art to enhance the incorporation of the xenograft into the recipient knee joint. Additionally or alternatively, the ligament xenograft is further sterilized using known methods, for example, with additional glutaraldehyde or formaldehyde treatment, ethylene oxide sterilization, propylene oxide sterilization, or the like. The xenograft is stored frozen until required for use.

The ligament xenograft, or a segment thereof, is implanted into a damaged human knee joint by those of skill in the art using known arthroscopic surgical techniques. Specific instruments for performing arthroscopic techniques are known to those of skill in the art, which ensure accurate and reproducible placement of ligament implants. Initially, complete diagnostic arthroscopy of the knee joint is accomplished using known methods. The irreparably damaged ligament is removed with a surgical shaver. The anatomic insertion sites for the ligament are identified and drilled to accommodate a bone plug. The size of the bone plug is about 9-10 mm in width by about 9-10 mm in depth by 20-40 mm in length. The xenogeneic ligament is brought through the drill holes and affixed with interference screws. Routine closure is performed.

Example 9:

Tissue Grafts Derived from Small Intestine Submucosa (SIS) from Homozygous Alpha 1,3 Gal Knockout Pigs The tissue graft material is derived from an animal, such as a pig, lacking any functional expression of alpha 1,3 GT, and contains submucosa tissue and basilar mucosa tissue delaminated from a segment of the small intestine, such as the jejunum, a division of the small intestine extending between the duodenum and the ileum.

A SIS graft obtained from the small intestine of alpha 1,3 gal deficient pigs is prepared by first resecting a segment of autogeneous proximal jejunum following a midline laparotomy incision. The resected segment of jejunum is then wrapped in surgical sponges which have been soaked in physiologic saline. Upon completion of the intestinal anastomosis, the excised intestinal segment is prepared by abrading intestinal tissue to remove the outer layers including both the tunica serosa and the tunica muscularis and the inner layers including at least the luminal portion of the tunica mucosa. Under conditions of mild abrasion the tunica mucosa is delaminated between the stratum compactum and the lamina propria. More particularly, following removal of any mesenteric tissues from the intestinal segment utilizing, for example, using Adson-Brown forceps and Metzenbaum scissors, the tunica serosa and the tunica muscularis (the outer tissue layers) are delaminated from the intestinal segment by abrasion using a longitudinal wiping motion with a scalpel handle and moistened gauze. Following eversion of the intestinal segment, the luminal portion of the tunica mucosa is delaminated from the underlying tissue using the same wiping motion. Care is taken to prevent perforation of the submucosa. Also, any tissue "tags" from the delaminated layers remaining on the graft surface are removed. Optionally, the intestinal segment may be everted first, then stripped of the luminal layers, then reinserted to its original orientation for removal of the tunica serosa and the tunica muscularis. The graft material is a whitish, translucent tube of tissue approximately 0.1 mm thick, typically consisting of the tunica submucosa with the attached lamina muscularis mucosa and stratum compactum. For vascular graft preparation, the prepared graft is everted to its original orientation so that the stratum compactum serves as the luminal surface of the graft.

The prepared graft material is typically rinsed with saline and placed in a 10% neomycin sulfate solution for approximately 20 minutes, after which time the graft material is ready for use. The grafts are applied using routine surgical procedures commonly employed for tissue graft applications. For use in non-vascular tissue graft applications, the tubular graft material is cut longitudinally and rolled out to form a "patch" of tissue. The entire tissue delamination procedure described above can be carried out on "patches" of intestinal tissue prepared by cutting the intestinal segment longitudinally and "unrolling" it to form a pre-graft patch. The prepared graft tissue patches can be utilized, for example, as a skin graft material, for dura repair, or for repair of other body tissue defects lending themselves to surgical application of a tissue graft patch having the physical and functional characteristics of the present graft composition. Other applications for Gal KO SIS patch material include for rotator cuff repair, hernia, abdominal wall repair, slings to treat urinary incontinence, burns, skin replacement, cosmetic surgery including breast reconstruction, facial defects, lip reconstruction, eyelid spacer grafts, depressed scar repair, mucosal grafts, nasolavial folds, oral resurfacing, parotidectomy, septal perforation repair, rhinoplasty, temporary wound dressing, wound coverage, tympanoplasty, vestibuloplasty, and other soft tissue defects.

For use in vascular grafts, the diameter of the graft is approximately the same as the diameter of the recipient blood vessel. This is accomplished by manipulating the tissue graft to define a cylinder having a diameter approximately the same as that of the recipient blood vessel and suturing or otherwise securing the tissue graft longitudinally to form said vascular graft. Thus, for example, a vascular graft is prepared by selecting a sterile glass rod having an outer diameter equal to that of the recipient blood vessel and introducing the glass rod into the graft lumen. Redundant tissue is then gathered and the desired lumen diameter achieved by suturing along the length of the graft (for example, using two continuous suture lines or a simple interrupted suture line) or by using other art-recognized tissue securing techniques (see also U.S. Pat. No. 4,956,178).

The invention described herein can be practiced in the absence of any element or elements, limitation or limitations which is not specifically disclosed herein. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed can be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group.

We claim:

1. A tissue product, comprising a tissue stripped of viable cells wherein the tissue is derived from a tissue of a porcine animal in which at least one allele of an α-1,3-galactosyltransferase gene is inactivated and wherein the animal lacks expression of alpha-1,3-galactosyltransferase.

2. The tissue product of claim 1, wherein the tissue stripped of viable cells is produced by enzymatic treatment.

3. The tissue product of claim 1, wherein the tissue is bone.

4. The tissue product of claim 1, wherein the tissue stripped of viable cells is produced by chemical treatment.

5. The tissue product of claim 1, wherein the tissue is selected from the group consisting of tendon, joint, bone and heart valve.

6. The tissue product of claim 2 or 4, wherein the tissue can be further processed via crosslinking treatments.

7. The tissue product of claim 2 or 4, wherein the tissue can be further processed via additional chemical treatments.

* * * * *

SEQUENCE LISTING

<160> NUMBER OF SEQ ID NOS: 5

<210> SEQ ID NO 1
<211> LENGTH: 11
<212> TYPE: DNA
<213> ORGANISM: Sus scrofa

```
<400> SEQUENCE: 1
gctgtcggaa g                                                            11

<210> SEQ ID NO 2
<211> LENGTH: 16
<212> TYPE: DNA
<213> ORGANISM: Sus scrofa

<400> SEQUENCE: 2
atacattgag cattac                                                       16

<210> SEQ ID NO 3
<211> LENGTH: 5
<212> TYPE: PRT
<213> ORGANISM: Sus Scrofa

<400> SEQUENCE: 3

Tyr Ile Glu His Tyr
1               5

<210> SEQ ID NO 4
<211> LENGTH: 16
<212> TYPE: DNA
<213> ORGANISM: Sus scrofa

<400> SEQUENCE: 4
agacattgag cattac                                                       16

<210> SEQ ID NO 5
<211> LENGTH: 5
<212> TYPE: PRT
<213> ORGANISM: Sus scrofa

<400> SEQUENCE: 5

Asp Ile Glu His Tyr
1               5
```